US008586524B2

(12) United States Patent
Sullenger et al.

(10) Patent No.: US 8,586,524 B2
(45) Date of Patent: Nov. 19, 2013

(54) MODULATORS OF PHARMACOLOGICAL AGENTS

(75) Inventors: Bruce A. Sullenger, Durham, NC (US); Christopher P Rusconi, Durham, NC (US)

(73) Assignee: Duke University, Durham, NC (US)

( * ) Notice: Subject to any disclaimer, the term of this patent is extended or adjusted under 35 U.S.C. 154(b) by 1249 days.

(21) Appl. No.: 11/789,992

(22) Filed: Apr. 26, 2007

(65) Prior Publication Data

US 2008/0051339 A1    Feb. 28, 2008

Related U.S. Application Data

(63) Continuation of application No. 10/155,233, filed on May 28, 2002, now Pat. No. 7,300,922.

(60) Provisional application No. 60/293,231, filed on May 25, 2001, provisional application No. 60/331,037, filed on Nov. 7, 2001.

(51) Int. Cl.
*A61K 38/00* (2006.01)
*C12N 15/115* (2010.01)

(52) U.S. Cl.
USPC .......................................... 514/1.1; 514/44 A

(58) Field of Classification Search
None
See application file for complete search history.

(56) References Cited

U.S. PATENT DOCUMENTS

| | | |
|---|---|---|
| 5,245,022 A | 9/1993 | Weis et al. |
| 5,270,163 A | 12/1993 | Gold et al. |
| 5,475,096 A | 12/1995 | Gold et al. |
| 5,476,766 A | 12/1995 | Gold et al. |
| 5,532,130 A | 7/1996 | Alul |
| 5,534,408 A | 7/1996 | Green et al. |
| 5,543,293 A | 8/1996 | Gold et al. |
| 5,552,391 A | 9/1996 | Coutts et al. |
| 5,582,981 A | 12/1996 | Toole et al. |
| 5,594,121 A | 1/1997 | Froehler et al. |
| 5,595,877 A | 1/1997 | Gold et al. |
| 5,606,047 A | 2/1997 | Coutts et al. |
| 5,633,395 A | 5/1997 | Coutts et al. |
| 5,645,985 A | 7/1997 | Froehler et al. |
| 5,660,985 A | 8/1997 | Picken et al. |
| 5,670,633 A | 9/1997 | Cook et al. |
| 5,670,637 A | 9/1997 | Gold et al. |
| 5,681,702 A | 10/1997 | Collins et al. |
| 5,686,242 A | 11/1997 | Bruice et al. |
| 5,696,249 A | 12/1997 | Gold et al. |
| 5,723,323 A | 3/1998 | Kauffman et al. |
| 5,750,729 A | 5/1998 | Alexander et al. |
| 5,756,291 A | 5/1998 | Griffin et al. |
| 5,780,221 A | 7/1998 | Schumacher et al. |
| 5,780,449 A | 7/1998 | Bracht et al. |
| 5,780,610 A | 7/1998 | Collins et al. |
| 5,792,608 A | 8/1998 | Swaminathan et al. |
| 5,792,613 A | 8/1998 | Schmidt et al. |
| 5,807,718 A | 9/1998 | Joyce et al. |
| 5,814,476 A | 9/1998 | Kauffman et al. |
| 5,817,781 A | 10/1998 | Swaminathan et al. |
| 5,817,785 A | 10/1998 | Gold et al. |
| 5,830,653 A | 11/1998 | Froehler et al. |
| 5,839,443 A | 11/1998 | Rose et al. |
| 5,840,867 A | 11/1998 | Toole et al. |
| 5,859,221 A | 1/1999 | Cook et al. |
| 5,861,254 A | 1/1999 | Schneider et al. |
| 5,861,501 A | 1/1999 | Benseler et al. |
| 5,872,232 A | 2/1999 | Cook et al. |
| 5,879,917 A | 3/1999 | Essigmann et al. |
| 5,882,870 A | 3/1999 | Nadeau et al. |
| 5,882,941 A | 3/1999 | Essigman et al. |
| 5,891,689 A | 4/1999 | Takle et al. |
| 5,935,776 A | 8/1999 | Green et al. |
| 5,958,691 A | 9/1999 | Picken et al. |
| 5,989,823 A | 11/1999 | Jayasena et al. |
| 6,004,746 A | 12/1999 | Brent et al. |
| 6,051,388 A | 4/2000 | Bodenhamer |
| 6,054,274 A | 4/2000 | Sampson et al. |
| 6,060,056 A | 5/2000 | Coutts et al. |
| 6,093,555 A | 7/2000 | Dudycz et al. |
| 6,110,462 A | 8/2000 | Barbas et al. |
| 6,110,721 A | 8/2000 | Gibbs et al. |
| 6,111,095 A | 8/2000 | Benseler et al. |

(Continued)

FOREIGN PATENT DOCUMENTS

| | | |
|---|---|---|
| EP | 0769552 A1 | 4/1997 |
| EP | 1 026 243 | 8/2000 |

(Continued)

OTHER PUBLICATIONS

Declaration of Christopher P. Rusconi dated May 11, 2006 including Exhibit A.

Famulok, M., "Turning Aptamers into Anticoagulants: An RNA-Based Anticoagulant and Antidote are Effective at Controlling Blood Coagulation in Animals." Nature Biotechnology, 2004, pp. 1373-1374, vol. 22, No. 11.

Hicke, B. et al., "Escort Aptamers: A Delivery Service for Diagnosis and Therapy," Journal of Clinical Investigation, 2000, pp. 923-928, vol. 106, No. 8.

Osborne, S. et al., "Aptamers as Therapeutic and Diagnostic Reagents: Problems and Prospects," Current Opinion in Chemical Biology, 1997, pp. 5-9, vol. 1, No. 1.

(Continued)

*Primary Examiner* — Tracy Vivlemore
(74) *Attorney, Agent, or Firm* — King & Spalding

(57) ABSTRACT

The biological activity of nucleic acid ligand is regulated (i.e. enhanced or inhibited) in vivo to produce a desired biological effect. This is accomplished through the administration of a modulator, or regulator, that changes the binding of the nucleic acid ligand for its target or that degrades or otherwise cleaves, metabolizes or breaks down the nucleic acid ligand while the ligand is still exerting its effect. Modulators of the present invention can be administered in real time as needed based on various factors, including the progress of the patient, as well as the physician's discretion in how to achieve optimal therapy. Thus, this invention provides for the first time a regulatable therapeutic regime in the course of nucleic acid ligand therapy.

9 Claims, 28 Drawing Sheets

(56) References Cited

U.S. PATENT DOCUMENTS

| | | | |
|---|---|---|---|
| 6,114,038 | A | 9/2000 | Castro et al. |
| 6,120,997 | A | 9/2000 | Wong et al. |
| 6,127,119 | A | 10/2000 | Stephens et al. |
| 6,127,173 | A | 10/2000 | Eckstein et al. |
| 6,136,545 | A | 10/2000 | Hosel et al. |
| 6,147,204 | A | 11/2000 | Gold et al. |
| 6,150,461 | A | 11/2000 | Takei et al. |
| 6,153,410 | A | 11/2000 | Arnold et al. |
| 6,163,714 | A | 12/2000 | Stanley et al. |
| 6,171,795 | B1 | 1/2001 | Korman et al. |
| 6,177,263 | B1 | 1/2001 | Arnold et al. |
| 6,177,555 | B1 | 1/2001 | Jayasena et al. |
| 6,180,348 | B1 | 1/2001 | Li |
| 6,183,967 | B1 | 2/2001 | Jayasena et al. |
| 6,222,025 | B1 | 4/2001 | Cook et al. |
| 6,258,601 | B1 | 7/2001 | Monia et al. |
| 6,315,995 | B1 | 11/2001 | Pinsky |
| 6,316,403 | B1 | 11/2001 | Pinsky |
| 6,331,398 | B1 | 12/2001 | Gold et al. |
| 6,391,300 | B1 | 5/2002 | Rose |
| 6,531,584 | B1 | 3/2003 | Cook et al. |
| 2003/0175703 | A1 | 9/2003 | Sullenger et al. |
| 2006/0040881 | A1 | 2/2006 | Rusconi |
| 2006/0105980 | A1 | 5/2006 | Benedict et al. |

FOREIGN PATENT DOCUMENTS

| | | |
|---|---|---|
| JP | 8070899 | 3/1996 |
| JP | 11127864 | 5/1999 |
| WO | WO 92/14842 | 9/1992 |
| WO | WO 94/06811 | 3/1994 |
| WO | WO 94/08050 | 4/1994 |
| WO | WO 97/42317 | 11/1997 |
| WO | WO 99/33971 | 7/1999 |
| WO | WO 99/50462 | 10/1999 |
| WO | WO 00/20040 | 4/2000 |
| WO | WO 00/22114 | 4/2000 |
| WO | WO 00/24912 | 5/2000 |
| WO | WO 00/42063 | 7/2000 |
| WO | WO 00/42064 | 7/2000 |
| WO | WO 00/47774 | 8/2000 |
| WO | WO 01/27263 A1 | 4/2001 |
| WO | WO 02/26932 | 4/2002 |
| WO | WO 2004/011680 | 2/2004 |
| WO | WO 2004/014844 | 2/2004 |
| WO | WO 2004/047742 | 6/2004 |
| WO | WO 2004/050899 | 6/2004 |
| WO | WO 2005/010150 | 2/2005 |
| WO | WO 2005/014533 | 2/2005 |
| WO | WO 2005/052121 | 6/2005 |
| WO | WO 2005/084412 | 9/2005 |
| WO | WO 2005/106042 | 11/2005 |
| WO | WO 2005/111238 | 11/2005 |
| WO | WO 2006/029258 | 3/2006 |
| WO | WO 2006/033854 | 3/2006 |
| WO | WO 2008/121354 A1 | 10/2008 |

OTHER PUBLICATIONS

Rusconi, C. et al., "Antidote-Mediated Control of an Anticoagulant Aptamer in vivo," Nature Biotechnology, 2004, pp. 1423-1428, vol. 22, No. 11.
Rusconi, C. et al., "Blocking the Initiation of Coagulation by RNA Aptamers to Factor VIIA," Thrombosis and Haemostasis, 2000, pp. 841-848, vol. 85, No. 5.
White, R. et al., "Developing Aptamers into Therapeutics," Journal of Clinical Investigation, 2000, pp. 929-934, vol. 106, No. 8.
Agrawal et al., "Antisense therapeutics: is it as simple as complementary base recognition?" Molecular Medicine Today, 6:72-81 (2000).
Aldaz-Carroll et al, "Apical loop-internal loop interactions: a new RNA-RNA recognition motif identified through in vitro selection against RNA hairpins of hepatitis C virus mRNA", Biochemistry 41(18):5883-5893 (2002)—Abstract.
Biedenkapp, et al., "Viral myb oncogene encodes a sequence-specific DNA-binding activity," Nature, 335: 835-837 (1988).
Biesecker et al, "Derivation of RNA aptamer inhibitors of human complement C5," Immunopharmacology, 42(1-3):219-230 (1999)—Abstract.
Boiziau et al.,"DNA Aptamers Selected Against the HIV-1 trans-Activation-responsive RNA element form RNA-DNA Kissing Complexes," J Biol. Chem., 274(18):12730-12737 (1999).
Burke, et al., "A novel axidophilic RNA motif that recognizes Coenzyme A," Biochemistry, p. 4653-4663 (Nov. 25, 1997) (abst.).
Callas et al, "Comparative pharmaceology of site directd antithrombin agents. Implication in drug development," Thrombosis and Haemostasis,74(1):473-481 (1995)—Abstract.
Charlton et al, "In vivo imaging of inflammation using an aptamer inhibitor of human neutrophil elastase", Chemistry & Biology, 4(11):809-816 (1997)—Abstract.
Collin et al., "NMR characterization of a kissing complex formed between the TAR RNA element of HIV-1 and a DNA aptamer," Nucleic Acids Research, 28(17):3386-3391 (2000).
Darfeuille et al., "RNA and N3'→P5' kissing aptamers targeted to the trans-activation responsive (TAR) RNA of the human immunodeficiency virus-1," Nucleosides Nucleotides Nucleic Acids, 20(4-7):441-449 (2001)—Abstract.
Duconge & Toulme, "In vitro selection identifies key determinants for loop-loop interactions: RNA aptamers selective for the TAR RNA element of HIV-1," RNA 5(12):1605-1614 (1999)—Abstract.
Duconge et al., "Is a Closing "GA PAIR" a Rule for Stable Loop-Loop RNA Complexes?" J Biol. Chem., 275(28):21287-21294 (2000).
Gal et al, "Selection of a RNA aptamer that binds to human activated protein C and inhibits its protease function", European Journal of Biochemistry, 252(3):553-562 (1998)—Abstract.
Hwang et al, "Inhibition of gene expression in human cells through small molecule-RNA interactions," PNAS, 96(23):12997 (1999).
Jen et al., "Suppression of gene expression by targeted disruption of messenger RNA: available options and strategies," Stem Cells, 18:307-319 (2000).
Kinzler & Vogelstein, "Whole genome PCR: application to the identification of sequences bound by gene regulatory proteins," Nuc. Acids Rsch., 17: 3645 (1989).
Leclerc, et al. "A three dimensional model of the Rev-binding element of HIV—a derived from analyses of apramers," Nat. Struct. Biol., 1:293-300 (abst) (1994).
Leva et al, "GnRH Binding RNA and DNA Spiegelmers" A Novel Approach toward GnRH Antagonism, Chemistry & Biology, 8:351-359 (2002).
Li et al, "A novel nucleotide-based thrombin inhibitor inhibits clot-bound thrombin and reduces arterial platelet thrombus formation," Blood, 83(3):677-682 (1994)—Abstract.
Oliphant et al., "Defining the sequence specificity of DNA-binding proteins by selecting binding sites from random-sequence oligonucleotides: analysis of yeast GCN4 protein," Mol. Cell. Bio., 9:2944-2949 (1989).
Opalinska et al., "Nucleic-acid therapeutics: basic principles and recent applications," Nature Reviews Drug Discovery, 1:503-514 (2002).
Padmanabhan et al, "The structure of alpha-thrombin inhibited by a 15-mer single-stranded DNA aptamer," Journal of Biological Chemistry, 268(24): 17651-17654 (1993)—Abstract.
Robertson & Joyce, "Selection in vitro of an RNA enzyme that specifically cleaves single-stranded DNA," Nature, 344: 467-468 (1990).
Rusconi et al, "RNA aptamers as reversible antagonists of coagulation factor 1xa," Nature, 419:90-94(2002).
Shaw et al, "A novel oligodeoxynucleotide inhibitor of thrombin. I. In vitro metabolic stability in plasma and serum," Pharmaceutical Research, 12(12):1937-1942 (1995)—Abstract.
Sheehan & Lan, "Phosophothioate Oligonucleotides Inhibit the Intrinsic Tenase Complex," Blood, 92(5); 1617-1625 (1998).
Tasset et al, "Oligonucleotide inhibitors of human thrombin that bind distinct epitopes," Journal of molecular biology, 272(5):688-698 (1997)—Abstract.
Tinevez et al, "Selective inhibition of cell-free translation by oligonucleotides targeted to a mRNA hairpin structure," Nucleic Acids Research, 26(10):2273-2278 (1998).

(56) References Cited

OTHER PUBLICATIONS

Tucker et al, "Detection and plasma pharmacokinetics of an anti-vascular endothelial growth factor oligonucleotide-aptamer in (NX1838) rhesus monkeys," *Journal of Chromatography*, 732(1):203-212 (1999)—Abstract.

Wahlestedt et al, "Potent and nontoxic antisense oligonucleotides containing locked nucleic acids," *Proc. Natl. Acad. Sci.*, USA 97(10):5633-5638 (2000).

Werstuck et al, "Controlling Gene Expression in Living Cells Through Small Molecule-RNA Interactions," *Science*, 282:296 (1998).

Williams et al, "Bioactive and nuclease-resistant L-DNA ligand of vasopressin," *Proc. Natl. Acad. Sci.*, USA 94:11285-11290 (1997).

Becker et al., "Antidote-controlled antithrombotic therapy targeting factor IXa and von Willebrand factor", Oligonucleotide Therapeutics, vol. 1175, pp. 61-70 (2009).

Blake et al., "A reversible apterner improves outcome and safety in murine models of stroke and hemorrhage", Oligonucleotides, vol. 21, pp. 11-19 (2011).

FIXa Aptamers

| | S1 | L1 | S2 | L2 | S2 | L3 | S1 | |
|---|---|---|---|---|---|---|---|---|
| 9.3 | gggaugggGA | CUAUACC | GCG | UAAUGC | UGC | C | UCCCCAUUCC | |
| 9.20 | gggGA | CUAUACCGGCA | | AUCG | UGC | A | UCCCC | |
| 9.19 | ugggA | CCAUA | ACGA | CUAC | UCGU | GAA | UCCCA | |
| 9.4 | ugggCA | CUAUAC | GCA | UCU | UGC | | UCCCA | |
| 9.12 | uggg | CGAUA | UAC | ACAUUG | GUG | | UGCCUG | |
| 9.17 | gggA | CCAUAC | GCA | CAU | UGC | AU | CCCA | |
| 9.11 | ugggA | CUAUA | UUCGG | AAU | CUGGA | UGAA | UCCC | |
| 9.2 | gggauggg | CUAUAUA | CAC | GCUG | GUG | C | UCCCA | |
| 9.7 | ggauggg | CGAUA | ACCA | ACA | UGGU | AU | CCCAUCUC | |
| 9.16 | uggg | CCAUA | CGU | GG | ACG | GAU | CCCAUUC | |
| 9.18 | uggg | CCAUA | ACCA | CUU | UGGU | GAA | CCCG | |
| 9.28 | gggCG | CCAUAC | GCA | CAU | UGC | ACUGCA | CCCA | |
| 9.25 | ggGA | CCAUA | ACUC | UAAC | UGC | UGCAU | CGCCU | |
| 9.14 | gggGA | CUAUA | CGU | GAACG | GGGU | GAA | UCCC | |
| 9.27 | uggg | UAAUA | ACU | GUA | ACU | GCA | UCCAC | |
| 9.26 | ggg | UGAUA | ACCA | CUC | UGGU | UGAA | CCCA | |
| | | | | | | GAA | CCC | |

Aptamers:
9.3: SEQ ID NO: 2
9.19: SEQ ID NO: 4
9.12: SEQ ID NO: 6
9.11: SEQ ID NO: 8
9.7: SEQ ID NO: 10
9.18: SEQ ID NO: 12
9.25: SEQ ID NO: 14
9.27: SEQ ID NO: 16

9.20: SEQ ID NO: 3
9.4: SEQ ID NO: 5
9.17: SEQ ID NO: 7
9.2: SEQ ID NO: 9
9.16: SEQ ID NO: 11
9.28: SEQ ID NO: 13
9.14: SEQ ID NO: 15
9.26: SEQ ID NO: 17

FIG. 7

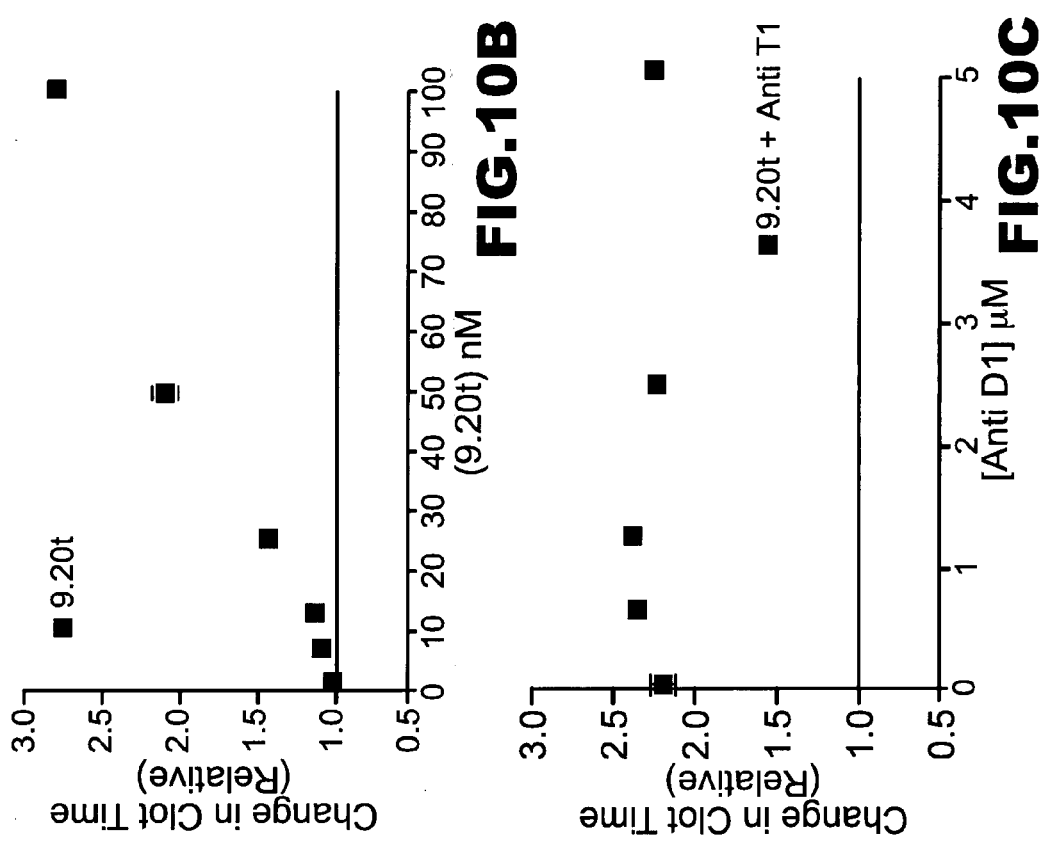
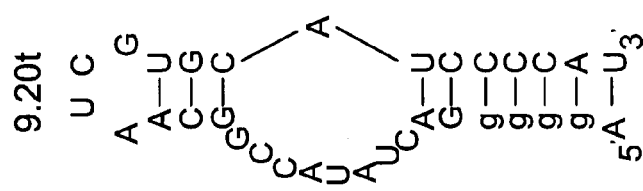
FIG. 10A
FIG. 10B
FIG. 10C

AS 3NT-1: 5' GAC AUG GGG AGG CAG CAU UA 3'
AS 3NT-2: 5' GAC AUG GGG AGG CAG CA 3'
AS 3NT-3: 5' GAC AUG GGG AGG CA 3'

Aptamer 11F7t (SEQ ID NO: 23)

Aptamer 11F7tM (SEQ ID NO: 24)

Aptamer 11F7t (SEQ ID NO: 23)

MODULATORS OF PHARMACOLOGICAL AGENTS

CROSS REFERENCE TO RELATED APPLICATIONS

This application is a continuation of U.S. application Ser. No. 10/155,233, filed May 28, 2002, now U.S. Pat. No. 7,300,922, which claims priority from U.S. Provisional Application No. 60/293,231, filed May 25, 2001 and U.S. Provisional Application No. 60/331,037, filed Nov. 7, 2001, the entire contents of which are is incorporated herein by reference in their entirety.

STATEMENT REGARDING FEDERALLY SPONSORED RESEARCH

This invention was made with Government support under Grant No. NS65222 awarded by the National Institutes of Health. The Government has certain rights in the invention.

TECHNICAL FIELD

The present invention relates, in general, to an agent that modulates the pharmacological activity of a nucleic acid ligand (e.g., aptamer) and, in particular, to an agent that enhances or inhibits the activity of such a ligand. The invention further relates to a composition comprising such an agent and to a method of using these agents and compositions in medical therapeutic and diagnostic procedures.

BACKGROUND

Nucleic acids have conventionally been thought of as primarily playing an informational role in biological processes. Through a method known as Systematic Evolution of Ligands by EXponential enrichment, termed SELEX, it has become clear that nucleic acids have three dimensional structural diversity not unlike proteins. SELEX is a method for the in vitro synthesis and selection of nucleic acid molecules with highly specific binding to target molecules. The SELEX process was first described by Gold and Tuerk in U.S. patent application Ser. No. 07/536,428, filed Jun. 11, 1990, now U.S. Pat. No. 5,475,096, and thereafter in U.S. patent application Ser. No. 07/931,473, filed Aug. 17, 1992, entitled "Methods for Identifying Nucleic Acid Ligands", now U.S. Pat. No. 5,270,163 (see also WO 91/19813). See also Tuerk et al., Science 249:505-10 (1990).

Nucleic acid ligands or aptamers are nonencoding single-stranded nucleic acid (DNA or RNA) that have the property of binding specifically to a desired target compound or molecule, and that have sufficient capacity for forming a variety of two- and three-dimensional structures and sufficient chemical versatility available within their monomers to act as ligands (form specific binding pairs) with virtually any chemical compound, whether monomeric or polymeric. Molecules of any size or composition can serve as targets. The SELEX method involves selection from a mixture of candidate oligonucleotides and step-wise iterations of binding, partitioning and amplification, using the same general selection scheme, to achieve virtually any desired criterion of binding affinity and selectivity. Starting from a mixture of nucleic acids, preferably comprising segments of randomized sequences, the SELEX method includes steps of contacting the mixture with the target under conditions favorable for binding, partitioning unbound nucleic acids from those nucleic acids that have bound specifically to target molecules, dissociating the nucleic acid-target complexes, amplifying the nucleic acids dissociated from the nucleic acid-target complexes to yield a ligand-enriched mixture of nucleic acids, then reiterating the steps of binding, partitioning, dissociating and amplifying through as many cycles as desired to yield highly specific high affinity nucleic acid ligands to the target molecule.

Nucleic acid ligands possess a number of features that can render them useful as therapeutic agents. They can be made as relatively small (e.g., 8 kDa to 15 kDa) synthetic compounds and can be selected to possess high affinity and specificity for target molecules (equilibrium dissociation constants ranging from, for example, 0.05-10 nM). Aptamers embody both the affinity properties of monoclonal antibodies and single chain antibodies (scFv's) and the manufacturing ease similar to that of a small peptide. Initial studies demonstrated the in vitro use of aptamers for studying protein function, and more recent studies have confirmed the utility of these compounds for studying in vivo protein function (Floege et al, Am J Pathol 154:169-179 (1999), Ostendorf et al, J Clin Invest 104:913-923, (1999)). In addition, animal studies to date have shown that aptamers and compounds of similar composition are well tolerated, exhibit low or no immunogenicity, and are thus suitable for repeated administration as therapeutic compounds (Floege et al, Am J Pathol 154:169-179 (1999), Ostendorf et al, J Clin Invest 104:913-923 (1999), Griffin et al, Blood 81:3271-3276 (1993), Hicke et al, J Clin Invest 106:923-928 (2000)).

As synthetic compounds, site specific modifications (insertions or deletions) can be made to aptamers to rationally alter their bioavailability and mode of clearance. For example, it has been found that 2'-fluoro pyrimidine-modified aptamers in the 10 kDa to 12 kDa size range have a short circulating half-life (~10 minutes) following bolus intravenous administration but that simple chemical modification of the aptamer or conjugation of the aptamer to a high molecular weight inert carrier molecule (e.g., PEG) increases circulating half-life substantially (6-12 hours) (Willis et al, Bioconjug Chem 9:573-582 (1998), Tucker et al, J Chromatogr Biomed Sci Appl 732:203-212 (1999), Watson et al, Antisense Nucleic Acid Drug Dev 10:63-75 (2000)). Bioactive and nuclease resistant single-stranded nucleic acid ligands comprising L-nucleotides have been described (Williams et al, Proc. Natl. Acad. Sci. 94:11285 (1997); U.S. Pat. No. 5,780,221; Leva et al, Chem. Biol. 9:351 (2002)). These "L-aptamers" are reportedly stable under conditions in which aptamers comprising nucleotides of natural handedness (D-nucleotides) (that is, "D-aptamers") are subject to degradation.

A number of third parties have applied for and secured patents covering the identification, manufacture and use of aptamers. As stated above, Larry Gold and Craig Tuerk are generally credited with first developing the SELEX method for isolating aptamers, and their method is described in a number of United States patents including those mentioned above and U.S. Pat. Nos. 5,670,637, 5,696,249, 5,843,653, 6,110,900, and 5,270,163, as well as other described in the Detailed Description of the Invention. Thomas Bruice et al. reported a process for producing aptamers in U.S. Pat. No. 5,686,242, which differs from the original SELEX process reported by Tuerk and Gold because it employs strictly random oligonucleotides during the screening sequence. The oligonucleotides screened in the '242 patent process lack the oligonucleotide primers that are present in oligonucleotides screened in the SELEX process.

Several patents to Gold et al. relate to aptamers themselves. For example, U.S. Pat. No. 6,114,120 relates to an aptamer that binds to a cell macromolecule. U.S. Pat. No. 5,670,637 relates to aptamers that bind to proteins. U.S. Pat. No. 5,696,249 relates to an aptamer produced by the SELEX process.

Other patents have issued that are directed to aptamers against specific biological targets, and to the methods for identifying these aptamers. U.S. Pat. Nos. 5,756,291 and 5,582,981 to O'Toole, for example, disclose a method for detecting thrombin using a labeled aptamer that comprises a defined six nucleotide sequence. U.S. Pat. Nos. 5,527,894 and 5,637,461 of Gold et al. relate to methods of identifying aptamers against the tat protein. Other patents that disclose aptamers directed against specific biological targets include U.S. Pat. Nos. 5,496,938 (HIV-reverse transcriptase), 5,476,766 (thrombin), 5,459,015 (fibroblast growth factor), 5,472,841 (neutrophil elastase), 5,849,479 (vascular endothelial growth factor), 5,726,017 (HIV GAG), 5,731,144 (TGFβ), 5,827,456 (chorionic gonadotropin hormone), 5,780,228 (lectins), 5,766,853 (selectins), 5,674,685 (platelet derived growth factor), 5,763,173 (DNA polymerases), 6,140,490. (complement system proteins), and 5,869,641 (CD4).

Sullenger, Rusconi, Kontos and White in WO 0226932 A2 describe RNA aptamers that bind to coagulation factors, E2F family transcription factors, Ang1, Ang2, and fragments or peptides thereof, transcription factors, autoimmune antibodies and cell surface receptors useful in the modulation of hemostasis and other biologic events. (See also Rusconi et al, Thrombosis and Haemostasis 83:841-848 (2000), White et al, J. Clin Invest 106:929-34 (2000), Ishizaki et al, Nat Med 2:1386-1389 (1996), and Lee et al, Nat Biotechnol 15:41-45 (1997)).

A number of patents have also issued that relate to specific uses of aptamers. For example, Bruice et al. in U.S. Pat. No. 6,022,691 describe the use of aptamers identified by a SELEX-like process to detect drugs and other molecules in biological fluids. Gold et al. in U.S. Pat. No. 5,843,653 provide a diagnostic method using aptamers. U.S. Pat. No. 6,110,900 discloses a diagnostic composition that contains an aptamer. U.S. Pat. No. 5,789,163 discloses a sandwich assay that employs aptamers as the capture and/or detection ligand. U.S. Pat. No. 6,147,204 describes the use of aptamers/lipophile complexes to deliver therapeutic and diagnostic aptamers to intracellular locations in vivo. U.S. Pat. Nos. 5,705,337, 5,962,219, 5,763,595 and 5,998,142 disclose aptamers that are chemically modified to covalently bind to target proteins.

Several methods have been developed that modify the base SELEX process to obtain aptamers that satisfy objectives in addition to exhibiting high binding affinity toward a target molecule. For example, a number of patents disclose the use of modified nucleotides in the SELEX process to obtain aptamers that exhibit improved properties. U.S. Pat. No. 5,660,985, for example, relates to SELEX using 2'-modified nucleotides that display enhanced in vivo stability. U.S. Pat. No. 6,083,696 discloses a "blended" SELEX process in which oligonucleotides covalently linked to non-nucleic acid functional units are screened for their capacity to bind a target molecule. Other patents describe post-SELEX modifications to aptamers to decrease their size, increase their stability, or increase target binding affinity. See, e.g., U.S. Pat. Nos. 5,817,785 and 5,648,214.

Still other patents describe unique SELEX processes. For example, U.S. Pat. Nos. 5,763,566 and 6,114,120 disclose processes for generating aptamers using the SELEX process with whole biological tissue as the target, to identify aptamers that have binding affinity toward biological tissues and components thereof. U.S. Pat. No. 5,580,737 discloses a modification to the SELEX process that yields aptamers that can discriminate between two or more compounds. U.S. Pat. No. 5,567,588 discloses the "solution SELEX" method in which the nucleic acid candidate mixture is screened in solution in order to preferentially amplify the highest affinity aptamer.

Kauffman has obtained patents disclosing the generation of large libraries of proteins from large pools of stochastically generated oligonucleotide vectors. See U.S. Pat. Nos. 5,814,476 and 5,723,323.

Weis et al. disclose in U.S. Pat. No. 5,245,022 an oligonucleotide of about 12-25 bases that is terminally substituted by a polyalkyleneglycol. These modified oligonucleotides are reported to be resistant to exonuclease activity.

U.S. Pat. Nos. 5,670,633 and 6,005,087 to Cook et al. describe thermally stable 2'-fluoro oligonucleotides that are complementary to an RNA or DNA base sequence. U.S. Pat. Nos. 6,222,025 and 5,760,202 to Cook et al. describe the synthesis of 2'-O substituted pyrimidines and oligomers containing the modified pyrimidines. EP 0 593 901 B1 discloses oligonucleotide and ribozyme analogues with terminal 3',3'- and 5',5'-nucleoside bonds. U.S. Pat. No. 6,011,020 to Gold et al. discloses an aptamer modified by polyethylene glycol.

A number of U.S. patents have issued that describe methods of large scale manufacturing that can be used to produce aptamers. Caruthers et al., for example, describe in U.S. Pat. Nos. 4,973,679; 4,668,777; and 4,415,732 a class of phosphoramidite compounds that are useful in the manufacture of oligonucleotides. In another series of patents, Caruthers et al. disclose a method of synthesizing oligonucleotides using an inorganic polymer support. See, e.g., U.S. Pat. Nos. 4,500,707, 4,458,066 and 5,153,319. In still another series of patents, Caruthers et al. discloses a class of nucleoside phosphorodithioates that can be used to manufacture oligonucleotides. See, e.g., U.S. Pat. Nos. 5,278,302, 5,453,496 and 5,602,244. Reports of aptamers designed to bind to other aptamers include: Aldaz-Carroll L, Tallet B, Dausse E, Yurchenko L, Toulme J J.; Apical loop-internal loop interactions: a new RNA-RNA recognition motif identified through in vitro selection against RNA hairpins of the hepatitis C virus mRNA; Biochemistry. 2002 May 7; 41(18):5883-93; Darfeuille F, Cazenave C, Gryaznov S, Duconge F, Di Primo C, Toulme J J.; RNA and N3'->P5' kissing aptamers targeted to the trans-activation responsive (TAR) RNA of the human immunodeficiency virus-1, Nucleosides Nucleotides Nucleic Acids. 2001 April-July; 20(4-7):441-9; Collin D, van Heijenoort C, Boiziau C, Toulme J J, Guittet E., NMR characterization of a kissing complex formed between the TAR RNA element of HIV-1 and a DNA aptamer. Nucleic Acids Res. 2000 Sep. 1; 28(17):3386-91; Duconge F, Di Primo C, Toulme J J., Is a closing "GA pair" a rule for stable loop-loop RNA complexes? J Biol. Chem. 2000 Jul. 14; 275(28):21287-94.; Duconge F, Toulme J J. In vitro selection identifies key determinants for loop-loop interactions: RNA aptamers selective for the TAR RNA element of HIV-1. RNA. 1999 December; 5(12): 1605-14; Boiziau C, Dausse E, Yurchenko L, Toulme J J., DNA aptamers selected against the HIV-1 trans-activation-responsive RNA element form RNA-DNA kissing complexes; J Biol Chem. 1999 Apr. 30; 274(18): 12730-7; and Le Tinevez R, Mishra R K, Toulme J J., Selective inhibition of cell-free translation by oligonucleotides targeted to a mRNA hairpin structure; Nucleic Acids Res. 1998 May 15; 26(10):2273-8.

Currently, many drugs elicit medical complications such as side effects and undesirable or uncontrollable outcomes. Treating medical complications that result from side effects leads to additional healthcare costs. The recent identification of this range of nucleic acid ligands useful in medical therapy has opened new avenues of research and development. While progress has been made in this area, a strong need remains to provide methods and compositions to improve the manner in which these ligands are used and to increase their efficacy, to better control the process of therapy, and to provide therapies that have decreased side effects over traditional therapeutic methods. The present invention provides compounds, compositions and methods to improve the process of using nucleic acid ligands in medical therapy. The approach provided by the present invention allows for more control over the therapeutic effect, pharmacokinetics and duration of activity of nucleic acid ligands.

SUMMARY OF THE INVENTION

It has been discovered that the biological activity of nucleic acid ligands can be modulated (i.e., enhanced or inhibited) in vivo to produce a desired biological effect. This can be accomplished through the administration of a modulator, or regulator, that changes the binding of the nucleic acid ligand for its target or that degrades or otherwise cleaves, metabolizes or breaks down the nucleic acid ligand while the ligand is still exerting its effect. Modulators of the present invention can be administered in real time as needed based on various factors, including the progress of the patient, as well as the physician's discretion in how to achieve optimal therapy. Thus, this invention provides for the first time a regulatable therapeutic regime in the course of nucleic acid ligand therapy.

This regulatable therapeutic regime controls drug action by introducing a modulator that is easy to use, can be independent of the patient's health status, has a uniform mode of action, and does not require continuous drug infusion. In one example, an antidote is provided that is rationally designed to turn off aptamer activity when desired by the physician.

The modulator can be a oligonucleotide, a small molecule, a peptide, oligosaccharide, for example an aminoglycoside, or other molecule that can bind to or otherwise modulate the activity of the therapeutic nucleic acid ligand, including a small molecule, or a chimera or fusion or linked product of any of these. For example, the modulator can be an oligonucleotide that is complementary to at least a portion of the nucleic acid ligand. In another embodiment, the modulator can be a ribozyme or DNAzyme that targets the nucleic acid ligand. In a further embodiment, the modulator can be a peptide nucleic acid (PNA), morpholino nucleic acid (MNA), locked nucleic acid (LNA) or pseudocyclic oligonucleobases (PCO) that includes a sequence that is complementary to or hybridizes with at least a portion of the nucleic acid ligand. A typical nucleic acid ligand (e.g., aptamer) possesses some amount of secondary structure—its active tertiary structure is dependent on formation of the appropriate stable secondary structure. Therefore, while the mechanism of formation of a duplex between a complementary oligonucleotide modulator of the invention and a nucleic acid ligand is the same as between two short linear oligoribonucleotides, both the rules for designing such interactions and the kinetics of formation of such a product are impacted by the intramolecular aptamer structure. The rate of nucleation is important for formation of the final stable duplex, and the rate of this step is greatly enhanced by targeting the oligonucleotide modulator to single-stranded loops and/or single-stranded 3' or 5' tails present in the nucleic acid ligand. For the formation of the intermolecular duplex to occur, the free energy of formation of the intermolecular duplex has to be favorable with respect to formation of the existing intramolecular duplexes within the targeted nucleic acid ligand.

In an alternative embodiment of the invention, the modulator itself is an aptamer. In this embodiment, a nucleic acid ligand is first generated that binds to the desired therapeutic target. In a second step, a second nucleic acid ligand that binds to the first nucleic acid ligand is generated using the SELEX process described herein or other process, and modulates the interaction between the therapeutic nucleic acid ligand and the target. In one embodiment, the second nucleic acid ligand deactivates the effect of the first nucleic acid ligand.

In other alternative embodiments, the aptamer which binds to the target can be a PNA, MNA, LNA or PCO and the modulator is a nucleic acid ligand. Alternatively, the aptamer which binds to the target is a PNA, MNA, LNA or PCO, and the modulator is a PNA. Alternatively, the aptamer which binds to the target is a PNA, MNA, LNA or PCO, and the modulator is an MNA. Alternatively, the aptamer which binds to the target is a PNA, MNA, LNA or PCO, and the modulator is an LNA. Alternatively, the aptamer which binds to the target is a PNA, MNA, LNA or PCO, and the modulator is a PCO. Any of these can be used, as desired, in the naturally occurring stereochemistry or in non-naturally occurring stereochemistry or a mixture thereof. For example, in a preferred embodiment, the nucleic acid ligand is in the D configuration, and in an alternative embodiment, the nucleic acid ligand is in the L configuration.

The present invention also provides methods to identify the modulators of nucleic acid ligands. Modulators can be identified in general, through binding assays, molecular modeling, or in vivo or in vitro assays that measure the modification of biological function. In one embodiment, the binding of a modulator to a nucleic acid is determined by a gel shift assay. In another embodiment, the binding of a modulator to a nucleic acid ligand is determined by a Biacore assay. Other appropriate assays are described in the Detailed Description of the Invention.

In another embodiment, the binding or interaction of the modulator with the nucleic acid ligand is measured by evaluating the effect of the nucleic acid ligand with and without the modulator under appropriate biological conditions. As an example, modulators of the invention can be identified which regulate antithrombotic and anticoagulant aptamers. Modulator efficacy can be assessed in vitro or in vivo through a coagulation test bioassay such as the activated coagulation time test, the activated partial thromboplastin test, the bleeding time test, the prothrombin time test, or the thrombin clotting time test. Using an identified regime, a patient can be administered an anticoagulant nucleic acid ligand and then given the antidote when the time is appropriate to resume normal clotting action. This regime is useful, for example, during cardiovascular and vascular surgery, percutaneous coronary interventions (angioplasty), orthopedic surgery, and treatment of acute myocardial infarction. In a non-limiting, illustrative example, modulators of the present invention can bind to nucleic acid ligands that target tissue factor (TF)/factor VIIa (FVIIa), factor VIIIa (FVIIIa)/factor IXa (FIXa), factor Va (FVa/factor Xa (Fxa) enzyme complexes and platelet receptors such as gp IIbIIIa and gp IbIX and modulate the effects of the nucleic acid ligand. This invention also provides antidote controlled platelet inhibitors, antithrombotics and fibrinolytics.

In one embodiment, the modulator is an oligonucleotide that binds to a Factor IXa aptamer (for example, Aptamer 9.3 or Aptamer 9.3t) that targets Coagulation Factor IXa. The antidote oligonucleotide can be complementary to at least a portion of the Factor IXa aptamer. Specifically, the antidote 2'-O-methyl oligonucleotide can consist of the following sequence, 5'AUGGGGAGGCAGCAUUA3' (SEQ ID NO: 25), 5'CAUGGGGAGGCAGCAUUA3' (SEQ ID NO: 26), 5'CAUGGGGAGGCAGCA3' (SEQ ID NO: 27), 5'CAUGGGGAGGCA3' (SEQ ID NO: 28), 5'GCA-UUACGCGGUAUAGUCCCCUA3' (SEQ ID NO: 29), 5'CGCGGUAUAGUCCCCUA3' (SEQ ID NO: 30). Modifications or derivatives thereof wherein a desired degree of hybridization is maintained.

In another embodiment, the modulator is an oligonucleotide that binds to a Factor Xa aptamer (for example, Aptamer 11F7t) that targets Coagulation Factor Xa. The antidote oligonucleotide can be complementary to at least a portion of the Factor Xa aptamer. Specifically, the antidote oligonucleotide may consist of the following sequences, 5'CUCGCUGGGGCUCUC3' (SEQ ID NO: 31), 5'UAUUAUCUCGCUGGG3' (SEQ ID NO: 32), 5'AAGAGCGGGGCCAAG3' (SEQ ID NO: 33), 5'GGGC-CAAGUAUUAU3' (SEQ ID NO: 34), 5'CAA-GAGCGGGGCCAAG 3' (SEQ ID NO: 35), 5'CGAGUA-UUAUCUUG3' (SEQ ID NO: 36) or any modification or derivative thereof wherein a desired degree of hybridization is maintained.

In another embodiment, the oligonucleotide modulators include nucleic acid sequences that are substantially homologous to and that have substantially the same ability to bind nucleic acid ligands, as the oligonucleotide modulators identified herein.

In a further embodiment, modulators of the invention can also be used to reverse the immunosuppressive effect of nucleic acid ligands that target interleukin, for example, in patients subject to infection. The present modulators can be used to reverse the immunostimulatory effects of nucleic acid ligands that target CTLA4 in patients at risk of developing autoimmunity.

In a further embodiment, modulators of the invention can be used to reverse the effects of aptamers that target growth factors (e.g., PDGF or VEGF). Such nucleic acid ligands can be used in the treatment of tumors and in the treatment of inflammatory proliferative diseases. Since growth factors play systemic roles in normal cell survival and proliferation, nucleic acid ligand treatment can result in a breakdown of healthy tissue if not tightly regulated (e.g., patients receiving nucleic acid ligands that target angiopoietin I can be subject to hemorrhaging). Modulators of the invention that target such nucleic acid ligands can be used to provide the necessary regulation.

Modulators of the invention can be used to reverse the effects of nucleic acid ligands that target receptors involved in the transmission of the nerve impulse at the neuromuscular junction of skeletal muscle and/or autonomic ganglia (e.g., nicotinic acetylcholine or nicotinic cholinergic receptors). Such nucleic acid ligands can be made to produce muscular relaxation or paralysis during anesthesia. Agents that block the activity of acetylcholine receptors (agents that engender neuromuscular blockade) are commonly used during surgical procedures, and it is preferred that the patients regain muscular function as soon as possible after the surgical procedure is complete to reduce complications and improve patient turnover in the operating arenas. Therefore, much effort has been made to generate agents with predictable pharmacokinetics to match the duration of the drug activity to the anticipated duration of the surgical procedure. Alternatively, modulators of the invention that target such nucleic acid ligands can be used to provide the desired control of the activity of the neuromuscular blocker, and thus reduce the dependence on the patient's physiology to provide reversal of the neuromuscular blocking agent.

In a still further embodiment, modulators of the invention can be used to reverse the effect of nucleic acid ligands that target small molecules, such as glucose. Hypoglycemia can be avoided in patients receiving glucose-targeted nucleic acid ligands to regulate glucose uptake using the modulators of the invention.

Further, modulators can also be used to regulate the activity of nucleic acid ligands directed against members of the E2F family, certain of which are pro-proliferative, certain of which are repressive. The modulators of the invention can be used to "turn on" and "turn off" such nucleic acid ligands at desired points in the cell cycle.

In another embodiment, modulators of the invention can also be used to reverse the binding of nucleic acid ligands bearing radioactive or cytotoxic moieties to target tissue (e.g., neoplastic tissue) and thereby, for example, facilitate clearance of such moieties from a patient's system. Similarly, the modulators of the invention can be used to reverse the binding of nucleic acid ligands labeled with detectable moieties (used, for example, in imaging or cell isolation or sorting) to target cells or tissues (Hicke et al. J. Clin. Invest. 106:923 (2000); Ringquist et al, Cytometry 33:394 (1998)). This reversal can be used to expedite clearance of the detectable moiety from a patient's system.

Modulators of the invention can also be used in in vitro settings to enhance or inhibit the effect of a nucleic acid ligand (e.g., aptamer) on a target molecule. For example, modulators of the invention can be used in target validation studies. Using modulators of the invention, it is possible to confirm that a response observed after inhibiting a target molecule (with a nucleic acid ligand) is due to specifically inhibiting that molecule.

The modulators of the invention can be formulated into pharmaceutical compositions that can include, in addition to the modulator, a pharmaceutically acceptable carrier, diluent or excipient. The precise nature of the composition will depend, at least in part, on the nature of the modulator and the route of administration. Optimum dosing regimens can be readily established by one skilled in the art and can vary with the modulator, the patient and the effect sought. Generally, the modulator can be administered IV, IM, IP, SC, or topically, as appropriate.

Alternatively, and in view of the specificity of the modulators of the invention, subsequent treatment can involve the administration of additional nucleic acid ligands that are either the same or different as the original nucleic acid ligand/antidote oligonucleotide pair first administered.

Finally, one optional embodiment of the invention is the identification and selection of modulators and regulators that exhibit relevant species cross-reactivity to increase usefulness of preclinical animal studies.

Objects and advantages of the present invention will be clear from the description that follows:

BRIEF DESCRIPTION OF THE DRAWINGS

FIG. 5A. Cholesterol addition has a modest effect on the affinity of aptamer 9.3t-C for FIXa. A competition binding assay is used to measure affinity of 9.3t-C for FIXa. FIG. 5B. In vitro anti-coagulant activity of aptamer 9.3t-C in human plasma. FIG. 5C. In vitro anticoagulant activity of aptamer 9.3t-C in pig plasma.

FIG. 6A. In vivo anticoagulant activity of aptamer 9.3t-C in pigs following IV bolus injection, ACT assays (dotted line is 9.3t ACT data at 0.5 mg/ml from FIG. 3). FIG. 6B. In vivo anticoagulant activity of aptamer 9.3t-C in pigs following IV bolus injection, APTT and PT assays (0.5 mg/kg 9.3t from FIG. 4). FIG. 6C. In vivo plasma concentration of 9.3t-C versus 9.3t over time following bolus IV injection. Concentrations were calculated by interpolation from in vitro dose response curves of APTT assays for each aptamer.

FIG. 7 shows alignment of minimal FIXa aptamers (SEQ ID NO:2-SEQ ID NO: 17). Sequences in lower case letters are derived from the fixed region of the library used in the SELEX process and sequences in upper case letters are derived from the random region of the library used in the SELEX process. S=stem, L=loop.

FIG. 8 shows the native gel analysis of binding of antidote oligonucleotide to aptamer 9.3t. The ability of the antidote oligonucleotide to bind to and denature aptamer 9.3t was evaluated by native gel electrophoresis. Briefly, radiolabeled 9.3t (125 nM) was incubated at 37° C. for 15 minutes with (from left to right) an 8 fold, 4 fold, 2 fold molar excess or equimolar amounts of the antidote (A.S.) or nonsense oligonucleotide (N.S.). Native 9.3t migrates faster than antidote bound 9.3t in this gel system (compare lanes 1 and 2).

FIG. 9A. Change in clot time versus antidote or nonsense oligonucleotide concentration. A value of 1.0 indicates no change in clot time over the baseline value. 9.3tM is a mutant version of aptamer 9.3t that has no anticoagulant activity. FIG. 9B. Fraction of the anticoagulant activity of aptamer 9.3t reversed versus the molar excess of antidote oligonucleotide.

FIG. 10A-10C show the specificity of oligonucleotide antidotes. FIG. 10A. Minimal secondary structure of aptamer 9.20t (SEQ ID NO: 18). FIG. 10B Anticoagulant activity of 9.20t. FIG. 10C. Specificity of antidote oligonucleotide Anti D1.

FIG. 12A. Competitive binding data. FIG. 12B. In vitro anticoagulant data.

FIG. 13A. Reversal of anticoagulant activity vs. concentration of antidote oligonucleotide. FIG. 13B. Reversal of anticoagulant activity vs. molar excess of antidote over aptamer.

FIG. 18A. Predicted secondary structure of aptamer 11F7t (SEQ ID NO:23), which binds human coagulation factor Xa with a $K_D$ of ~1.5 nM. FIG. 18B. Predicted secondary structure of a mutant version of aptamer 11F7t, termed 11F7tM (SEQ ID NO:24).

FIG. 21A. The antidote oligonucleotides effectively reverse the activity of aptamer 11F7t in human plasma. FIG. 21B. Characterization of antidote 5-2 activity over a larger concentration range of antidote 5-2, and comparison to the antidote activity of a scrambled sequence version of antidote 5-2, 5-2 scr.

FIGS. 25A-25C. The activity of aptamer Peg-9.3t and antidote 5-2 were tested in plasma from hemodialysis-dependent patients diagnosed with HIT. FIG. 25D-25F. The activity of aptamer Peg-9.3t and antidote 5-2 were tested in plasma from patients suffering from thromboembolic complications of HIT. Plasma samples were treated as indicated: aptamer, 125 nM Peg-9.3t; antidote, 1.25 μM AO 5-2; mutant aptamer, 125 nM 9.3tM. Experiments were performed as described in Example 2, FIG. 9. Data is reported in seconds (s) and is the average ± range of duplicate measurements.

DETAILED DESCRIPTION OF THE INVENTION

Figure 1:
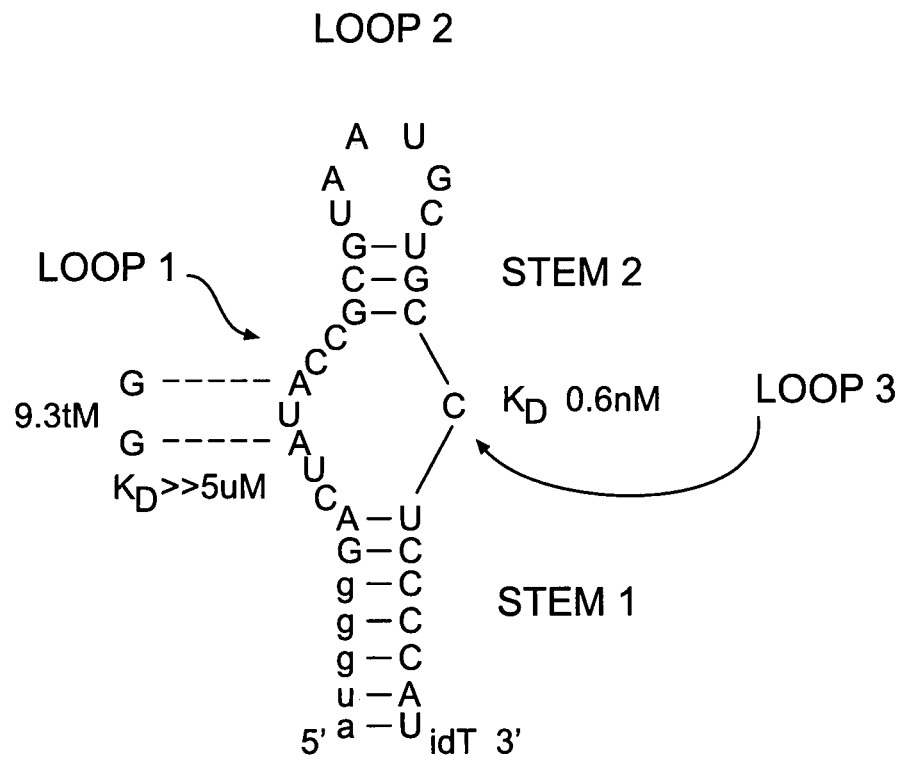
FIG. 1 shows the FIXa aptamer 9.3t (SEQ ID NO: 1). All purines are 2'-hydroxyl and all pyrimidines are 2'-fluoro nucleotides.

The present invention relates generally to modulators of pharmacological agents, including therapeutic and diagnostic agents. The invention further relates to methods of enhancing or inhibiting the efficacy of pharmacological agents by administering modulators of the invention to a subject (e.g., a human) in need thereof. Additionally, the invention relates to methods of using modulators of the invention to assess the activity of nucleic acid ligands, in vivo and in vitro.

The present invention relates to a method of modulating the activity of a nucleic acid ligand, for example, by altering its conformation and thus its function. In accordance with the invention, the modulator can be contacted with the targeted nucleic acid ligand under conditions such that it binds to the nucleic acid ligand and modifies the interaction between the nucleic acid ligand and its target molecule. Modification of that interaction can result from modification of the nucleic acid ligand structure as a result of binding by the modulator. The modulator can bind the free nucleic acid ligand and/or the nucleic acid ligand bound to its target molecule.

Modulators of the invention can be designed so as to bind any particular nucleic acid ligand with a high degree of specificity and a desired degree of affinity. Modulators can be also be designed so that, upon binding, the structure of the nucleic acid ligand is modified to either a more or less active form. For example, the modulator can be designed so that upon binding to the targeted nucleic acid ligand, the three-dimensional structure of that nucleic acid ligand is altered such that the nucleic acid ligand can no longer bind to its target molecule or binds to its target molecule with less affinity.

Alternatively, the modulator can be designed so that, upon binding, the three dimensional structure of the nucleic acid ligand is altered so that the affinity of the nucleic acid ligand for its target molecule is enhanced. That is, the modulator can be designed so that, upon binding, a structural motif is produced in the nucleic acid ligand so that the nucleic acid ligand can bind to its target molecule.

In one embodiment, the modulator is an oligonucleotide. The oligonucleotide can be a sequence that is complementary to at least a portion of the nucleic acid ligand. In another embodiment, the modulator is a ribozyme or DNAzyme that targets the nucleic acid ligand. In a further embodiment, the modulator can be, for example, a peptide nucleic acid or morpholino nucleic acid that includes a sequence that is complementary to or hybridizes with at least a portion of the nucleic acid ligand. A modulator is specifically hybridizable with the nucleic acid ligand when binding of the modulator to the nucleic acid ligand sufficiently interferes with the normal function of the nucleic acid ligand to cause a change in the biological activity of the nucleic acid ligand, under physiological conditions. In an alternative embodiment, there is a sufficient degree of non-Watson Crick binding of the modulator to the nucleic acid ligand to affect the activity of the nucleic acid ligand.

In a still further embodiment, the modulator is nucleic acid binding peptide, polypeptide or protein that binds to or otherwise interacts with the nucleic acid ligand. In a further embodiment, the modulator is an oligosaccharide that binds the nucleic acid ligand. In a specific embodiment, the modulator is an aminoglycoside. In another embodiment, the modulator is a small organic molecule (i.e., a molecule that can be synthetic or naturally occurring that is not otherwise found in vivo and typically has a molecular weight of less than 1000).

The present invention also includes methods for identifying modulators of nucleic acid ligands. In one embodiment, the binding of a modulator to a nucleic acid is determined by any assay that measures binding affinity, such as a gel shift assay. In another embodiment, the binding of a modulator to a nucleic acid ligand is determined by a Biacore assay. Other exemplary assays are described below.

In another embodiment, the binding or interaction of the modulator with the nucleic acid ligand is measured by evaluating the effect of the ligand with and without the regulator under appropriate biological conditions. For example, modulators can be identified that modify the antithrombotic or anticoagulant activity of nucleic acid ligand in vitro or in vivo through a coagulation test bioassay such as an activated coagulation time test, the activated partial thromboplastin test, the bleeding time test, the prothrombin time test, or the thrombin clotting time test.

The present invention further includes the use of such modulators in a variety of indications whereby control of nucleic acid ligand activity is desired. The modulators may act to inhibit nucleic acid ligand activity as an antidote to reverse the actions of the nucleic acid ligand. Additionally, the invention provides methods of using modulators of the invention to assess the activity of nucleic acid ligands. The invention is also directed to methods of enhancing or inhibiting the efficacy of nucleic acid ligands by administering modulators of the invention to human or non-human mammals.

In a further embodiment, modulators of the invention can also be used to reverse the immunosuppressive effect of nucleic acid ligands that target interleukin, for example, in patients subject to infection. The present modulators can be used to reverse the immunostimulatory effects of nucleic acid ligands that target CTLA4 in patients at risk of developing autoimmunity.

In a further embodiment, modulators of the invention can be used to reverse the effects of nucleic acid ligands that target growth factors (e.g., PDGF or VEGF). Such nucleic acid ligands can be used in the treatment of tumors and in the treatment of inflammatory proliferative diseases. Since growth factors play systemic roles in normal cell survival and proliferation, nucleic acid ligand treatment can result in a breakdown of healthy tissue if not tightly regulated (e.g., patients receiving nucleic acid ligands that target angiopoietin I can be subject to hemorrhaging). Modulators of the invention that target such nucleic acid ligands can be used to provide the necessary regulation.

Modulators of the invention can be used to reverse the effects of nucleic acid ligands that target receptors involved in the transmission of the nerve impulse at the neuromuscular junction of skeletal muscle and/or autonomic ganglia (e.g., nicotinic acetylcholine or nicotinic cholinergic receptors).

Such nucleic acid ligands can be made to produce muscular relaxation or paralysis during anesthesia. Agents that block the activity of acetylcholine receptors (agents that engender neuromuscular blockade) are commonly used during surgical procedures, and it is preferred that the patients regain muscular function as soon as possible after the surgical procedure is complete to reduce complications and improve patient turnover in the operating arenas. Therefore, much effort has been made to generate agents with predictable pharmacokinetics to match the duration of the drug activity to the anticipated duration of the surgical procedure. Alternatively, modulators of the invention that target such nucleic acid ligands can be used to provide the desired control of the activity of the neuromuscular blocker, and thus reduce the dependence on the patient's physiology to provide reversal of the neuromuscular blocking agent.

In a still further embodiment, modulators of the invention can be used to reverse the effect of nucleic acid ligands that target small molecules, such as glucose. Hypoglycemia can be avoided in patients receiving glucose-targeted nucleic acid ligands to regulate glucose uptake using the modulators of the invention.

Further, modulators can also be used to regulate the activity of nucleic acid ligands directed against members of the E2F family, certain of which are pro-proliferative, certain of which are repressive. The modulators of the invention can be used to "turn on" and "turn off" such nucleic acid ligands at desired points in the cell cycle.

In another embodiment, modulators of the invention can also be used to reverse the binding of nucleic acid ligands bearing radioactive or cytotoxic moities to target tissue (e.g., neoplastic tissue) and thereby, for example, facilitate clearance of such moeity's from a patient's system. Similarly, the modulators of the invention can be used to reverse the binding of nucleic acid ligands labeled with detectable moieties (used, for example, in imaging or cell isolation or sorting) to target cells or tissues (Hicke et al. J. Clin. Invest. 106:923 (2000); Ringquist et al, Cytometry 33:394 (1998)). This reversal can be used to expedite clearance of the detectable moiety from a patient's system.

Modulators of the invention can also be used in in vitro settings to enhance or inhibit the effect of a nucleic acid ligand (e.g., aptamer) on a target molecule. For example, modulators of the invention can be used in target validation studies. Using modulators of the invention, it is possible to confirm that a response observed after inhibiting a target molecule (with a nucleic acid ligand) is due to specifically inhibiting that molecule.

The modulators of the invention can be formulated into pharmaceutical compositions that can include, in addition to the modulator, a pharmaceutically acceptable carrier, diluent or excipient. The precise nature of the composition will depend, at least in part, on the nature of the modulator and the route of administration. Optimum dosing regimens can be readily established by one skilled in the art and can vary with the modulator, the patient and the effect sought. Generally, the modulator is administered IV, IM, IP, SC, orally or topically, as appropriate.

In another embodiment, the nucleic acid ligand or its regulator can be covalently attached to a lipophilic compound such as cholesterol, dialkyl glycerol, diacyl glycerol, or a non-immunogenic, high molecular weight compound or polymer such as polyethylene glycol (PEG). In these cases, the pharmacokinetic properties of the nucleic acid ligand or modulator can be enhanced. In still other embodiments, the nucleic acid ligand or the modulator can be comprised for example, of a nucleic acid or PNA or MNA encapsulated inside a liposome, and the enhanced intracellular uptake is seen over the un-complexed oligonucleotide or modulator. The lipophilic compound or non-immunogenic, high molecular weight compound can be covalently bonded or associated through non-covalent interactions with ligand or modulator (s). In embodiments where the lipophilic compound is cholesterol, dialkyl glycerol, diacyl glycerol, or the non-immunogenic, high molecular weight compound is PEG, a covalent association with the oligonucleotide modulator (s) is preferred. In embodiments where the lipophilic compound is a cationic liposome or where the oligonucleotide modulators are encapsulated within the liposome, a non-covalent association with the oligonucleotide modulator (s) is preferred. In embodiments where covalent attachment is employed, the lipophilic compound or non-immunogenic, high molecular weight compound may be covalently bound to a variety of positions on the oligonucleotide modulator, such as to an exocyclic amino group on the base, the 5-position of a pyrimidine nucleotide, the 8-position of a purine nucleotide, the hydroxyl group of the phosphate, or a hydroxyl group or other group at the 5' or 3' terminus of the oligonucleotide modulator. Preferably, however, it is bonded to the 5' or 3' hydroxyl group thereof. Attachment of the oligonucleotide modulator to other components of the complex can be done directly or with the utilization of linkers or spacers. The lipophilic compound or non-immunogenic, high molecular weight compound can associate through non-covalent interactions with the oligonucleotide modulator(s). For example, in one embodiment of the present invention, the oligonucleotide modulator is encapsulated within the internal compartment of the lipophilic compound. In another embodiment of the present invention, the oligonucleotide modulator associates with the lipophilic compound through electrostatic interactions. For instance, a cationic liposome can associate with an anionic oligonucleotide modulator. Another example of a non-covalent interaction through ionic attractive forces is one in which a portion of the oligonucleotide modulator hybridizes through Watson-Crick base-pairing or triple helix base pairing to an oligonucleotide which is associated with a lipophilic compound or non-immunogenic, high molecular weight compound.

I. Definitions

The following terms are believed to have well-recognized meanings in the art. However, the following definitions are set forth to facilitate explanation of the invention.

The terms "binding activity" and "binding affinity' are meant to refer to the tendency of a ligand molecule to bind or not to bind to a target. The energy of said interactions are significant in "binding activity" and "binding affinity" because they define the necessary concentrations of interacting partners, the rates at which these partners are capable of associating, and the relative concentrations of bound and free molecules-in a solution. The energetics are characterized through, among other ways, the determination of a dissociation constant, $K_d$. Preferably, the $K_d$ is established using a double-filter nitrocellulose filter binding assay such as that disclosed by Wong and Lohman, 1993, *Proc. Natl Acad. Sci. USA* 90, 5428-5432. "Specifically binding oligonucleotides", "nucleic acid ligands" or "aptamers" in one embodiment of the invention are oligonucleotides having specific binding regions that are capable of forming complexes with an intended target molecule. The specificity of the binding is defined in terms of the comparative dissociation constants ($K_d$) of a modulator of a nucleic acid ligand as compared to the dissociation constant with respect to other materials in the environment or unrelated molecules in general. The $K_d$ for a modulator of a nucleic acid ligand can be 2-fold, preferably 5-fold, more preferably 10-fold less than the $K_d$ with respect to the modulator and the unrelated material or accompanying material in the environment. Even more preferably the $K_d$ will be 50-fold less, more preferably 100-fold less, and more preferably 200-fold less.

$K_d$ can be determined directly by well-known methods, and can be computed even for complex mixtures by methods such as those, for example, set forth in Caceci, M., et al., *Byte* {1984} 9:340-362. It has been observed, however, that for some small oligonucleotides, direct determination of $K_d$ is difficult, and can lead to misleadingly, high results. Under these circumstances, a competitive binding assay for the target molecule or other candidate substance can be conducted with respect to substances known to bind the target or candidate. The value of the concentration at which 50% inhibition occurs ($K_i$) is, under ideal conditions, equivalent to $K_d$. However, in no event will a $K_i$ be less than $K_d$. Thus, determination of $K_i$, in the alternative, sets a maximal value for the value of $K_d$. Under those circumstances where technical difficulties preclude accurate measurement of $K_d$, measurement of $K_i$ can conveniently be substituted to provide an upper limit for $K_d$. A $K_i$ value can also be used to confirm that a modulator binds a nucleic acid ligand.

As specificity is defined in terms of $K_d$ as set forth above, in certain embodiments of the present invention it is preferred to exclude from the categories of unrelated materials and materials accompanying the target in the target's environment those materials which are sufficiently related to the target to be immunologically cross-reactive therewith. By "immunologically cross-reactive" is meant that antibodies raised with respect to the target cross-react under standard assay conditions with the candidate material. Generally, for antibodies to cross-react in standard assays, the binding affinities of the antibodies for cross-reactive materials as compared to targets should be in the range of 5-fold to 100-fold, generally about 10-fold.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of compound need not be 100% complementary to that of its target nucleic acid to be specifically hybridizable. A compound is specifically hybridizable when binding of the compound to the target nucleic acid molecule interferes with the normal function of the target nucleic acid to cause a change in utility, and there is a sufficient degree of complementarity to avoid non-specific binding of the compound to non-target sequences under conditions in which specific binding is desired, i.e., under physiological conditions in the case of in vivo assays or therapeutic treatment, and in the case of in vitro assays, under conditions in which the assays are performed.

"Oligomers" or oligonucleotides" include RNA or DNA sequences or mixtures or analogs thereof, of more than one nucleotide in either single chain or duplex form and specifically includes short sequences such as dimers and trimers, in either single chain or duplex form, which can be intermediates in the production of the specifically binding oligonucleotides. "Modified" forms used in candidate pools contain at least one non-native residue.

The term "RNA analog" is meant to refer to a polymeric molecule which can contain one or more nucleotides that have a nonhydrogen substituent other than a hydroxyl group in the 2'-position, and for example, can contains at least one of the following: 2'-deoxy, 2'-halo (including 2'-fluoro), 2'-amino (preferably not substituted or mono- or disubstituted), 2'-mono-, di- or tri-halomethyl, 2'-O-alkyl (including 2'-O-methyl or O-ethyl), 2'-O-halo-substituted alkyl, 2'-alkyl, azido, phosphorothioate, sulfhydryl, methylphosphonate, fluorescein, rhodamine, pyrene, biotin, xanthine, hypoxanthine, 2,6-diamino purine, 2-hydroxy-6-mercaptopurine and pyrimidine bases substituted at the 6-position with sulfur or 5 position with halo or $C_{1-5}$ alkyl groups, a basic linkers, 3'-deoxy-adenosine as well as other available "chain terminator" or "non-extendible" analogs (at the 3'-end of the RNA), or labels such as $^{32}P$, $^{33}P$ and the like. All of the foregoing can be incorporated into an RNA using the standard synthesis techniques disclosed herein.

As used herein, a "target" or "target molecule" refers to a biomolecule that is the focus of a therapeutic drug strategy or diagnostic assay, including, without limitation, enzymes, enzyme inhibitors, hormones, glycoproteins, lipids, phospholipids, nucleic acids, intracellular, extracellular, and cell surface proteins, peptides, carbohydrates, including glycosaminoglycans, lipids, including glycolipids and certain oligonucleotides, and generally, any biomolecule capable of turning a biochemical pathway on or off or modulating it, or which is involved in a predictable biological response. Targets can be free in solution, like thrombin, or associated with cells or viruses, as in receptors or envelope proteins. Any molecule that is of sufficient size to be specifically recognized by a nucleic acid ligand can be used as the target. Thus, membrane structures, receptors, organelles, and the like can be used as the complexation targets.

An "RNA aptamer" is an aptamer comprising ribonucleoside units. "RNA aptamer" is also meant to encompass RNA analogs as defined herein above.

The term "coagulation factor aptamer" is meant to refer to a single- or double-stranded nucleic acid that binds a coagulation factor and modulates its function. The term "coagulation factor" is meant to refer to a factor that acts in either or both of the intrinsic and the extrinsic coagulation cascade.

As used herein, "consensus sequence" refers to a nucleotide sequence or region (which might or might not be made up of contiguous nucleotides) that is found in one or more regions of at least two nucleic acid sequences. A consensus sequence can be as short as three nucleotides long. It also can be made up of one or more noncontiguous sequences, with nucleotide sequences or polymers of up to hundreds of bases long interspersed between the consensus sequences. Consensus sequences can be identified by sequence comparisons between individual nucleic acid species, which comparisons can be aided by computer programs and other, tools for modeling secondary and tertiary structure from sequence information. Generally, the consensus sequence will contain at least about 3 to 20 nucleotides, more commonly from 6 to 10 nucleotides.

The terms "cardiovascular disease" and "cardiovascular diseases" are meant to refer to any cardiovascular disease as would be understood by one of ordinary skill in the art. Nonlimiting examples of particularly contemplated cardiovascular diseases include, but are not limited to, atherosclerosis, thrombophilia, embolisms, cardiac infarction (e.g., myocardial infarction), thromboses, angina, stroke, septic shock, hypertension, hyper-cholesterolemia, restenosis and diabetes.

The term "about," as used herein when referring to a measurable value such as an amount of weight, time, dose etc. is meant, to encompass variations of ±20% or ±10%, more preferably ±5%, even more preferably ±1%, and still more preferably ±0.1% from the specified amount, as such variations are appropriate to perform the disclosed method.

Compounds of the present invention having a chiral center may exist in and be isolated in optically active and racemic forms. Some compounds may exhibit polymorphism. The present invention encompasses racemic, optically-active, polymorphic, or stereoisomeric form, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. In a preferred embodiment, the compounds are used in naturally occurring forms. However, alternatively, the compounds can be used in a non-naturally occurring form.

II. Nucleic Acid Ligands

A "Nucleic Acid Ligand" (sometimes also referred to as an "aptamer") as used herein is a non-naturally occurring nucleic acid having a desirable action on a target. A desirable action includes, but is not limited to, binding of the target, catalytically changing the target, reacting with the target in a way which modifies/alters the target or the functional activity of the target, covalently attaching to the target as in a suicide inhibitor, or facilitating the reaction between the target and another molecule. In the preferred embodiment, the action is specific binding affinity for a target molecule, such target molecule being a three dimensional chemical structure, wherein the nucleic acid ligand is not a nucleic acid having the known physiological function of being bound by the target molecule. In one embodiment of the invention, the nucleic acid ligands are identified using the SELEX methodology. Nucleic acid ligands includes nucleic acids that are identified from a candidate mixture of nucleic acids, wherein the nucleic acid ligand being a ligand of a given target by the method comprising a) contacting the candidate mixture with the target, wherein nucleic acids having an increased affinity to the target relative to the candidate mixture may be partitioned from the remainder of the candidate mixture; b) partitioning the increased affinity nucleic acids from the remainder of the candidate mixture; and c) amplifying the increased affinity nucleic acids to yield a ligand-enriched mixture of nucleic acids. As used herein nucleic acid ligand or aptamer denotes both singular and plural sequences of nucleic acids which are capable of binding to a protein or other molecule, and thereby disturbing the protein's or other molecule's function.

Nucleic acid ligands can be made with nucleotides bearing D or L stereochemistry, or a mixture thereof. Naturally occurring nucleosides are in the D configuration. Aptamers have been made from L nucleotides, and are called L-aptamers. Nucleic acid ligands used for therapeutic purposes are typically in the D configuration, but can exhibit any configuration that provides the desired effect. Typically, when nucleic acid ligands comprising L-nucleotides are the target of an oligonucleotide modulator, the modulator also comprises L-nucleotides (see, for example, U.S. Pat. No. 5,780,221).

The nucleic acid ligands preferably comprise about 10 to about 100 nucleotides, preferably about 15 to about 40 nucleotides, more preferably about 20 to about 40 nucleotides, in that oligonucleotides of a length that falls within these ranges are readily prepared by conventional, techniques. In one embodiment, aptamers or oligonucleotide modulators can comprise a minimum of approximately 6 nucleotides, preferably 10, and more preferably 14 or 15 nucleotides, that are necessary to effect specific binding. The only apparent limitations on the binding specificity of the target/oligonucleotide couples of the invention concern sufficient sequence to be distinctive in the binding oligonucleotide and sufficient binding capacity of the target substance to obtain the necessary interaction. Aptamers of binding regions containing sequences shorter than 10, e.g., 6-mers, are feasible if the appropriate interaction can be obtained in the context of the environment in which the target is placed. Thus, if there is little interference by other materials, less specificity and less strength of binding can be required.

Nucleic acid ligands and methods for their production and use, are described, for example, in the following U.S. patents. Any of the nucleic acid ligands described in the patents listed below or other patents, or any nucleic acid ligands described in publications as well as other desired nucleic acid ligands used in medical therapy can be modulated or regulated according to the present invention. U.S. Pat. No. 6,387,635, entitled 2'-fluoropyrimidine anti-calf intestinal phosphatase nucleic acid ligands; U.S. Pat. No. 6,387,620, entitled Transcription-free selex; U.S. Pat. No. 6,379,900, entitled Compositions and methods of use of 8-nitroguanine; U.S. Pat. No. 6,376,474, entitled Systematic evolution of ligands by exponential enrichment: tissue SELEX; U.S. Pat. No. 6,376,190, entitled Modified SELEX processes without purified protein; U.S. Pat. No. 6,355,787, entitled Purine nucleoside modifications by palladium catalyzed methods and compounds produced; U.S. Pat. No. 6,355,431, entitled Detection of nucleic acid amplification reactions using bead arrays; U.S. Pat. No. 6,346,611, entitled High affinity TGFβ nucleic acid ligands and inhibitors; U.S. Pat. No. 6,344,321, entitled Nucleic acid ligands which bind to hepatocyte growth factor/scatter factor (HGF/SF) or its receptor c-met; U.S. Pat. No. 6,344,318, entitled Methods of producing nucleic acid ligands; U.S. Pat. No. 6,331,398, entitled Nucleic acid ligands; U.S. Pat. No. 6,331,394, entitled Nucleic acid ligands to integrins; U.S. Pat. No. 6,329,145, entitled Determining non-nucleic acid molecule binding to target by competition with nucleic acid ligand; U.S. Pat. No. 6,306,598, entitled Nucleic acid-coupled colorimetric analyte detectors; U.S. Pat. No. 6,303,316, entitled Organic semiconductor recognition complex and system; U.S. Pat. No. 6,300,074, entitled Systematic evolution of ligands by exponential enrichment: ChemiSELEX; U.S. Pat. No. 6,291,184, entitled Systematic evolution of ligands by exponential enrichment: photoselection of nucleic acid ligands and solution selex; U.S. Pat. No. 6,287,765, entitled Methods for detecting and identifying single molecules; U.S. Pat. No. 6,280,943, entitled 2'-fluoropyrimidine anti-calf intestinal phosphatase nucleic acid ligands; U.S. Pat. No. 6,280,932, entitled High affinity nucleic acid ligands to lectins; U.S. Pat. No. 6,264,825, entitled Binding acceleration techniques for the detection of analytes; U.S. Pat. No. 6,261,783, entitled Homogeneous detection of a target through nucleic acid ligand-ligand beacon interaction; U.S. Pat. No. 6,261,774, entitled Truncation selex method; U.S. Pat. No. 6,242,246, entitled Nucleic acid ligand diagnostic Biochip; U.S. Pat. No. 6,232,071, entitled Tenascin-C nucleic acid ligands; U.S. Pat. No. 6,229,002, entitled Platelet derived growth factor (PDGF) nucleic acid ligand complexes; U.S. Pat. No. 6,225,063, entitled RNA channels in biological membranes; U.S. Pat. No. 6,207,816, entitled High affinity oligonucleotide ligands to growth factors; U.S. Pat. No. 6,207,388, entitled Compositions, methods, kits and apparatus for determining the presence or absence of target molecules; U.S. Pat. No. 6,184,364, entitled High affinity nucleic acid ligands containing modified nucleotides; U.S. Pat. No. 6,183,967, entitled Nucleic acid ligand inhibitors to DNA polymerases; U.S. Pat. No. 6,180,348, entitled Method of isolating target specific oligonucleotide ligands; U.S. Pat. No. 6,177,557, entitled High affinity ligands of basic fibroblast growth factor and thrombin; U.S. Pat. No. 6,177,555, entitled Homogeneous detection of a target through nucleic acid ligand-ligand beacon interaction; U.S. Pat. No. 6,171,795, entitled Nucleic acid ligands to CD40 ligand; U.S. Pat. No. 6,168,778, entitled Vascular endothelial growth factor (VEGF) Nucleic Acid Ligand Complexes; U.S. Pat. No. 6,147,204, entitled Nucleic acid ligand complexes; U.S. Pat. No. 6,140,490, entitled High affinity nucleic acid ligands of complement system proteins; U.S. Pat. No. 6,127,119, entitled Nucleic acid ligands of tissue target; U.S. Pat. No. 6,124,449, entitled High affinity TGFβ nucleic acid ligands and inhibitors; U.S. Pat. No. 6,114,120, entitled Systematic evolution of ligands by exponential enrichment: tissue selex; U.S. Pat. No. 6,110,900, entitled Nucleic acid ligands; U.S. Pat. No. 6,083,696, entitled Systematic evolution of ligands exponential enrichment: blended selex; U.S. Pat. No. 6,080,585, entitled Methods for discovering ligands; U.S. Pat. No. 6,051,698, entitled Vascular endothelial growth factor (VEGF) nucleic acid ligand complexes; U.S. Pat. No. 6,048,698, entitled Parallel SELEX; U.S. Pat. No. 6,030,776, entitled Parallel SELEX; U.S. Pat. No. 6,028,186, entitled High affinity nucleic acid ligands of cytokines; U.S. Pat. No. 6,022,691, entitled Determination of oligonucleotides for therapeutics, diagnostics and research reagents; U.S. Pat. No. 6,020,483, entitled Nucleoside modifications by palladium catalyzed methods; U.S. Pat. No. 6,020,130, entitled Nucleic acid ligands that bind to and inhibit DNA polymerases; U.S. Pat. No. 6,013,443, entitled Systematic evolution of ligands by exponential enrichment: tissue SELEX; U.S. Pat. No. 6,011,020, entitled Nucleic acid ligand complexes; U.S. Pat. No. 6,001,988, entitled High affinity nucleic acid ligands to lectins; U.S. Pat. No. 6,001,577, entitled Systematic evolution of ligands by exponential enrichment: photoselection of nucleic acid ligands and solution selex; U.S. Pat. No. 6,001,570, entitled Compositions, methods, kits and apparatus for determining the presence or absence of target molecules; U.S. Pat. No. 5,998,142, entitled Systematic evolution of ligands by exponential enrichment: chemi-SELEX; U.S. Pat. No. 5,989,823, entitled Homogeneous detection of a target through nucleic acid ligand-ligand beacon interaction; U.S. Pat. No. 5,972,599, entitled High affinity nucleic acid ligands of cytokines; U.S. Pat. No. 5,962,219, entitled Systematic evolution of ligands by exponential enrichment: chemi-selex; U.S. Pat. No. 5,958,691, entitled High affinity nucleic acid ligands containing modified nucleotides; U.S. Pat. No. 5,874,557, entitled Nucleic acid ligand inhibitors to DNA polymerases; U.S. Pat. No. 5,874,218, entitled Method for detecting a target compound in a substance using a nucleic acid ligand; U.S. Pat. No. 5,871,924, entitled Method for the production of ligands capable of facilitating aminoacyl-RNA synthesis; U.S. Pat. No. 5,869,641, entitled High affinity nucleic acid ligands of CD4; U.S. Pat. No. 5,864,026, entitled Systematic evolution of ligands by exponential enrichment: tissue selex; U.S. Pat. No. 5,861,254, entitled Flow cell SELEX; U.S. Pat. No. 5,859,228, entitled Vascular endothelial growth factor (VEGF) nucleic acid ligand complexes; U.S. Pat. No. 5,858,660, entitled Parallel selex; U.S. Pat. No. 5,853,984, entitled Use of nucleic acid ligands in flow cytometry; U.S. Pat. No. 5,849,890, entitled High affinity oligonucleotide ligands to chorionic gonadotropin hormone and related glycoprotein hormones; U.S. Pat. No. 5,849,479, entitled High-affinity oligonucleotide ligands to vascular endothelial growth factor (VEGF); U.S. Pat. No. 5,846,713, entitled High affinity HKGF nucleic acid ligands and inhibitors; U.S. Pat. No. 5,843,653, entitled Method for detecting a target molecule in a sample using a nucleic acid ligand; U.S. Pat. No. 5,837,834, entitled High affinity HKGF nucleic acid ligands and inhibitors; U.S. Pat. No. 5,837,456, entitled High affinity oligonucleotide ligands to chorionic gonadotropin hormone and related glycoprotein hormones; U.S. Pat. No. 5,834,199, entitled Methods of identifying transition metal complexes that selectively cleave regulatory elements of mRNA and uses thereof, U.S. Pat. No. 5,817,785, entitled Methods of producing nucleic acid ligands; U.S. Pat. No. 5,811,533, entitled High-affinity oligonucleotide ligands to vascular endothelial growth factor (VEGF); U.S. Pat. No. 5,795,721, entitled High affinity nucleic acid ligands of ICP4; U.S. Pat. No. 5,789,163, entitled Enzyme linked oligonucleotide assays (ELONAS); U.S. Pat. No. 5,789,160, entitled Parallel selex; U.S. Pat. No. 5,789,157, entitled Systematic evolution of ligands by exponential enrichment: tissue selex; U.S. Pat. No. 5,786,462, entitled High affinity ssDNA ligands of HIV-1 reverse transcriptase; U.S. Pat. No. 5,780,228, entitled High affinity nucleic acid ligands to lectins U.S. Pat. No. 5,773,598, entitled Systematic evolution of ligands by exponential enrichment: chimeric selex; U.S. Pat. No. 5,766,853, entitled Method for identification of high affinity nucleic acid ligands to selectins; U.S. Pat. No. 5,763,595, entitled Systematic evolution of ligands by exponential enrichment: Chemi-SELEX; U.S. Pat. No. 5,763,566, entitled Systematic evolution of ligands by exponential enrichment: tissue SELEX; U.S. Pat. No. 5,763,177, entitled Systematic evolution of ligands by exponential enrichment: photoselection of nucleic acid ligands and solution selex; U.S. Pat. No. 5,763,173, entitled Nucleic acid ligand inhibitors to DNA polymerases; U.S. Pat. No. 5,756,287, entitled High affinity HIV integrase inhibitors; U.S. Pat. No. 5,750,342, entitled Nucleic acid ligands of tissue target; U.S. Pat. No. 5,734,034, entitled Nucleic acid ligand inhibitors of human neutrophil elastase; U.S. Pat. No. 5,731,424, entitled High affinity TGFβ nucleic acid ligands and inhibitors; U.S. Pat. No. 5,731,144, entitled High affinity TGFβ nucleic acid ligands; U.S. Pat. No. 5,726,017, entitled High affinity HIV-1 gag nucleic acid ligands; U.S. Pat. No. 5,723,594, entitled High affinity PDGF nucleic acid ligands; U.S. Pat. No. 5,723,592, entitled Parallel selex; U.S. Pat. No. 5,723,289, entitled Parallel selex; U.S. Pat. No. 5,712,375, entitled Systematic evolution of ligands by exponential enrichment: tissue selex; U.S. Pat. No. 5,707,796, entitled Method for selecting nucleic acids on the basis of structure; U.S. Pat. No. 5,705,337, entitled Systematic evolution of ligands by exponential enrichment: chemi-SELEX; U.S. Pat. No. 5,696,249, entitled Nucleic acid ligands; U.S. Pat. No. 5,693,502, entitled Nucleic acid ligand inhibitors to DNA polymerases; U.S. Pat. No. 5,688,935, entitled Nucleic acid ligands of tissue target; U.S. Pat. No. 5,686,592, entitled High-affinity oligonucleotide ligands to immunoglobulin E (IgE); U.S. Pat. No. 5,686,242, entitled Determination of oligonucleotides for therapeutics, diagnostics and research reagents; U.S. Pat. No. 5,683,867, entitled Systematic evolution of ligands by exponential enrichment: blended SELEX;

U.S. Pat. No. 5,674,685, entitled High affinity PDGF nucleic acid ligands; U.S. Pat. No. 5,670,637, entitled Nucleic acid ligands; U.S. Pat. No. 5,668,264, entitled High affinity PDGF nucleic acid ligands; U.S. Pat. No. 5,663,064, entitled Ribozymes with RNA protein binding site; U.S. Pat. No. 5,660,985, entitled High affinity nucleic acid ligands containing modified nucleotides; U.S. Pat. No. 5,654,151, entitled High affinity HIV Nucleocapsid nucleic acid ligands; U.S. Pat. No. 5,650,275, entitled Target detection method using spectroscopically detectable nucleic acid ligands; U.S. Pat. No. 5,648,214, entitled High-affinity oligonuclebtide ligands to the tachykinin substance P; U.S. Pat. No. 5,641,629, entitled Spectroscopically detectable nucleic acid ligands; U.S. Pat. No. 5,639,868, entitled High-affinity RNA ligands for basic fibroblast growth factor; U.S. Pat. No. 5,637,682, entitled High-affinity oligonucleotide ligands to the tachykinin substance P; U.S. Pat. No. 5,637,461, entitled Ligands of HIV-1 TAT protein; U.S. Pat. No. 5,637,459, entitled Systematic evolution of ligands by exponential enrichment: chimeric selex; U.S. Pat. No. 5,635,615, entitled High affinity HIV nucleocapsid nucleic acid ligands; U.S. Pat. No. 5,629,155, entitled High-affinity oligonucleotide ligands to imniunoglobulin E (IgE); U.S. Pat. No. 5,622,828, entitled High-affinity oligonucleotide ligands to secretory phospholipase A2(sPLA.sub.2); U.S. Pat. No. 5,595,877, entitled Methods of producing nucleic acid ligands; U.S. Pat. No. 5,587,468, entitled High affinity nucleic acid ligands to HIV integrase; U.S. Pat. No. 5,580,737, entitled High-affinity nucleic acid ligands that discriminate between theophylline and caffeine; U.S. Pat. No. 5,567,588, entitled Systematic evolution of ligands by exponential enrichment: Solution SELEX; U.S. Pat. No. 5,543,293, entitled DNA ligands of thrombin; U.S. Pat. No. 5,527,894, entitled Ligands of HIV-1 tat protein; U.S. Pat. No. 5,475,096, entitled Nucleic acid ligands; U.S. Pat. No. 5,866,334, entitled Determination and identification of active compounds in a compound library; U.S. Pat. No. 5,864,026, entitled Systematic evolution of ligands by exponential enrichment: tissue selex; U.S. Pat. No. 5,861,254, entitled Flow cell SELEX; U.S. Pat. No. 5,859,228, entitled Vascular endothelial growth factor (VEGF) nucleic acid ligand complexes; U.S. Pat. No. 5,858,660, entitled Parallel selex; U.S. Pat. No. 5,853,984, entitled Use of nucleic acid ligands in flow cytometry; U.S. Pat. No. 5,849,890, entitled High affinity oligonucleotide ligands to chorionic gonadotropin hormone and related glycoprotein hormones; U.S. Pat. No. 5,849,479, entitled High-affinity oligonucleotide ligands to vascular endothelial growth factor (VEGF); U.S. Pat. No. 5,846,713, entitled High affinity HKGF nucleic acid ligands and inhibitors; U.S. Pat. No. 5,843,732, entitled Method and apparatus for determining consensus secondary structures for nucleic acid sequences; U.S. Pat. No. 5,843,653, entitled Method for detecting a target molecule in a sample using a nucleic acid ligand; U.S. Pat. No. 5,840,867, entitled Aptamer analogs specific for biomolecules; U.S. Pat. No. 5,840,580, entitled Phenotypic characterization of the hematopoietic stem cell; U.S. Pat. No. 5,837,838, entitled Bax inhibitor proteins; U.S. Pat. No. 5,837,834, entitled High affinity HKGF nucleic acid ligands and inhibitors; U.S. Pat. No. 5,837,456, entitled High affinity oligonucleotide ligands to chorionic gonadotropin hormone and related glycoprotein hormones; U.S. Pat. No. 5,834,199, entitled Methods of identifying transition metal complexes that selectively cleave regulatory elements of mRNA and uses thereof, U.S. Pat. No. 5,834,184, entitled In vivo selection of RNA-binding peptides; U.S. Pat. No. 5,817,785, entitled Methods of producing nucleic acid ligands; U.S. Pat. No. 5,811,533, entitled High-affinity oligonucleotide ligands to vascular endothelial growth factor (VEGF); U.S. Pat. No. 5,804,390, entitled Use of nuclear magnetic resonance to identify ligands to target biomolecules; U.S. Pat. No. 5,795,721, entitled High affinity nucleic acid ligands of ICP4; U.S. Pat. No. 5,789,163, entitled Enzyme linked oligonucleotide assays (ELONAS); U.S. Pat. No. 5,789,160, entitled Parallel selex; U.S. Pat. No. 5,789,157, entitled Systematic evolution of ligands by exponential enrichment: tissue selex; U.S. Pat. No. 5,786,462, entitled High affinity ssDNA ligands of MV-1 reverse transcriptase; U.S. Pat. No. 5,786,203, entitled Isolated nucleic acid encoding corticotropin-releasing factor.sub.2 receptors; U.S. Pat. No. 5,786,145, entitled Oligonucleotide competitors for binding of HIV RRE to REV protein and assays for screening inhibitors of this binding; U.S. Pat. No. 5,783,566, entitled Method for increasing or decreasing transfection efficiency; U.S. Pat. No. 5,780,610, entitled Reduction of nonspecific hybridization by using novel base-pairing schemes; U.S. Pat. No. 5,780,228, entitled High affinity nucleic acid ligands to lectins; U.S. Pat. No. 5,773,598, entitled Systematic evolution of ligands by exponential enrichment: chimeric selex; U.S. Pat. No. 5,770,434, entitled Soluble peptides having constrained, secondary conformation in solution and method of making same; U.S. Pat. No. 5,766,853, entitled Method for identification of high affinity nucleic acid ligands to selectins; U.S. Pat. No. 5,763,595, entitled Systematic evolution of ligands by exponential enrichment: Chemi-SELEX; U.S. Pat. No. 5,763,566, entitled Systematic evolution of ligands by exponential enrichment: tissue SELEX; U.S. Pat. No. 5,763,177, entitled Systematic evolution of ligands by exponential enrichment: photoselection of nucleic acid ligands and solution selex; U.S. Pat. No. 5,763,173, entitled Nucleic acid ligand inhibitors to DNA polymerases; U.S. Pat. No. 5,756,296, entitled Nucleotide-directed assembly of bimolecular and multimolecular drugs and devices; U.S. Pat. No. 5,756,291, entitled Aptamers specific for biomolecules and methods of making; U.S. Pat. No. 5,756,287, entitled High affinity HIV integrase inhibitors; U.S. Pat. No. 5,750,342, entitled Nucleic acid ligands of tissue target; U.S. Pat. No. 5,739,305, entitled Nucleotide-directed assembly of bimolecular and multimolecular drugs and devices; U.S. Pat. No. 5,734,034, entitled Nucleic acid ligand inhibitors of human neutrophil elastase; U.S. Pat. No. 5,733,732, entitled Methods for detecting primary adhalinopathy; U.S. Pat. No. 5,731,424, entitled High affinity TGF.beta nucleic acid ligands and inhibitors; U.S. Pat. No. 5,731,144, entitled High affinity TGF.beta nucleic acid ligands; U.S. Pat. No. 5,726,017, entitled High affinity HIV-1 gag nucleic acid ligands; U.S. Pat. No. 5,726,014, entitled Screening assay for the detection of DNA-binding molecules; U.S. Pat. No. 5,723,594, entitled High affinity PDGF nucleic acid ligands; U.S. Pat. No. 5,723,592, entitled Parallel selex; U.S. Pat. No. 5,723,289, entitled Parallel selex; U.S. Pat. No. 5,712,375, entitled Systematic evolution of ligands by exponential enrichment: tissue selex; U.S. Pat. No. 5,707,796, entitled Method for selecting nucleic acids on the basis of structure; U.S. Pat. No. 5,705,337, entitled Systematic evolution of ligands by exponential enrichment: chemi-SELEX; U.S. Pat. No. 5,698,442, entitled DNA encoding an 18 Kd CDK6 inhibiting protein; U.S. Pat. No. 5,698,426, entitled Surface expression libraries of heteromeric receptors; U.S. Pat. No. 5,698,401, entitled Use of nuclear magnetic resonance to identify ligands to target biomolecules; U.S. Pat. No. 5,693,502, entitled Nucleic acid ligand inhibitors to DNA polymerases; U.S. Pat. No. 5,688,935, entitled Nucleic acid ligands of tissue target; U.S. Pat. No. 5,688,670, entitled Self-modifying RNA molecules and methods of making; U.S. Pat. No. 5,686,592, entitled High-affinity oligonucleotide ligands to immunoglobulin E (IgE); U.S. Pat.

No. 5,683,867, entitled Systematic evolution of ligands by exponential enrichment: blended SELEX; U.S. Pat. No. 5,681,702, entitled Reduction of nonspecific hybridization by using novel base-pairing schemes; U.S. Pat. No. 5,674,685, entitled High affinity PDGF nucleic acid ligands; U.S. Pat. No. 5,670,637, entitled Nucleic acid ligands; U.S. Pat. No. 5,668,265, entitled Bi-directional oligonucleotides that bind thrombin; U.S. Pat. No. 5,668,264, entitled High affinity PDGF nucleic acid ligands; U.S. Pat. No. 5,660,985, entitled High affinity nucleic acid ligands containing modified nucleotides; U.S. Pat. No. 5,660,855, entitled Lipid constructs for targeting to vascular smooth muscle tissue; U.S. Pat. No. 5,658,738, entitled Bi-directional oligonucleotides that bind thrombin; U.S. Pat. No. 5,656,739, entitled Nucleotide-directed assembly of bimolecular and multimolecular drugs and devices; U.S. Pat. No. 5,656,467, entitled Methods and materials for producing gene libraries; U.S. Pat. No. 5,654,151, entitled High affinity HIV Nucleocapsid nucleic acid ligands; U.S. Pat. No. 5,650,275, entitled Target detection method using spectroscopically detectable nucleic acid ligands; U.S. Pat. No. 5,648,214, entitled High-affinity oligonucleotide ligands to the tachykinin substance P; U.S. Pat. No. 5,641,629, entitled Spectroscopically detectable nucleic acid ligands; U.S. Pat. No. 5,639,868, entitled High-affinity RNA ligands for basic fibroblast growth factor; U.S. Pat. No. 5,639,428, entitled Method and apparatus for fully automated nucleic acid amplification, nucleic acid assay and immunoassay; U.S. Pat. No. 5,637,682, entitled High-affinity oligonucleotide ligands to the tachykinin substance P; U.S. Pat. No. 5,637,459, entitled Systematic evolution of ligands by exponential enrichment: chimeric selex; U.S. Pat. No. 5,635,615, entitled High affinity HIV nucleocapsid nucleic acid ligands; U.S. Pat. No. 5,631,156, entitled DNA encoding and 18 KD CDK6 inhibiting protein; U.S. Pat. No. 5,631,146, entitled DNA aptamers and catalysts that bind adenosine or adenosine-5'-phosphates and methods for isolation thereof, U.S. Pat. No. 5,629,407, entitled DNA encoding an 18 KD CDK6 inhibiting protein and antibodies thereto; U.S. Pat. No. 5,629,155, entitled High-affinity oligonucleotide ligands to immunoglobulin E (IgE); U.S. Pat. No. 5,622,828, entitled High-affinity oligonucleotide ligands to secretory phospholipase A2 (sPLA.sub.2); U.S. Pat. No. 5,621,082, entitled DNA encoding an 18 Kd CDK6 inhibiting protein; U.S. Pat. No. 5,599,917, entitled Inhibition of interferon-gamma with oligonucleotides; U.S. Pat. No. 5,597,696, entitled Covalent cyanine dye oligonucleotide conjugates; U.S. Pat. No. 5,587,468, entitled High affinity nucleic acid ligands to HIV integrase; U.S. Pat. No. 5,585,269, entitled Isolated DNA encoding c-mer protooncogene; U.S. Pat. No. 5,580,737, entitled High-affinity nucleic acid ligands that discriminate between theophylline and caffeine; U.S. Pat. No. 5,567,588, entitled Systematic evolution of ligands by exponential enrichment: Solution SELEX; U.S. Pat. No. 5,565,327, entitled Methods of diagnosing parasitic infections and of testing drug susceptibility of parasites; U.S. Pat. No. 5,527,894, entitled Ligands of HIV-1 tat protein; U.S. Pat. No. 5,512,462, entitled Methods and reagents for the polymerase chain reaction amplification of long DNA sequences; U.S. Pat. No. 5,503,978, entitled Method for identification of high affinity DNA ligands of HIV-1 reverse transcriptase; U.S. Pat. No. 5,472,841, entitled Methods for identifying nucleic acid ligands of human neutrophil elastase; and U.S. Pat. No. 5,459,015, entitled High-affinity RNA ligands of basic fibroblast growth factor.

III. Types of Modulators

Modulators (i.e., regulators) of the invention include any pharmaceutically acceptable agent that can bind a nucleic acid ligand and modify the interaction between that ligand and its target molecule (e.g., by modifying the structure of the aptamer) in a desired manner, or which degrades, metabolizes, cleaves or otherwise chemically alters the nucleic acid ligand to modify its biological effect. Examples of modulators include (A) oligonucleotides or analogues thereof that are complementary to at least a portion of the aptamer sequence (including ribozymes or DNAzymes or, for example, peptide nucleic acids (PNAs), mopholino nucleic acids (MNAs), or Locked Nucleic Acids (LNAs)), (B) nucleic acid binding peptides, polypeptides or proteins (including nucleic acid binding tripeptides (see, generally, Hwang et al., Proc. Natl. Acad. Sci. USA 96:12997 (1999)), (C) oligosaccharides (e.g. aminoglycosides (see, generally, Davis et al., Chapter 8, p. 185, RNA World, Cold Spring Harbor Laboratory Press, eds Gestlaad and Atkins (1993), (D) small molecules, and (E) chimeras, fusion products, or other combinations of any of the above. Werstuck et al., Sciende 282:296 (1998), U.S. Pat. Nos. 5,935,776 and 5,534,408). (See also the following which disclose types of modulators that can be used in accordance with the present invention: Chase et al., Ann. Rev. Biochem. 56:103 (1986), Eichorn et al., J. Am. Chem. Soc. 90:7323 (1968), Dale et al., Biochemistry 14:2447 (1975) and Lippard et al., Acc. Chem. Res. 11:211 (1978)).

In an alternative embodiment of the invention, the modulator itself is an aptamer. In this embodiment, a nucleic acid ligand is first generated that binds to the desired therapeutic target. In a second step, a second aptamer that binds to the first aptamer is generated using the SELEX process described herein or other process, and modulates the interaction between the therapeutic aptamer and the target.

In other alternative embodiments, the nucleic acid ligand which binds to the target is a PNA, MNA, LNA or PCO and the modulator is an aptamer. Alternatively, the nucleic acid ligand which binds to the target is a PNA, MNA, LNA or PCO, and the modulator is an MNA. Alternatively, the nucleic acid ligand which binds to the target is a PNA, MNA, LNA or PCO, and the modulator is an LNA. Alternatively, the nucleic acid ligand which binds to the target is a PNA, MNA, LNA or PCO, and the modulator is a PCO.

Oligonucleotides and Analogues Thereof

1. Polynucleic Acid

In a preferred embodiment, the modulator of the invention is an oligonucleotide that comprises a sequence complementary to at least a portion of the targeted nucleic acid ligand sequence. For example, the modulator oligonucleotide can comprise a sequence complementary to 6-25 nucleotides of the targeted nucleic acid ligand, typically, 8-20 nucleotides, more typically, 10-15 nucleotides. Advantageously, the modulator oligonucleotide is complementary to 6-25 consecutive nucleotides of the nucleic acid ligand, or 8-20 or 10-15 consecutive nucleotides. The length of the modulator oligonucleotide can be readily optimized taking into account the targeted nucleic acid ligand and the effect sought. Typically the modulator oligonucleotide is 5-80 nucleotides in length, more typically, 10-30 and most typically 15-20 nucleotides (e.g., 15-17). The oligonucleotide can be made with nucleotides bearing D or L stereochemistry, or a mixture thereof. Naturally occurring nucleosides are in the D configuration.

Formation of duplexes by binding of complementary pairs of short oligonucleotides is a fairly rapid reaction with second order association rate constants generally between $1 \times 10^6$ and $3 \times 10^5$ $M^{-1}s^{-1}$. The initial phase of the binding reaction involves formation of a two to three base pair duplex, termed "nucleation". After nucleation, pairing proceeds through the entire length of the complementary sequence at a very fast rate—approximately $10^6$ bases per second at 20° C. Thus, the modulatory effect on a nucleic acid ligand by formation of a duplex with a complimentary oligonucleotide is rapid. Stability of short duplexes is highly dependent on the length and base-composition of the duplex. The thermodynamic parameters for formation of short nucleic acid duplexes have been rigorously measured, resulting in nearest-neighbor rules for all possible base pairs such that accurate predictions of the free energy, $T_m$ and thus half-life of a given oligoribonucleotide duplex can be calculated (e.g., Xia et al., Biochem. 37:14719 (1998) (see also Eguchi et al. Antigensis RNA, Annu. Rev. Biochem. 60:631 (1991)).

Oligonucleotide modulators of the invention are advantageously targeted at single-stranded regions of the nucleic acid ligand. This facilitates nucleation and, therefore, the rate of nucleic acid ligand activity modulation, and also, generally leads to intermolecular duplexes that contain more base pairs than the targeted nucleic acid ligand.

Various strategies can be used to determine the optimal site for oligonucleotide binding to a targeted nucleic acid ligand. An empirical strategy can be used in which complimentary oligonucleotides are "walked" around the aptamer. A walking experiment can involve two experiments performed sequentially. A new candidate mixture can be produced in which each of the members of the candidate mixture has a fixed nucleic acid-region that corresponds to a oligonucleotide modulator of interest. Each member of the candidate mixture also contains a randomized region of sequences. According to this method it is possible to identify what are referred to as "extended" nucleic acid ligands, which contain regions that can bind to more than one binding domain of an nucleic acid ligand. In accordance with this approach, 2'-O-methyl oligonucleotides (e.g., 2'-O-methyl oligonucleotides) about 15 nucleotides in length can be used that are staggered by about 5 nucleotides on the aptamer (e.g., oligonucleotides complementary to nucleotides 1-15, 6-20, 11-25, etc. of aptamer 9.3t. An empirical strategy can be particularly effective because the impact of the tertiary structure of the aptamer on the efficiency of hybridization can be difficult to predict. Assays described in the Examples that follow can be used to assess the ability of the different oligonucleotides to hybridize to a specific nucleic acid ligand, with particular emphasis on the molar excess of the oligonucleotide required to achieve complete binding of the nucleic acid ligand. The ability of the different oligonucleotide modulators to increase the rate of dissociation of the nucleic acid ligand from, or association of the nucleic acid ligand with, its target molecule can also be determined by conducting standard kinetic studies using, for example, BIACORE assays. Oligonucleotide modulators can be selected such that a 5-50 fold molar excess of oligonucleotide, or less, is required to modify the interaction between the nucleic acid ligand and its target molecule in the desired manner.

Alternatively, the targeted nucleic acid ligand can be modified so as to include a single-stranded tail (3' or 5') in order to promote association with an oligonucleotide modulator. Suitable tails can comprise 1 to 20 nucleotides, preferably, 1-10 nucleotides, more preferably, 1-5 nucleotides and, most preferably, 3-5 nucleotides (e.g., modified nucleotides such as 2'-O-methyl sequences). Tailed nucleic acid ligands can be tested in binding and bioassays (e.g., as described in the Examples that follow) to verify that addition of the single-stranded tail does not disrupt the active structure of the nucleic acid ligand. A series of oligonucleotides (for example, 2'-O-methyl oligonucleotides) that can form, for example, 1, 3 or 5 base pairs with the tail sequence can be designed and tested for their ability to associate with the tailed aptamer alone, as well as their ability to increase the rate of dissociation of the nucleic acid ligand from, or association of the aptamer with, its target molecule. Scrambled sequence controls can be employed to verify that the effects are due to duplex formation and not non-specific effects. The native gel assay described in the Examples that follow can be used to measure the dissociation/association rate of an oligonucleotide modulator from/with a target aptamer.

As an illustrative embodiment, the present invention provides modulators that specifically and rapidly reverse the anticoagulant and antithrombotic effects of nucleic acid ligands that target components of the coagulation pathway, particularly nucleic acid ligand antagonists of the tissue factor (TF)/factor VIIa (FVIIa), factor VIIIa (FVIIIa)/factor IXa (FIXa), factor Va (FVa/factor Xa (Fxa) enzyme complexes and platelet receptors such as gpIIbIIIa, gpIbIX, gpVI, factors involved in promoting platelet activation such as Gas6, factors involved in promoting or maintaining fibrin clot formation such as PAI-1 (plasminogen activator inhibitor 1) or coagulation factor XIIIa (FXIIIa), and additional factors involved in promoting or preventing fibrin clot formation such as ATIII (anti-thrombin III), thrombin or coagulation factor XIa (FXIa). In accordance with this embodiment, modulators (in this case, inhibitors, advantageously, oligonucleotide inhibitors) are administered that reverse the nucleic acid ligand activity.

In specific embodiments, modulators of nucleic acid ligand activity according to the present invention are nucleic acids selected from the group consisting of, but not limited to the following sequences; 5'AUGGGGAGGCAGCAUUA 3' (SEQ ID NO:25), 5'CAUGGGGAGGCAGCAUUA3' (SEQ ID NO:26), 5'CAUGGGGAGGCAGCA3' (SEQ ID NO:27), 5'CAUGGGGAGGCA3' (SEQ ID NO:28), 5'GCA-UUACGCGGUAUAGUCCCCUA3' (SEQ ID NO:29), 5'CGCGGUAUAGUCCCCUA3' (SEQ ID NO:30), 5'CUCGCUGGGGCUCUC3' (SEQ ID NO: 31), 5'UAUUAUCUCGCUGGG3' (SEQ ID NO:32), 5'AAGAGCGGGGCCAAG3' (SEQ ID NO:33), 5'GGGC-CAAGUAUUAU 3' (SEQ ID NO:34), 5'CAA-GAGCGGGGCCAAG 3' (SEQ ID NO:35), 5'CGAGUA-UUAUCUUG3' (SEQ ID NO:36), 5'CGCGGUAUAGUCCCCAU3' (SEQ ID NO:41), or any modification or derivative thereof in which hybridization is maintained or is optionally at least 95% homologous to the sequence.

For example, the inhibitor of a nucleic acid ligand to Factor IXa of the present invention can be an antisense oligonucleotide. The antisense oligonucleotide hybridizes to the nucleic acid ligand in vivo and blocks the binding of the nucleic acid ligand to factor IXa.

The oligonucleotide modulators of the invention comprise a sequence complementary to at least a portion of a nucleic acid ligand. However, absolute complementarity is not required. A sequence "complementary to at least a portion of a nucleic acid ligand," referred to herein, means a sequence having sufficient complementarity to be able to hybridize with the nucleic acid ligand. The ability to hybridize can depend on both the degree of complementarity and the length of the antisense nucleic acid. Generally, the larger the hybridizing oligonucleotide, the more base mismatches with a target nucleic acid ligand it can contain and still form a stable duplex (or triplex as the case may be). One skilled in the art can ascertain a tolerable degree of mismatch by use of standard procedures to determine the melting point of the hybridized complex. In specific aspects, the oligonucleotide can be at least 5 or at least 10 nucleotides, at least 15 or 17 nucleotides, at least 25 nucleotides or at least 50 nucleotides. The oligonucleotides of the invention can be DNA or RNA or chimeric mixtures or derivatives or modified versions thereof, single-stranded.

Antisense techniques are discussed for example, in Okano, J., Neurochein. 56:560 (1991);Oligodeoxynucleotides as Antisense Inhibitors of Gene Expression, CRC Press, Boca Raton, Fla. (1988). The methods are based on binding of a polynucleotide to a complementary DNA or RNA.

Oligonucleotides of the invention can be modified at the base moiety, sugar moiety, or phosphate backbone, for example, to improve stability of the molecule, hybridization, etc. The oligonucleotide can include other appended groups. To this end, the oligonucleotide can be conjugated to another molecule, e.g., a peptide, hybridization triggered cross-linking agent, transport agent, hybridization-triggered cleavage agent, etc. The oligonucleotide can comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl thiouridine, 5-carboxymethylaminomethyluracil, dihydrouracil, beta-D-galactosylqueosine, inosine,N6-isopentenyladenine, 1-methylguanine, 1-methylinosine, 2,2-dimethylguanine,2-methyladenine, 2-methylguanine, 3-methylcytosine, 5-methylcytosine, N6-adenine, 7-methylguanine, 5-methylaminomethyluracil, 5-methoxyaminomethyl-2α-thiouracil, beta-D-mannosylqueosine, 5'-methoxycarboxymethyluracil, 5-methoxyuracil, 2-methylthio-N&isopentenyladenine, uracil oxyacetic acid (y), wybutoxosine, pseudouracil, queosine, 2-thiocytosine, 5-methyl thiouracil, 2-thiouracil, 4-thiouracil, 5-methyluracil, -uracil-5-oxyacetic acid methylester, uracil oxyacetic acid (v), 5-methyl thiouracil, 3-(3-amino-3-N carboxypropyl) and 2,6-diaminopurine.

An oligonucleotide modulator of the invention can also comprise at least one modified sugar moiety selected from the group including, but not limited to, arabinose, 2-fluoroarabinose, xylose, and hexose.

In yet another embodiment, an oligonucleotide modulator can comprise at least one modified phosphate backbone selected from the group including, but not limited to, a phosphorothioate, a phosphorodithioate, a phosphoramidothioate, a phosphoramidate, a phosphorodiamidate, a methylphosphonate, an alkyl phosphotriester, and a formacetal or analog thereof.

Oligonucleotide modulators can be prepared that have desired characteristics, such as improved in vivo stability and/or improved delivery characteristics. Examples of such modifications include chemical substitutions at the sugar and/or backbone and/or base positions. Oligonucleotide modulators can contain nucleotide derivatives modified at the 5- and 2' positions of pyrimidines, for example, nucleotides can be modified with 2' amino, 2'-fluoro and/or 2'-O-methyl. Modifications of the modulating oligonucleotides of the invention can include those that provide other chemical groups that incorporate additional charge, polarization, hydrophobicity, hydrogen bonding and/or electrostatic interaction. Such modifications include but are not limited to 2' position sugar modifications, locked nucleic acids, 5 position pyrimidine modifications, 8 position purine modifications, modification at exocyclic amines, substitution of 4-thiouridine, substitution of 5-bromo or 5-iodo-uracil, backbone modifications, phosphorothioate or alkyl phosphate modifications, methylations, unusual base-pairing combinations such as isobases isocytidine and isoguanidine, etc. Modifications can also include 3' and 5' modifications, such as capping. (See also Manoharan, Biochem. Biophys. Acta 1489:117 (1999); Herdewija, Antisense Nucleic Acid Drug Development 10:297 (2000); Maier et al, Organic Letters 2:1819 (2000)).

Oligonucleotides of the invention can be synthesized by standard methods known in the art, e.g. by use of an automated DNA synthesizer (such as are commercially available from Biosearch, Applied Biosystems, etc.).

Using the instructions provided herein, one of ordinary skill can easily practice the invention to regulate any therapeutic nucleic acid by the timely administration of a complementary nucleic acid that terminates or otherwise modifies the activity of the therapeutic ligand. This technique can be used, for example, in connection with any of the nucleic acid ligands described or referred to in the patent documents cited above.

2. Ribozymes and DNAzymes

Likewise, using the instructions provided herein, one of ordinary skill can easily practice the invention to regulate any therapeutic nucleic acid ligand by the timely administration of a ribozyme or a DNAzyme.

Enzymatic nucleic acids act by first binding to a target RNA (or DNA, see Cech U.S. Pat. No. 5,180,818). Such binding occurs through the target binding portion of an enzymatic nucleic acid which is held in close proximity to an enzymatic portion of molecule that acts to cleave the target RNA. Thus, the enzymatic nucleic acid first recognizes and then binds a target RNA through complementary base-pairing, and once bound to the correct site, acts enzymatically to cut the target RNA. Cleavage of such a target RNA will destroy its ability to direct synthesis of an encoded protein. After an enzymatic nucleic acid has bound and cleaved its RNA target it is released from that RNA to search for another target and can repeatedly bind and cleave new targets thereby allowing for inactivation of RNA aptamers. There are at least five classes of ribozymes that each display a different type of specificity. For example, Group I Introns are ~300 to >1000 nucleotides in size and require a U in the target sequence immediately 5' of the cleavage site and binds 4-6 nucleotides at the 5'-side of the cleavage site. There are over 75 known members of this class, they are found in Tetrahymena thermophila rRNA, fungal mitochondria, chloroplasts, phage T4, blue-green algae, and others. Another class are RNaseP RNA (M1 RNA), which are ~290 to 400 nucleotides in size. They are the RNA portion of a ribonucleoprotein enzyme and cleave the tRNA precursors to form mature tRNA There are roughly 10 known members of this group and all are bacterial in origin. A third example are Hammerhead Ribozyme, which are ~30 to 40 nucleotides in size. They require the target sequence UH immediately 5' of the cleavage site and bind a variable number nucleotides on both sides of the cleavage site. There are at least 14 known members of this class that are found in a number of plant pathogens (virusoids) that use RNA as the infectious agent. A fourth class are the Hairpin Ribozymes, which are ~50 nucleotides in size. They requires the target sequence GUC immediately 3' of the cleavage site and bind 4 nucleotides at the 5'-side of the cleavage site and a variable number to the 3'-side of the cleavage site. There are found in one plant pathogen (satellite RNA of the tobacco ringspot virus) which uses RNA as the infectious agent. The fifth group are Hepatitis Delta Virus (HDV) Ribozymes, which are ~60 nucleotides in size.

The enzymatic nature of a ribozyme can be advantageous over other technologies, such as antisense technology, in certain applications since the effective concentration of ribozyme necessary to effect a therapeutic treatment can be less than that of an antisense oligonucleotide. This advantage reflects the ability of the ribozyme to act enzymatically. Thus, a single ribozyme molecule is able to cleave many molecules of target RNA aptamers. In addition, the ribozyme is a highly specific inhibitor, with the specificity of inhibition depending not only on the base pairing mechanism of binding, but also on the mechanism by which the molecule inhibits the expression of the RNA to which it binds. That is, the inhibition is caused by cleavage of the RNA target and so specificity is defined as the ratio of the rate of cleavage of the targeted RNA over the rate of cleavage of non-targeted RNA. This cleavage mechanism is dependent upon factors additional to those involved in base pairing. Thus, the specificity of action of a ribozyme, under certain circumstances, can be greater than that of antisense oligonucleotide binding the same RNA site.

Another class of catalytic molecules are called "DNAzymes". DNAzymes are single-stranded, and cleave both RNA and DNA. A general model for the DNAzyme has been proposed, and is known as the "10-23" model. DNAzymes following the "10-23" model, also referred to simply as "10-23 DNAzymes", have a catalytic domain of 15 deoxyribonucleotides, flanked by two substrate-recognition domains of seven to nine deoxyribonucleotides each. In vitro analyses show that this type of DNAzyme can effectively cleave its substrate RNA at purine:pyrimidine junctions under physiological conditions. As used herein, "DNAzyme" means a DNA molecule that specifically recognizes and cleaves a distinct target nucleic acid sequence, which may be either DNA or RNA.

Ribozymes and DNAzymes comprise both substrate binding domains and catalytic domains. Rules for the optimal design of the regulatory ribozymes can be found within Methods in Molecular Biology Volume 74 "Ribozyme Protocols" edited by Philip C. Turner (Humana Press, Totowa, N.J., 1997). Strategies to identify reactive sites for ribozymes within a targeted nucleic acid are also described in this volume. Using these standard rules, hammerhead ribozymes, hairpin ribozymes, hepatitis delta virus ribozymes and ribozymes derived from group I introns can be specifically engineered to bind to and cleave a target nucleic acid ligand. The ability of such ribozymes or DNAzymes to cleave the target nucleic acid ligand can be determined in any number of assays. For example, following incubation of a ribozyme or DNAzyme with an unlabeled or a labeled (eg. $^{32}$P) target nucleic acid ligand under conditions favoring reaction, the target nucleic acid can be analyzed by denaturing gel electrophoresis to determine if the ribozyme or DNAzyme cleaved the backbone of the target nucleic acid ligand Alternatively, fluorescence resonance energy transfer, or change in fluorescence intensity can be used to measure cleavage of an appropriately labeled nucleic acid ligand.

3. Polynucleic Acid Analogues (Peptide Nucleic Acids (PNAs), Morpholino Nucleic Acids (MNAs), Locked Nucleic Acids (LNAs)), and Pseudo-Cyclic Oligonucleotides (PCOs)

Nucleobases of the oligonucleotide modulators of the invention can be connected via internucleobase linkages, e.g., peptidyl linkages (as in the case of peptide nucleic acids (PNAs); Nielsen et al. (1991) Science 254, 1497 and U.S. Pat. No. 5,539,082) and morpholino linkages (Qin et al., Antisense Nucleic Acid Drug Dev. 10, 11 (2000); Summerton, Antisense Nucleic Acid Drug Dev. 7, 187 (1997); Summerton et al., Antisense Nucleic Acid Drug Dev. 7, 63 (1997); Taylor et al., J Biol. Chem. 271, 17445 (1996); Partridge et al., Antisense Nucleic Acid Drug Dev. 6, 169 (1996)), or by any other natural or modified linkage. The oligonucleobases can also be Locked Nucleic Acids (LNAs). Nielsen et al., J Biomol Struct Dyn 17, 175 (1999); Petersen et al., J Mol Recognit 13, 44 (2000); Nielsen et al., Bioconjug Chem 11, 228 (2000).

PNAs are compounds that are analogous to oligonucleotides, but differ in composition. In PNAs, the deoxyribose backbone of oligonucleotide is replaced with a peptide backbone. Each subunit of the peptide backbone is attached to a naturally-occurring or non-naturally-occurring nucleobase. PNA often has an achiral polyamide backbone consisting of N-(2-aminoethyl)glycine units. The purine or pyrimidine bases are linked to each unit via a methylene carbonyl linker (1-3) to target the complementary nucleic acid. PNA binds to complementary RNA or DNA in a parallel or antiparallel orientation following the Watson-Crick base-pairing rules. The uncharged nature of the PNA oligomers enhances the stability of the hybrid PNA/DNA(RNA) duplexes as compared to the natural homoduplexes. The non-natural character of the PNA makes PNA oligomers highly resistant to protease and nuclease attacks. These properties of PNA oligomers allow them to serve as efficient antisense or modulators of nucleic acid ligand activity. Indeed, peptide nucleic acids have been applied to block protein expression on the transcriptional and translational level, and microinjected PNA oligomers demonstrate a strong antisense effect in intact cells. See www.bioscience.org/1999/v4/d/soomets/fulltext.htm; and Frontiers in Bioscience, 4, d782-786 (Nov. 1, 1999) for details on recent achievements on PNA antisense application, especially these concerned with whole cell or tissue delivery of the PNA. See also Nielsen, P. E., Egholm. M., Berg, R. H. & Buchardt, O. (1993) Peptide nucleic acids (PNA). DNA analogues with a polyamide backbone. In "*Antisense Research and Application*" Crook, S. & Lebleu, B. (eds.) CRC Press, Boca Raton, pp 363-373.

PNAs bind to both DNA and RNA and form PNA/DNA or PNA/RNA duplexes. The resulting PNA/DNA or PNA/RNA duplexes are bound tighter than corresponding DNA/DNA or DNA/RNA duplexes as evidenced by their higher melting temperatures ($T_m$). This high thermal stability of PNA/DNA (RNA) duplexes has been attributed to the neutrality of the PNA backbone, which results elimination of charge repulsion that is present in DNA/DNA or RNA/RNA duplexes. Another advantage of PNA/DNA(RNA) duplexes is that $T_m$ is practically independent of salt concentration. DNA/DNA duplexes, on the other hand, are highly dependent on the ionic strength.

Since PNAs are an analogue of DNA in which the backbone is a pseudopeptide rather than a sugar, they mimic the behavior of DNA and bind complementary nucleic acid strands. Unnatural nucleobases, such as pseudo isocytosine, 5-methyl cytosine and 2,6-diaminopurine, among many others, also can be incorporated in PNA synthons. PNAs are most commonly synthesized from monomers (PNA synthons) protected according to the t-Boc/benzyl protection strategy, wherein the backbone amino group of the growing polymer is protected with the t-butyloxycarbonyl (t-Boc) group and the exocyclic amino groups of the nucleobases, if present, are protected with the benzyloxycarbonyl (benzyl) group. PNA synthons protected using the t-Boc/benzyl strategy are now commercially available.

PNA is both biologically and chemically stable and readily available by automated synthesis ((Hyrup, B., Egholm, M., Rolland, M., Nielsen, P. E., Berg, R. H. & Buchardt, O. (1993) Modification of the binding affinity of peptide nucleic acids (PNA). PNA with extended backbones consisting of 2-Aminoethyl-Alanine or 3-Aminopropylglycine units. *J. Chem. Soc. Chem. Commun.* 518-519); Demidov, V., Frank-Kamenetskii, M. D., Egholm, M., Buchardt, O. & Nielsen, P. E. (1993). Sequence selective double strand DNA cleavage by PNA targeting using nuclease S1. *Nucleic Acids Res.* 21, 2103-2107). These properties have made PNA very good lead for antisense gene therapeutic drugs, and in vitro studies have further substantiated the antisense potential (Nielsen, P. E. "Peptide Nucleic Acid (PNA) A model structure for the primordial genetic material" *Origins of Life* 1993, 23, 323-327; Egholm, M., Behrens, C., Christensen, L., Berg, R. H., Nielsen, P. E. & Buchardt, O. "Peptide nucleic acids containing adenine or guanine recognize thymine and cytosine in complementary DNA sequences" *J. Chem. Soc. Chem. Commun.* 1993, 800-801; Kim, S. K., Nielsen, P. E., Egholm, M., Buchardt, O., Berg, R. H. & Nordén, B. "Right-handed triplex formed between peptide nucleic acid PNA-$T_8$ and poly(dA) shown by linear and circular dichroism spectroscopy" *J. Amer. Chem. Soc.* 1993, 115, 6477-6481; Egholm, M., Buchardt, O., Christensen, L., Behrens, C., Freier, S. M., Driver, D. A., Berg, R. H., Kim, S. K., Nordén, B. & Nielsen, P. E. "PNA hybridizes to complementary oligonucleotides obeying the Watson-Crick hydrogen bonding rules" *Nature* 1993, 365, 556-568; Buchardt, O., Egholm, M., Berg, R. & Nielsen, P. E. "Peptide Nucleic Acids (PNA) and their potential applications in medicine and biotechnology" *Trends Biotechnology,* 1993, 11, 384-386).

PNAs appear to be the very useful for a number of special applications. When targeted against rare all-purine sequences, PNAs can block translation anywhere in a mRNA by forming a double-clamp structure. With such rare RNA sequences one segment of the PNA binds to the target sequence by Watson/Crick bonds and the other segment of the PNA binds to major-groove sites of the resulting PNA/RNA duplex. Probably because of their very flexible backbone structure, PNAs also readily form triple helix structures with rare duplex DNA sequences comprising mostly purines in one strand and mostly pyrimidines in the other strand. Lastly, under low salt conditions in cell-free systems PNAs have been shown to achieve sequence-specific invasion of duplex DNA sequences, resulting in inhibition of transcription of the invaded duplex.

Recent studies by several groups have shown that coupling of PNA to different carriers can improve their uptake into cells. Among these, "cellular uptake peptides," fatty acids or DNA, especially several peptide sequences have been shown to be able to carry PNA oligomers across the cell membranes. Vector peptide-PNA conjugates have been shown to cross the neuron membrane and suppress targeted mRNA (Aldrian-Herrada, G. et al. (1998) Nucleic Acid Res. 26:4920). Biotinylated PNA linked to a conjugate of steptavidin and the OX26 murine monoclonal antibody to the rat transferrin receptor have been reported to cross the rat blood-brain barrier in vivo (Pardridge, W. et al. 1995 PNAS 92:5592-5596). Chinnery, P. F. et al. attached the presequence peptide of the nuclear-encoded human cytochrome c oxidase (COX) subunit VIII to biotinylated PNA which was successfully imported into isolated mitochondria in vitro (Chinnery, P. F. et al. 1999 Gene Ther. 6:1919-28). Delivery of the biotinylated peptide-PNA to mitochondria in intact cells was confirmed by confocal microscopy. In addition, a short hydrophobic peptide with the sequence biotinyl-FLFL coupled to a PNA trimer has been shown to internalize into human erythrocytes and Namalwa cells (Scarfi, S., A. Gasparini, G. Damonte & U. Benatti: Synthesis, uptake, and intracellular metabolism of a hydrophobic tetrapeptide-peptide nucleic acid (PNA)-biotin molecule. *Biochem Biophys Res Comnizin* 1997, 236, 323-326). Basu and Wickström (Synthesis and characterization of a peptide nucleic acid conjugated to a D-peptide analog of insulin-like growth factor 1 for increased cellular uptake. *Bioconjugate Chem* 1997, 8, 481-488) showed that PNA conjugated to an all-D-amino acid insulin-like growth factor 1 (IGF1) mimicking peptide was specifically taken up by cells expressing the IGF1 receptor, although no antisense activity was described.

For some examples of other works, see Nielsen, P. E., M. Egholm, R. H. Berg & O. Buchardt: Sequence-selective recognition of DNA by strand displacement with a thymine-substituted polyamide. *Science* 254, 1497-1500 (1991); Egholm, M., O. Buchart, P. E. Nielsen & R. H. Berg: Peptide nucleic acids (PNA). Oligonucleotide analogues with an achiral peptide backbone. *J Am Chem Soc* 114, 1895-1897 (1992); Nielsen, P. E., M. Egholm & O. Buchardt: Peptide nucleic acid (PNA). A DNA mimic with a peptide backbone. *Bioconjugate Chemistry* 5, 3-7 (1994); Egholm, M., P. E. Nielsen, O. Buchardt & R. H. Berg: Recognition of guanine and adenine in DNA by cytosine and thymine containing peptide nucleic acid. *J Am Chem Soc* 114, 9677-9678 (1992); Egholm, M., O. Buchardt, L. Christensen, C. Behrens, S. M. Freier, D. A. Driver, R. H. Berg, S. K. Kim, B. Norden & P. E. Nielsen: PNA hybridizes to complementary oligonucleotides obeying the Watson-Crick hydrogen-bonding rules [see comments]. *Nature* 365, 566-568 (1993); Wittung, P., P. E. Nielsen, O. Buchardt, M. Egholm & B. Nordén: DNA-like double helix formed by peptide nucleic acid. *Nature* 368, 561-563 (1994); Brown, S. C., S. A. Thomson, J. M. Veal & D. G. Davis: NMR solution structure of a peptide nucleic acid complexed with RNA. *Science* 265, 777-780 (1994); Demidov, V. V., V. N. Potaman, M. D. Frank-Kamenetskii, M. Egholm, O. Buchard, S. H. Sönnichsen & P. E. Nielsen: Stability of peptide nucleic acids in human serum and cellular extracts. *Biochemical Pharmacology* 48, 1310-1313 (1994); Peffer, N. J., J. C. Hanvey, J. E. Bisi, S. A. Thomson, C. F. Hassman, S. A. Noble & L. E. Babiss: Strand-invasion of duplex DNA by peptide nucleic acid oligomers. *Proc Nat Acad Sci USA* 90, 10648-10652 (1993).

U.S. Pat. No. 6,046,307 to Shay et al. discloses PNAs that inhibit telomerase activity in mammalian cells. U.S. Pat. No. 5,789,573 to Baker et al. disclose compositions and methods for inhibiting the translation of capped targeted mRNA using PNAs. U.S. Pat. No. 6,165,720 disclose labeling of the PNA complex.

One can easily prepare a PNA or MNA that is complementary at least in part to a nucleic acid ligand using the same rules of complementarity and Watson Crick base-pairing as is used in the preparation of conventional oligonucleotide antisense molecules.

Morpholino nucleic acids are so named because they are assembled from morpholino subunits, each of which contains one of the four genetic bases (adenine, cytosine, guanine, and thymine) linked to a 6-membered morpholine ring. Eighteen to twenty-five subunits of these four subunit types are joined in a specific order by non-ionic phosphorodiamidate intersubunit linkages to give a morpholino oligo. These morpholino oligos, with their 6-membered morpholine backbone moieties joined by non-ionic linkages, afford substantially better antisense properties than do RNA, DNA, and their analogs having 5-membered ribose or deoxyribose backbone moieties joined by ionic linkages (see wwwgene-tools.com/Morpholinos/body_morpholinos.HTML).

Morpholinos, devised by Summerton in 1985, constitute a radical redesign of natural nucleic acids, with the potential advantages of low cost starting materials and inexpensive assembly. Like PNAs, morpholinos are completely resistant to nucleases and they appear to be free of most or all of the non-antisense effects that are seen with S-DNAs. In contrast to PNAs, most morpholinos exhibit excellent aqueous solubility. Morpholinos also have much higher RNA binding affinities than do S-DNAs, though not as high as PNAs. Probably as a result of their substantial RNA binding affinities, long morpholinos (25-mers) provide predictable targeting and very high efficacy. Most notable, morpholinos provide good sequence specificity. The same factors that underlie their exceptional sequence specificity also render them unsuitable for targeting point mutations.

U.S. Pat. No. 6,153,737 to Manoharan et al. is directed to derivatized oligonucleotides wherein the linked nucleosides are functionalized with peptides, proteins, water soluble vitamins or lipid soluble vitamins. This disclosure was directed towards antisense therapeutics by modification of oligonucleotides with a peptide or protein sequence that aids in the selective entry of the complex into the nuclear envelope. Similarly, water-soluble and lipid-soluble vitamins can be used to assist in the transfer of the anti-sense therapeutic or diagnostic agent across cellular membranes.

The efficient and sequence specific binding to RNA or DNA combined with very high biological stability makes PNAs and MNAs extremely attractive leads for the development of modulators of the present invention. Peptide nucleic acids which can be conjugated to the carriers are distinguished in U.S. Pat. No. 5,864,010 entitled Peptide Nucleic Acid Combinatorial Libraries and Improved Methods of Synthesis, developed by ISIS Pharmaceuticals, which is hereby incorporated by reference. In addition, the peptide nucleic acids which can be conjugated to the carriers of the present invention are distinguished in U.S. Pat. No. 5,986,053 entitled peptide nucleic acids complexes of two peptide nucleic acid strands and one nucleic acid strand.

LNA is a novel class of DNA analogues that possess some features that make it a prime candidate for modulators of the invention. The LNA monomers are bi-cyclic compounds structurally similar to RNA-monomers. LNA share most of the chemical properties of DNA and RNA, it is water-soluble, can be separated by gel electrophoreses, ethanol precipitated etc (Tetrahedron, 54, 3607-3630 (1998)). However, introduction of LNA monomers into either DNA or RNA oligos results in high thermal stability of duplexes with complementary DNA or RNA, while, at the same time obeying the Watson-Crick base-pairing rules. This high thermal stability of the duplexes formed with LNA oligomers together with the finding that primers containing 3' located LNA(s) are substrates for enzymatic extensions, e.g. the PCR reaction, is used in the present invention to significantly increase the specificity of detection of variant nucleic acids in the in vitro assays described in the application. The amplification processes of individual alleles occur highly discriminative (cross reactions are not visible) and several reactions may take place in the same vessel. See for example U.S. Pat. No. 6,316,198.

Pseudo-cyclic oligonucleobases (PCOs) can also be used as a modulator in the present invention (see U.S. Pat. No. 6,383,752). PCOs contain two oligonucleotide segments attached through their 3'-3' or 5'-5' ends. One of the segments (the "functional segment") of the PCO has some functionality (e.g., an antisense oligonucleotide complementary to a target mRNA). Another segment (the "protective segment") is complementary to the 3'- or 5'-terminal end of the functional segment (depending on the end through which it is attached to the functional segment). As a result of complementarity between the functional and protective segment segments, PCOs form intramolecular pseudo-cyclic structures in the absence of the target nucleic acids (e.g., RNA). PCOs are more stable than conventional antisense oligonucleotides because of the presence of 3'-3' or 5'-5' linkages and the formation of intramolecular pseudo-cyclic structures. Pharmacokinetic, tissue distribution, and stability studies in mice suggest that PCOs have higher in vivo stability than and, pharmacokinetic and tissue distribution profiles similar to, those of PS-oligonucleotides in general, but rapid elimination from selected tissues. When a fluorophore and quencher molecules are appropriately linked to the PCOs of the present invention, the molecule will fluoresce when it is in the linear configuration, but the fluorescence is quenched in the cyclic conformation.

A. Nucleic Acid Binding Peptides, Polypeptides or Proteins

Protein-nucleic acid interactions are involved in many cellular functions, including transcription, RNA splicing, and translation. Synthetic molecules that can bind with high affinity to specific sequences of single-stranded nucleic acids have the potential to interfere with these interactions in a controllable way.

Many proteins have been identified that can bind directly to nucleic acid sequences. One main group of proteins that directly bind to DNA are transcription factors. Some examples of transcription factors fall into the following classes: Basic domain transcription factors (leucine-zipper factors, CREB, helix-loop-helix factors, helix-loop-helix/leucine zipper factors, cell-cycle controlling factors, NF-1, RF-X, bHSH), Zinc-coordinating DNA binding domain transcription factors (cys4 zinc finger of nuclear receptor type, thyroid hormone receptor-like factors, diverse Cys4 zinc fingers, Cys2His2 zinc finger domain, metabolic regulators in fungi, large factors with NF-6B-like binding properties, cys6 cysteine-zinc cluster, zinc fingers of alternating composition, homeo domain), Helix-turn-helix (homeo domain only, POU domain factors, paired box, fork head/winged helix, heat shock factors, tryptophan clusters, TEA domain), beta-Scaffold Factors with minor groove contacts (RHR, STAT, p53, MADS box, beta-Barrel alpha-helix transcription factors, TATA-binding proteins, HMG, heteromeric CCAAT factors, grainyhead, cold-shock domain factors, runt), Other transcription factors (copper fist proteins, HMGI(Y), Pocket domain, E1 A-like factors, AP2/EREBP-related factors).

In addition to its primary structure, RNA has the ability to fold into complex tertiary structures consisting of such local motifs as loops, bulges, pseudoknots, and turns. It is not surprising that, when they occur in RNAs that interact with proteins, these local structures are found to play important roles in protein-RNA interactions. This diversity of local and tertiary structure, however, makes it impossible to design synthetic agents with general, simple-to-use recognition rules analogous to those for the formation of double- and triple-helical nucleic acids. Tripeptides have been identified that are able to specifically bind to tertiary structures of nucleic acids (Hwang et al., Proc. Natl. Acad. Sci. USA 96:12997 (1999)). Thus, in one embodiment, these tripeptides may be used as modulators of nucleic acid ligand activity.

Peptide-based modulators of nucleic acid ligands represent an alternative molecular class of modulators to oligonucleotides or their analogues. This class of modulators are particularly prove useful when sufficiently active oligonucleotide modulators of a target nucleic acid ligand can not be isolated due to the lack of sufficient single-stranded regions to promote nucleation between the target and the oligonucleotide modulator. In addition, peptide modulators provide different bioavailabilities and pharmacokinetics than oligonucleotide modulators, and therefore, for some target nucleic acid ligands may be preferable.

Several strategies to isolate peptides capable of binding to and thereby modulating the activity of a target nucleic acid ligand are available. For example, encoded peptide combinatorial libraries immobilized on beads have been described, and have been demonstrated to contain peptides able to bind viral RNA sequences and disrupt the interaction between the viral RNA and a viral regulatory protein that specifically binds said RNA (Hwang et al., Proc Natl Acad Sci USA 96:12997 (1999)). Using such libraries, modulators of nucleic acid ligands can be isolated by appending a label (eg. Dye) to the target nucleic acid ligand and incubating together the labeled-target and bead-immobilized peptide library under conditions in which binding between some members of the library and the nucleic acid are favored. The binding of the nucleic acid ligand to the specific peptide on a given bead causes the bead to be "colored" by the label on the nucleic acid ligand, and thus enables the identification of peptides able to bind the target but simple isolation of the bead. The direct interaction between peptides isolated by such screening methods and the target nucleic acid ligand can be confirmed and quantified using any number of the binding assays described to identify modulators of nucleic acid ligands. The ability of said peptides to modulate the activity of the target nucleic acid ligand can be confirmed in appropriate bioassays.

As another strategy, the target nucleic acid ligand can be immobilized on a solid support (eg plastic, bead etc) by appending the appropriate affinity handle (eg biotin for streptavidin coated surfaces) or reactive site (eg. Aliphatic amine) to either end of the target nucleic acid ligand during chemical synthesis. Alternatively, biotinylated RNA or RNA containing the desired modification can be prepared according to standard transcription protocols, but including a 5-fold molar excess of a 5'-biotin-modified GMP or otherwise modified GMP over GTP in the reaction mixture. Methods for synthesizing 5'-biotin-modified guanosine nucleotides and additional guanosine nucleotide derivatives and incorporating said GMP derivatives into in vitro transcripts are described in WO 98/30720 entitled "Bioconjugation of Oligonucleotides". Once the target RNA has been immobilized on a surface, peptides capable of binding said target RNA can be isolated by screening combinatorial peptide libraries, for example, random phage display libraries for peptides capable of binding the target nucleic acid ligand using standard methods for screening phage display libraries. Once isolated, the direct interaction between peptides and the target nucleic acid ligand can be confirmed and quantified using any number of the binding assays described to identify potential modulators of nucleic acid ligands. The ability of said peptides to modulate the activity of the target nucleic acid ligand can be confirmed in appropriate bioassays.

In addition, the mass spectral assays described can be used to screen amino acid and small molecular weight peptide libraries to identify those capable of binding to the target nucleic acid ligand (see U.S. Pat. Nos. 6,342,393; 6,329,146; 6,253,168; and 6,221,587). Once identified, the direct interaction between such agents and the target nucleic acid ligand can be confirmed and quantified using any number of the binding assays described to identify potential modulators of nucleic acid ligands. The ability of said peptides to modulate the activity of the target nucleic acid ligand can be confirmed in appropriate bioassays.

In addition, U.S. Pat. Nos. 5,834,184, 5,786,145 and 5,770,434 disclose methods for generating and screening for peptide modulators of the invention.

Natural RNA binding proteins often have one domain responsible for RNA binding and other domains responsible for other functions. The domain responsible for RNA binding can sometimes be recognized by a characteristic motif. The most widely found RNA recognition sequence or binding motif is the RNP motif. The RNP motif is a 90-100 amino acid sequence that is present in one or more copies in proteins that bind pre mRNA, mRNA, pre-ribosomal RNA and snRNA. The consensus sequence and the sequences of several exemplary proteins containing the RNP motif are provided by Burd and Dreyfuss, Science 265, 615-621 (1994). See also Swanson et al., Trends Biochem. Sci. 13, 86 (1988); Bandziulis et al., Genes Dev. 3,431 (1989); Kenan et al., Trends Biochem. Sci. 16, 214 (1991). The consensus motif contains two short consensus sequences RNP-1 and RNP-2. Some RNP proteins bind specific RNA sequences with high affinities (dissociation constant in the range of $10^{-8}$-$10^{-11}$ M). Such proteins often function in RNA processing reactions. Other RNP proteins have less stringent sequence requirements and bind less strongly (dissociation constant ~$10^{-6}$-$10^{-7}$ M). Burd & Dreyfuss, EMBO J. 13, 1197 (1994).

A second characteristic RNA binding motif found in viral, phage and ribosomal proteins is an arginine-rich motif (ARM) of about 10-20 amino acids. RNA binding proteins having this motif include the HIV Tat and Rev proteins. Rev binds with high affinity disassociation constant ($10^{-9}$ M) to an RNA sequence termed RRE, which is . found in all HIV mRNAs. Zapp et al., Nature 342, 714 (1989); Dayton et al., Science 246, 1625 (1989). Tat binds to an RNA sequence termed TAR with a dissociation constant of $5 \times 10^{-9}$ M. Churcher et al., J. Mol. Biol. 230, 90 (1993). For Tat and Rev proteins, a fragment containing the arginine-rich motif binds as strongly as the intact protein. In other RNA binding proteins with ARM motifs, residues outside the ARM also contribute to binding. Other families of RNA binding proteins with different binding motifs are described by Burd and Dreyfuss, supra.

B. Oligosaccharides

Oligosaccharides can interact with nucleic acids. The antibiotic aminoglycosides are products of *Streptomyces* species and are represented by streptomycin, kanamycin, tobramycin, neomycin, netilmicin, amikacin and gentamicin. These antibiotics exert their activity by binding to bacterial ribosomes and preventing the initiation of protein synthesis. Aminoglycoside antibiotics interact specifically with diverse RNA molecules such as various ribozymes and the HIV-1's TAR and RRE sequences. Aminoglycoside antibiotics that bind to the 30s ribosomal A-site RNA cause misreading of the genetic code and inhibit translocation. The aminoglycoside antibiotic paromomycin binds specifically to the RNA oligonucleotide at the 30S A site. This antibiotic binds the major groove on the A-site RNA within a pocket created by an A-A pair and a single bulged adenine. There are several interactions that occur between the aminoglycoside chemical groups and the conserved nucleotides in the RNA.

Thus, oligosaccharides, like aminoglycosides, can bind to nucleic acids and can be used to modulate the activity of nucleic acid ligands. In addition, the mass spectral assays described can be used to screen for oligosaccharides (e.g., aminoglycosides), alone or in a mixture, that are capable of binding to the target nucleic acid ligand (see U.S. Pat. Nos. 6,342,393; 6,329,146; 6,253,168; and 6,221,587).

D. Small Molecules

A small molecule that intercalates between the nucleic acid ligand and the target or otherwise disrupts or modifies the binding between the nucleic acid ligand and target can also be used as the therapeutic regulator.

Such small molecules can be identified by screening candidates in an assay that measures binding changes between the nucleic acid ligand and the target with and without the small molecule, or by using an in vivo or in vitro assay that measures the difference in biological effect of the nucleic acid ligand for the target with and without the small molecule.

Once a small molecule is identified that exhibits the desired effect, techniques such as combinatorial approaches can be used to optimize the chemical structure for the desired regulatory effect.

Assays suitable for use in screening small molecules are described in U.S. Pat. No. 5,834,199 and in further detail below. In addition, the mass spectral assays described can be used to screen small molecule libraries to identify those capable of binding to the target nucleic acid ligand (see U.S. Pat. Nos. 6,342,393; 6,329,146; 6,253,168; and 6,221,587).

E. Chimeras, Fusion Products and Otherwise Linked Materials

The oligonucleotides or analogues thereof (including ribozymes or DNAzymes or peptide nucleic acids (PNAs) or mopholino nucleic acids (MNAs)), nucleic acid binding peptides, polypeptides or proteins (including nucleic acid binding tripeptides, oligosaccharides, and small molecules can be combined covalently or noncovalently to provide a combination regulator as desired. In one example, an oligonucleotide, PNA or MNA can be linked to a peptide or protein to provide desired properties or therapeutic effect. Alternatively, an oligonucleotide or analogue thereof or peptide or protein can be linked to a small molecule to enhance its properties. These materials can be directly linked or linked via a spacer group as well known to those skilled in the art. In one embodiment, the small molecule includes a radioligand or other detectable agent that can be monitored using standard techniques. In this way, the progress and location of the regulator can be monitored. Alternatively, the small molecule is a therapeutic that is brought to the site of therapy by the regulator, and then optionally cleaved to provide its therapeutic effect at the appropriate location. In a third embodiment, the small molecule is a chelator that joins two biological materials together to produce a combined effect.

The chimeras, fusion products or otherwise multicomponent regulator can be identified and evaluated for therapeutic efficacy as described in detail below.

III. Identification and Selection of the Modulator

Standard binding assays can be used to identify and select modulators of the invention. Nonlimiting examples are gel shift assays and BIACORE assays. That is, test modulators can be contacted with the nucleic acid ligands to be targeted under test conditions or typical physiological conditions and a determination made as to whether the test modulator in fact binds the nucleic acid ligand. Test modulators that are found to bind the nucleic acid ligand can then be analyzed in an appropriate bioassay (which will vary depending on the aptamer and its target molecule, for example coagulation tests) to determine if the test modulator can affect the biological effect caused by the nucleic acid ligand on its target molecule.

The Gel-Shift assay is a technique used to assess binding capability. For example, a DNA fragment containing the test sequence is first incubated with the test protein or a mixture containing putative binding proteins, and then separated on a gel by electrophoresis. If the DNA fragment is bound by protein, it will be larger in size and its migration will therefore be retarded relative to that of the free fragment. For example, one method for a electrophoretic gel mobility shift assay can be (a) contacting in a mixture a nucleic acid binding protein with a non-radioactive or radioactive labeled nucleic acid molecule comprising a molecular probe under suitable conditions to promote specific binding interactions between the protein and the probe in forming a complex, wherein said probe is selected from the group consisting of dsDNA, ssDNA, and RNA; (b) electrophoresing the mixture; (c) transferring, using positive pressure blot transfer or capillary transfer, the complex to a membrane, wherein the membrane is positively charged nylon; and (d) detecting the complex bound to the membrane by detecting the non-radioactive or radioactive label in the complex.

The Biacore technology measures binding events on the sensor chip surface, so that the interactant attached to the surface determines the specificity of the analysis. Testing the specificity of an interaction involves simply analyzing whether different molecules can bind to the immobilized interactant. Binding gives an immediate change in the surface plasmon resonance (SPR) signal, so that it is directly apparent whether an interaction takes place or not. SPR-based biosensors monitor interactions by measuring the mass concentration of biomolecules close to a surface. The surface is made specific by attaching one of the interacting partners. Sample containing the other partner(s) flows over the surface: when molecules from the sample bind to the interactant attached to the surface, the local concentration changes and an SPR response is measured. The response is directly proportional to the mass of molecules that bind to the surface.

SPR arises when light is reflected under certain conditions from a conducting film at the interface between two media of different refractive index. In the Biacore technology, the media are the sample and the glass of the sensor chip, and the conducting film is a thin layer of gold on the chip surface. SPR causes a reduction in the intensity of reflected light at a specific angle of reflection. This angle varies with the refractive index close to the surface on the side opposite from the reflected light. When molecules in the sample bind to the sensor surface, the concentration and therefore the refractive index at the surface changes and an SPR response is detected. Plotting the response against time during the course of an interaction provides a quantitative measure of the progress of the interaction. The Biacore technology measures the angle of minimum reflected light intensity. The light is not absorbed by the sample: instead the light energy is dissipated through SPR in the gold film. SPR response values are expressed in resonance units (RU). One RU represents a change of 0.0001° in the angle of the intensity minimum. For most proteins, this is roughly equivalent to a change in concentration of about 1 pg/mm2 on the sensor surface. The exact conversion factor between RU and surface concentration depends on properties of the sensor surface and the nature of the molecule responsible for the concentration change.

There are a number of other assays that can determine whether an oligonucleotide or analogue thereof, peptide, polypeptide, oligosaccharide or small molecule can bind to the nucleic acid ligand in a manner such that the interaction with the target is modified. For example, electrophoretic mobility shift assays (EMSAs), titration calorimetry, scintillation proximity assays, sedimentation equilibrium assays using analytical ultracentrifugation (see for eg. www.cores.utah.edu/interaction), fluorescence polarization assays, fluorescence anisotropy assays, fluorescence intensity assays, fluorescence resonance energy transfer (FRET) assays, nitrocellulose filter binding assays, ELISAs, ELONAs (see, for example, U.S. Pat. No. 5,789,163), RIAs, or equilibrium dialysis assays can be used to evaluate the ability of an agent to bind to a nucleic acid ligand. Direct assays in which the interaction between the agent and the nucleic acid ligand is directly determined can be performed, or competition or displacement assays in which the ability of the agent to displace the nucleic acid ligand from its target can be performed (for example, see Green, Bell and Janjic, Biotechniques 30(5), 2001, p 1094 and U.S. Pat. No. 6,306,598). Once a candidate modulating agent is identified, its ability to modulate the activity of a nucleic acid ligand for its target can be confirmed in a bioassay. Alternatively, if an agent is identified that can modulate the interaction of a nucleic acid ligand with its target, such binding assays can be used to verify that the agent is interacting directly with the nucleic acid ligand and can measure the affinity of said interaction.

In another embodiment, mass spectrometry can be used for the identification of an regulator that binds to a nucleic acid ligand, the site(s) of interaction between the regulator and the nucleic acid ligand, and the relative binding affinity of agents for the nucleic acid ligand (see for example U.S. Pat. No. 6,329,146, Crooke et al). Such mass spectral methods can also be used for screening chemical mixtures or libraries, especially combinatorial libraries, for individual compounds that bind to a selected target nucleic acid ligand that can be used in as modulators of the nucleic acid ligand. Furthermore, mass spectral techniques can be used to screen multiple target nucleic acid ligands simultaneously against, e.g. a combinatorial library of compounds. Moreover, mass spectral techniques can be used to identify interaction between a plurality of molecular species, especially "small" molecules and a molecular interaction site on a target nucleic acid ligand.

In vivo or in vitro assays that evaluate the effectiveness of a regulator in modifying the interaction between a nucleic acid ligand and a target are specific for the disorder being treated. There are ample standard assays for biological properties that are well known and can be used. Examples of biological assays are provided in the patents cited in this application that describe certain nucleic acid ligands for specific applications.

As a nonlimiting example, coagulation tests can be performed as bioassays in clinical laboratories. These tests are generally functional end-point assays, in which a patient sample (plasma or whole blood) is incubated with exogenous reagents that activate the coagulation cascade, and the time until clot formation is measured. The clotting time of the patient sample is then compared to the clotting time of pooled normal plasma or whole blood to provide a standard measurement of the patient's hemostatic status. As described below, such clotting assays are commonly used as screening tests that evaluate the functioning of both the patient's intrinsic and extrinsic coagulation systems.

The Activated Clotting Time Test (ACT) is a screening test that resembles the activated partial thromboplastin time (APTT) test, but is performed using fresh whole blood samples. ACT can be used to monitor a patient's coagulation status in connection with clinical procedures, such as those that involve the administration of high doses of heparin (e.g., CPB and PTCA).

The Activated Partial Thromboplastin Time Test (APTT) is a common central laboratory test, APTT is used to evaluate the intrinsic coagulation pathway, which includes factors I, II, V, VIII, IX, X, XI, and XII. The test is performed using a plasma sample, in which the intrinsic pathway is activated by the addition of phospholipid, an activator (ellagic acid, kaolin, or micronized silica), and $Ca^{2+}$. Formation of the Xase and prothrombinase complexes on the surface of the phospholipid enables prothrombin to be converted into thrombin, with subsequent clot formation. The result of the APTT test is the time (in seconds) required for this reaction. APTT can be used to assess the overall competence of a patient's coagulation system, as a preoperative screening test for bleeding tendencies, and as a routine test for monitoring heparin therapy. Another example of the APTT is performed as follows. First, blood plasma is collected after the blood was subjected to centrifugal separation, and then acting is added thereto. In addition, calcium chloride is added. The period of time is measured until coagulation is formed More in detail, the blood plasma is stored in a refrigerator after it was obtained through centrifugal separation of blood. Activating agent of 0.1 ml, which was warmed in a water having a temperature of 37° C. for a minute, is poured into a test tube containing 0.1 ml of the plasma The mixture is allowed to stay in a water of 37° C. for two minutes. Then to this mixture, 0.1 ml of $CaCl_2$ of 0.02 M, which had been placed in a water having a temperature of 37° C., is added under pressure. At this moment a stop watch is switched on. The test tube is heated in the water of 37° C. for 25 seconds. The test tube is taken out, and if coagulation is observed, the stop watch is turned off. This is one way in which the blood coagulating time can be measured.

The bleeding time test can be used for the diagnosis of hemostatic dysfunction, von Willebrand's disease, and vascular disorders. It also can be used to screen for platelet abnormalities prior to surgery. The test is performed by making a small incision on the forearm and wicking away the blood from the wound site. The time it takes for bleeding to stop is recorded and in control subjects is approximately 3.5 minutes. Prolongation of the bleeding time is indicative of qualitative or quantitative platelet defects.

The Prothrombin Time Test (PT), which was first described by Quick in 1935, measures the tissue factor-induced coagulation time of blood or plasma. It is used as a screening test to evaluate the integrity of the extrinsic coagulation pathway, and is sensitive to coagulation factors I, II, V, VII, and X. The test can be performed by adding thromboplastin and $Ca^{2+}$ to a patient sample and measuring the time for clot formation. A prolonged clotting time suggests the presence of an inhibitor to, or a deficiency in, one or more of the coagulation factors of the extrinsic pathway. But PT clotting time can also be prolonged for patients on warfarin therapy, or for those with vitamin K deficiency or liver dysfunction. The PT test can provide an assessment of the extrinsic coagulation pathway, and is widely used to monitor oral anticoagulation therapy.

The Thrombin Clotting Time Test (TCT) measures the rate of a patient's clot formation compared to that of a normal plasma control. The test can be performed by adding a standard amount of thrombin to a patient's plasma that has been depleted of platelets, and measuring the time required for a clot to form. This test has been used as an aid in the diagnosis of disseminated intravascular coagulation (DIC) and liver disease.

There are also a number of tests that can be used in the diagnosis of a patient's coagulative status. These fall into two categories: complex tests, some of which are based on the screening tests outlined above, and immunoassays. Complex Tests include specific factor assays based on laboratory tests, such as the APTT, PT, and TCT tests. One assay measures the level of the activation peptide factor IXa or the factor IXa-antithrombin III complex. These measurements are used to determine the levels of factor IXa or factor VII-tissue mediated complex. Assays for activated protein C resistance, antithrombin, protein C deficiency, and protein S deficiency are also part of this group. Asymptomatic individuals who have heterogeneous deficiencies of proteins C and S, and resistance to activated protein C, have significantly elevated levels of the prothrombin fragment F1.2 compared to controls.

V. Method of Regulating Nucleic Acid Ligand Therapy

A method of modulating biological activity is provided that includes (i) administering to a patient in need thereof a nucleic acid ligand that binds to a target to produce a therapeutic effect, and then at the selected or desired time, (ii) administering to the patient a modulator that modifies the therapeutic effect. In one case, the modulator turns off the therapeutic effect. In another embodiment, the modulator reduces or minimizes but does not terminate the therapeutic effect. In yet another embodiment, the modulator enhances the therapeutic effect.

The base therapeutic effect is determined by the target and the nucleic acid ligand. The modification of the therapeutic effect is determined by the modulator. Any known or developed nucleic acid ligand can be regulated in accordance with this invention.

In one embodiment, the method comprises: (a) administering to a patient, including any warm-blooded vertebrate in need thereof, an effective amount of a nucleic acid ligand or DNA aptamer that selectively binds a coagulation pathway factor, the RNA aptamer having a dissociation constant for the coagulation pathway factor of about 20 nM or less; (b) modulating the biological activity of the coagulation pathway factor in the warm-blooded vertebrate through the administering of the RNA aptamer in step (a); and (c) providing an antidote to reverse the effects of the aptamer by administration of a modulator. For example, the modulators of the present invention can bind to nucleic acid ligands that target tissue factor (TF)/factor VIIa (FVIIa), factor VIIIa (FVIIIa)/factor IXa (FIXa), factor Va (FVa/factor Xa (Fxa) enzyme complexes and platelet receptors such as gp IIbIIIa and gp IbIX and modulate the effects of the nucleic acid ligand. This invention also provides antidote control of platelet inhibitors, antithrombotics and fibrinolytics.

At least three clinical scenarios exist in which the ability to rapidly reverse the activity of an antithrombotic or anticoagulant nucleic acid ligand is desirable. The first case is when anticoagulant or antithrombotic treatment leads to hemorrhage, including intracranial or gastrointestinal hemorrhage. While identifying safer target proteins may reduce this risk, the potential for morbidity or mortality from this type of bleeding event is such that the risk can not be overlooked. The second case is when emergency surgery is required for patients who have received antithrombotic treatment. This clinical situation arises in a low percentage of patients who require emergency coronary artery bypass grafts while undergoing percutaneous coronary intervention under the coverage of GPIIb/IIIa inhibitors. Current practice in this situation is to allow for clearance of the compound (for small molecule antagonists such as eptifibatide), which may take 2-4 hours, or platelet infusion (for Abciximab treatment). The third case is when an anticoagulant nucleic acid ligand is used during a cardiopulmonary bypass procedure. Bypass patients are predisposed to post operative bleeding. In each case, acute reversal of the anticoagulant effects of a compound via an antidote (e.g., an oligonucleotide modulator of the invention targeted to an anticoagulant or antithrombotic nucleic acid ligand) allows for improved, and likely safer, medical control of the anticoagulant or antithrombotic compound.

A method of treating cardiovascular disease in patients is also provided in accordance with the present invention. The method comprises administering an effective amount of an RNA aptamer that selectively binds a coagulation pathway factor, the RNA aptamer having a dissociation constant for the coagulation pathway factor of about 20 nM or less, to a vertebrate subject suffering from cardiovascular disease, whereby cardiovascular disease in the vertebrate subject is treated, then providing an antidote to reverse the effects of the aptamer by administration of a modulator.

A method of modulating E2F activity in patient, including a warm-blooded vertebrate, in which such modulation is desired is also provided. The method comprises: (a) administering to the warm-blooded vertebrate an effective amount of an RNA aptamer that selectively binds an E2F family member, the RNA aptamer having a dissociation constant for the E2F family member of about 20 nM or less; (b) modulating E2F in the warm-blooded vertebrate through the administering of the RNA aptamer of step (a); and (c) providing an antidote to reverse the effects of the aptamer by administration of a modulator.

The patient treated in the present invention in its many embodiments is desirably a human patient, although it is to be understood that the principles of the invention indicate that the invention is effective with respect to all vertebrate species, including warm-blood vertebrates (e.g., birds and mammals), which are intended to be included in the term "patient". In this context, a mammal is understood to include any mammalian species in which treatment of cardiovascular disease is desirable, particularly agricultural and domestic mammalian species.

Contemplated is the treatment of mammals such as humans, as well as those mammals of importance due to being endangered (such as Siberian tigers), of economical importance (animals raised on farms for consumption by humans and/or social importance (animals kept as pets or in zoos) to humans, for instance, carnivores other than humans such as cats and dogs), swine (pigs, hogs, and wild board), ruminants (such as cattle, oxen, sheep, giraffes, deer goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans.

The present method for treating cardiovascular disease in a tissue contemplates contacting a tissue in which cardiovascular disease is occurring, or is at risk for occurring, with a composition comprising a therapeutically effective amount of an RNA aptamer capable of binding a coagulation factor as well as providing an antidote to reverse the effects of the aptamer by administration of a modulator. Thus, the method comprises administering to a patient a therapeutically effective amount of a physiologically tolerable composition containing the RNA aptamer as well as a method to provide an antidote to reverse the effects of the aptamer by administration of a modulator.

The dosage ranges for the administration of the modulator depend upon the form of the modulator, and its potency, as described further herein, and are amounts large enough to produce the desired effect. For situations in which coagulation is modulated, which can correspondingly ameliorate cardiovascular disease and the symptoms of cardiovascular disease, the dosage should not be so large as to cause adverse side effects, such as hyperviscosity syndromes, pulmonary edema, congestive heart failure, and the like. Generally, the dosage will vary with the age, condition, sex and extent of the disease in the patient and can be determined by one of skill in the art. The individual physician in the event of any complication can also adjust the dosage.

A therapeutically effective amount is an amount of a modulator sufficient to produce a measurable modulation of the effects of the nucleic acid ligand, including but not limited to a coagulation-modulating amount, an E2F activity-modulating amount coagulation, and/or angiogenesis factor activity (e.g., Ang1 or Ang2 activity)-modulating amount. Modulation of coagulation, E2F activity, and/or angiogenesis factor activity (e.g., Ang1 or Ang2 activity) can be measured in situ by immunohistochemistry by methods disclosed in the Examples, or by other methods known to one skilled in the art.

A preferred modulator has the ability to substantially bind to a nucleic acid ligand in solution at modulator concentrations of less than one (1.) micromolar (μM), preferably less than 0.1 μM, and more preferably less than 0.01 μM. By "substantially" is meant that at least a 50 percent reduction in target biological activity is observed by modulation in the presence of the a target, and at 50% reduction is referred to herein as an $IC_{50}$ value.

Preferred modes of administration of the materials of the present invention to a mammalian host are parenteral, intravenous, intradermal, intra-articular, intra-synovial, intrathecal, intra-arterial, intracardiac, intramuscular, subcutaneous, intraorbital, intracapsular, intraspinal, intrasternal, topical, transdermal patch, via rectal, vaginal or urethral suppository, peritoneal, percutaneous, nasal spray, surgical implant, internal surgical paint, infusion pump or via catheter. In one embodiment, the agent and carrier are administered in a slow release formulation such as an implant, bolus, microparticle, microsphere, nanoparticle or nanosphere. For standard information on pharmaceutical formulations, see Ansel, et al., *Pharmaceutical Dosage Forms and Drug Delivery Systems*, Sixth Edition, Williams & Wilkins (1995).

The modulators of the present invention can be preferably administered parenterally by injection or by gradual infusion over time. Although the tissue to be treated can typically be accessed in the body by systemic administration and therefore most often treated by intravenous administration of therapeutic compositions, other tissues and delivery techniques are provided where there is a likelihood that the tissue targeted contains the target molecule. Thus, modulators of the present invention are typically administered orally, topically to a vascular tissue, intravenously, intraperitoneally, intramuscularly, subcutaneously, intra-cavity, transdermally, and can be delivered by peristaltic techniques. As noted above, the pharmaceutical compositions can be provided to the individual by a variety of routes such orally, topically to a vascular tissue, intravenously, intraperitoneally, intramuscularly, subcutaneously, intra-cavity, transdermally, and can be delivered by peristaltic techniques. Representative, non-liming approaches for topical administration to a vascular tissue include (1) coating or impregnating a blood vessel tissue with a gel comprising a nucleic acid ligand, for delivery in vivo, e.g., by implanting the coated or impregnated vessel in place of a damaged or diseased vessel tissue segment that was removed or by-passed; (2) delivery via a catheter to a vessel in which delivery is desired; (3) pumping a nucleic acid ligand composition into a vessel that is to be implanted into a patient. Alternatively, the nucleic acid ligand can be introduced into cells by microinjection, or by liposome encapsulation. Advantageously, nucleic acid ligands of the present invention can be administered in a single daily dose, or the total daily dosage can be administered in several divided doses. Thereafter, the modulator is provided by any suitable means to alter the effect of the nucleic acid ligand by administration of the modulator.

The therapeutic compositions comprising modulator polypeptides of the present invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgment of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated.

As used herein, the terms "pharmaceutically acceptable," "physiologically tolerable," and grammatical variations, thereof, as they refer to compositions, carriers, diluents and reagents, are used interchangeably and represent that the materials are capable of administration without substantial or debilitating toxic side effects.

Pharmaceutically useful compositions comprising a modulator of the present invention can be formulated according to known methods such as by the admixture of a pharmaceutically acceptable carrier. Examples of such carriers and methods of formulation can be found in *Remington's Pharmaceutical Sciences*. To form a pharmaceutically acceptable composition suitable for effective administration, such compositions will contain an effective amount of the aptamer. Such compositions can contain admixtures of more than one modulator.

The effective amount can vary according to a variety of factors such as the individual's condition, weight, sex, age and amount of nucleic acid lidgand administered. Other factors include the mode of administration. Generally, the compositions will be administered in dosages adjusted for body weight, e.g., dosages ranging from about 1 μg/kg body weight to about 100 mg/kg body weight, preferably, 1 mg/kg body weight to 50 mg/kg body weight.

Modulators of nucleic acid ligands can be particularly useful for the treatment of diseases where it is beneficial to inhibit coagulation, E2F activity, and/or angiogenesis factor activity (e.g., Ang1 or Ang2 activity), or prevent such activity from occurring. The pharmaceutical compositions are administered in therapeutically effective amounts, that is, in amounts sufficient to generate a coagulation-, E2F activity-, and/or angiogenesis factor activity (e.g., Ang1 or Ang2 activity)-modulating response, or in prophylactically effective amounts, that is in amounts sufficient to prevent a coagulation factor from acting in a coagulation cascade, to prevent an E2F activity-mediated response, or to prevent an angiogenesis factor activity (e.g., Ang1 or Ang2 activity)-mediated response. The therapeutically effective amount and prophylactically effective amount can vary according to the type of modulator. The pharmaceutical composition can be administered in single or multiple doses.

Generally, oligonucleotide modulators of the invention can be administered using established protocols used in antisense therapies. The data presented in Example 6 indicate the activity of a therapeutic nucleic acid ligand can be modulated by the intravenous infusion of antidote oligonucleotides into a human or other animal. Furthermore, because the modulator's activity is durable, once the desired level of modulation of the nucleic acid ligand by the modulator is achieved, infusion of the modulator can be terminated, allowing residual modulator to clear the human or animal. This allows for subsequent re-treatment with the nucleic acid ligand as needed. Alternatively, and in view of the specificity of the modulators of the invention, subsequent treatment can involve the use of a second, different nucleic acid ligand/modulator (e.g., oligonucleotide) pair.

Modulators synthesized or identified according to the methods disclosed herein can be used alone at appropriate dosages defined by routine testing in order to obtain optimal modulation of nucleic acid ligand activity in coagulation, E2F, and/or angiogenesis factor cascades (e.g., Ang1 or Ang2 activity) while minimizing any potential toxicity. In addition, co-administration or sequential administration of other agents can be desirable. For combination treatment with more than one active agent, where the active agents are in separate dosage formulations, the active agents can be administered concurrently, or they each can be administered at separately staggered times.

The dosage regimen utilizing the modulators of the present invention is selected in accordance with a variety of factors including type, species, age, weight, sex and medical condition of the patient; the severity of the condition to be treated; the route of administration; the renal and hepatic function of the patient; and the particular modulator employed. A physician of ordinary skill can readily determine and prescribe the effective amount of the aptamer required to prevent, counter or arrest the progress of the condition. Optimal precision in achieving concentrations of modulator within the range that yields efficacy without toxicity requires a regimen based on the kinetics of the modulator's availability to target sites. This involves a consideration of the distribution, equilibrium, and elimination of the modulator.

In the methods of the present invention, the modulators herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrup, suppositories, gels and the like, and consistent with conventional pharmaceutical practices.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include without limitation, starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include, without limitation, sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

For liquid forms the active drug component can be combined in suitably flavored suspending or dispersing agents such as the synthetic and natural gums, for example, tragacanth, acacia, methyl-cellulose and the like. Other dispersing agents that can be employed include glycerin and the like. For parenteral administration, sterile suspensions and solutions are desired. Isotonic preparations that generally contain suitable preservatives are employed when intravenous administration is desired.

Topical preparations containing the active drug component can be admixed with a variety of carrier materials well known in the art, such as, e.g., alcohols, aloe vera gel, allantoin, glycerine, vitamin A and E oils, mineral oil, PPG2 mydstyl propionate, and the like, to form, e.g., alcoholic solutions, topical cleansers, cleansing creams, skin gels, skin lotions, and shampoos in cream or gel formulations.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of the present invention can also be coupled with soluble polymers as targetable drug carriers. Such polymers can include polyvinyl-pyrrolidone, pyran copolymer, polyhydroxypropylmethacryl-amidephenol, polyhydroxy-ethylaspartamidepbenol, or polyethyl-eneoxidepolylysine substituted with palmitoyl residues. Furthermore, the compounds of the present invention can be coupled (preferably via a covalent linkage) to a class of biodegradable polymers useful in achieving controlled release of a drug, for example, polyethylene glycol (PEG), polylacetic acid, polyepsilon caprolactone, polyhydroxy butyric acid, polyorthoesters, polyacetals, polydihydro-pyrans, polycyanoacrylates and cross-linked or amphipathic block copolymers of hydrogels. Cholesterol and similar molecules can be linked to the aptamers to increase and prolong bioavailability.

The oligonucleotide modulators can be administered directly (e.g., alone or in a liposomal formulation or complexed to a carrier (e.g., PEG)) (see for example, U.S. Pat. Nos. 6,147,204, 6,011,020).

The nucleic acid ligand or modulator can be comprised of a oligonucleotide modulator attached to a non-immunogenic, high molecular weight compound such as polyethylene glycol (PEG). In this embodiment, the pharmacokinetic properties of the complex are improved relative to the nucleic acid ligand alone. As discussed supra, the association could be through covalent bonds or non-covalent interactions. In one embodiment, the modulator is associated with the PEG molecule through covalent bonds. Also, as discussed supra, where covalent attachment is employed, PEG may be covalently bound to a variety of positions on the oligonucleotide modulator. In the preferred embodiment, an oligonucleotide modulator is bonded to the 5' thiol through a maleimide or vinyl sulfone functionality. In one embodiment, a plurality of modulators can be associated with a single PEG molecule. The modulator can be to the same or different target. In embodiments where there are multiple modulators to the same nucleic acid ligand, there is an increase in avidity due to multiple binding interactions with the ligand. In yet a further embodiment, a plurality of PEG molecules can be attached to each other. In this embodiment, one or more modulators to the same target or different targets can be associated with each PEG molecule. This also results in an increase in avidity of each modulator to its target. In embodiments where multiple modulators specific for the same target are attached to PEG, there is the possibility of bringing the same targets in close proximity to each other in order to generate specific interactions between the same targets. Where multiple modulators specific for different targets are attached to PEG, there is the possibility of bringing the distinct targets in close proximity to each other in order to generate specific interactions between the targets. In addition, in embodiments where there are modulators to the same target or different targets associated with PEG, a drug can also be associated with PEG. Thus the domplex would provide targeted delivery of the drug, with PEG serving as a Linker.

One problem encountered in the therapeutic and in vivo diagnostic use of nucleic acids is that oligonucleotides in their phosphodiester form may be quickly degraded in body fluids by intracellular and extracellular enzymes such as endonucleases and exonucleases before the desired effect is manifest. Certain chemical modifications of the nucleic acid can be made to increase the in vivo stability of the nucleic acid or to enhance or to mediate the delivery of the nucleic acid. Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid bases or to the nucleic acid as a whole. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil; backbone modifications, phosphorothioate or alkyl phosphate modifications, methylations, unusual base-pairing combinations such as the isobases isocytidine and isoguanidine and the like. Modifications can also include 3' and 5' modifications such as capping.

Lipophilic compounds and non-immunogenic high molecular weight compounds with which the modulators of the invention can be formulated for use in the present invention and can be prepared by any of the various techniques presently known in the art or subsequently developed. Typically, they are prepared from a phospholipid, for example, distearoyl phosphatidylcholine, and may include other materials such as neutral lipids, for example, cholesterol, and also surface modifiers such as positively charged (e.g., sterylamine or aminomannose or aminomannitol derivatives of cholesterol) or negatively charged (e.g., diacetyl phosphate, phosphatidyl glycerol) compounds. Multilamellar liposomes can be formed by the conventional technique, that is, by depositing a selected lipid on the inside wall of a suitable container or vessel by dissolving the lipid in an appropriate solvent, and then evaporating the solvent to leave a thin film on the inside of the vessel or by spray drying. An aqueous phase is then added to the vessel with a swirling or vortexing motion which results in the formation of MLVs. UVs can then be formed by homogenization, sonication or extrusion (through filters) of MLV's. In addition, UVs can be formed by detergent removal techniques. In certain embodiments of this invention, the complex comprises a liposome with a targeting nucleic acid ligand(s) associated with the surface of the liposome and an encapsulated therapeutic or diagnostic agent. Preformed liposomes can be modified to associate with the nucleic acid ligands. For example, a cationic liposome associates through electrostatic interactions with the nucleic acid. Alternatively, a nucleic acid attached to a lipophilic compound, such as cholesterol, can be added to preformed liposomes whereby the cholesterol becomes associated with the liposomal membrane. Alternatively, the nucleic acid can be associated with the liposome during the formulation of the liposome. Preferably, the nucleic acid is associated with the liposome by loading into preformed liposomes.

Alternatively, oligonucleotide modulators of the invention can be produced in vivo following administration of a construct comprising a sequence encoding the oligonucleotide. Techniques available for effecting intracellular delivery of RNA modulators of gene expression can be used (see generally Sullenger et al, Mol. Cell Biol. 10:6512 (1990)).

Certain aspects of the invention can be described in greater detail in the non-limiting Examples that follow.

EXAMPLE 1

Aptamer to Factor IXa

Nuclease-resistant 2'-fluoro pyrimidine-modified aptamers to human coagulation Factor IXa were generated as described in WO 0226932 A2. Eight iterative cycles of selection were performed, yielding a family of 16 aptamers with high affinity for FIXa; $K_D$'s ranging from ~0.6-15 nM in physiologic salt and pH at 37° C. Comparative sequence analysis made it possible to predict and synthesize the minimized version of the highest affinity aptamer, termed RNA 9.3t ("t" for truncate), shown in FIG. 1. This 34 nucleotide aptamer has a molecular weight of 11.5 kDa and binds FIXa with essentially the same affinity as the full-length sequence ($K_D$ 0.6 nM). As a control, a mutant version of RNA 9.3t termed 9.3tM was synthesized in which the absolutely conserved A's in the internal loop were mutated to G's (FIG. 1). This aptamer binds FIXa with a $K_D$>5 µM as determined by competition binding assays. In all activity assays, RNA 9.3tM is employed as a control to measure any non-specific effects caused by an aptamer of this composition. Aptamer 9.3t blocks FX activation by FVIIIa/FIXa/lipids, and also partially blocks synthetic substrate hydrolysis by FIXa.

To examine the specificity of the aptamer for FIXa versus structurally similar coagulation factors, the affinity of 9.3t for FIX, FVIIa, FXa, FXIa and APC was measured in direct binding assays as previously described (Rusconi et al., Thrombosis and Haemostasis 83:841-848 (2000)). The aptamer binds FIX only ~5-50 fold less tightly than FIXa. It failed to exhibit significant binding at protein concentrations up to 5 µM (fraction RNA bound<10%) to any of the other proteins tested. Therefore, the specificity of aptamer 9.3t for FIXa versus FVIIa, FXa, FXIa or APC is >5000 fold.

Figure 2:
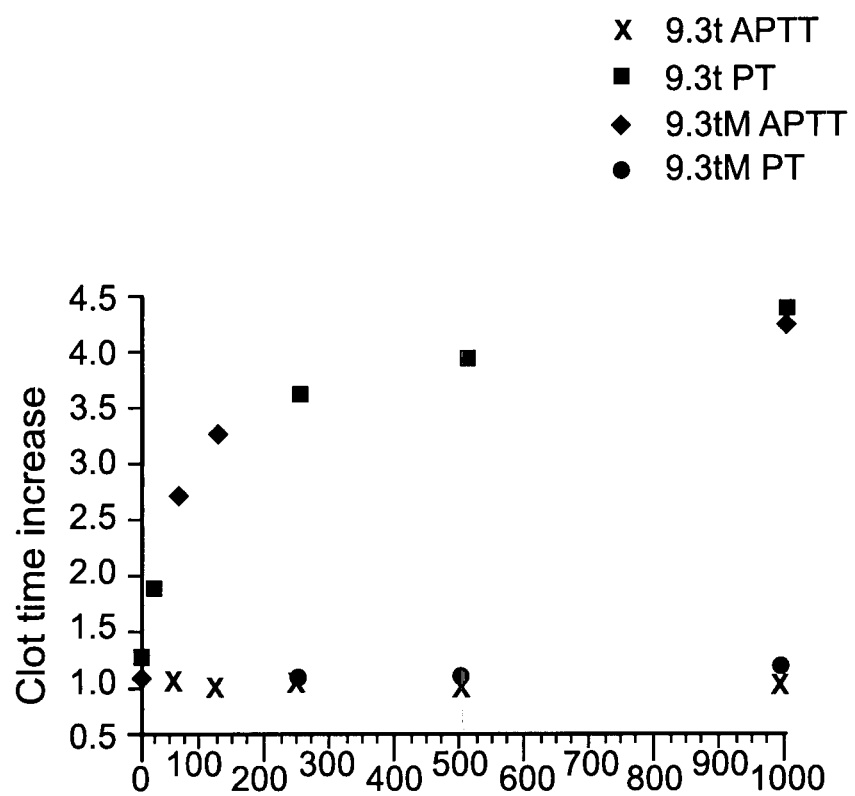
FIG. 2 shows the anticoagulant activity of aptamer 9.3t. Clot time increase is normalized to baseline clot time in the absence of aptamer.

To determine the anticoagulant potency of RNA 9.3t, the ability of 9.3t to prolong the clotting time of human plasma has been evaluated in activated partial thromboplastin time (APTT) and prothrombin time (PT) clotting assays. Aptamer 9.3t, but not control aptamer 9.3tM, was able to prolong the clotting time of human plasma in a dose dependent manner (FIG. 2). Neither aptamer had an effect on the PT, demonstrating the functional specificity of aptamer 9.3t for FIXa and demonstrating that this type of oligonucleotide, at concentrations up to 1 µM, does not non-specifically increase the clotting time of human plasma. Thus, RNA 9.3 is a potent anticoagulant, with a maximal effect on the APTT similar to that observed in FIX deficient plasma. Similar experiments have been performed in porcine plasma, and similar potency and specificity have been observed.

Figure 3:
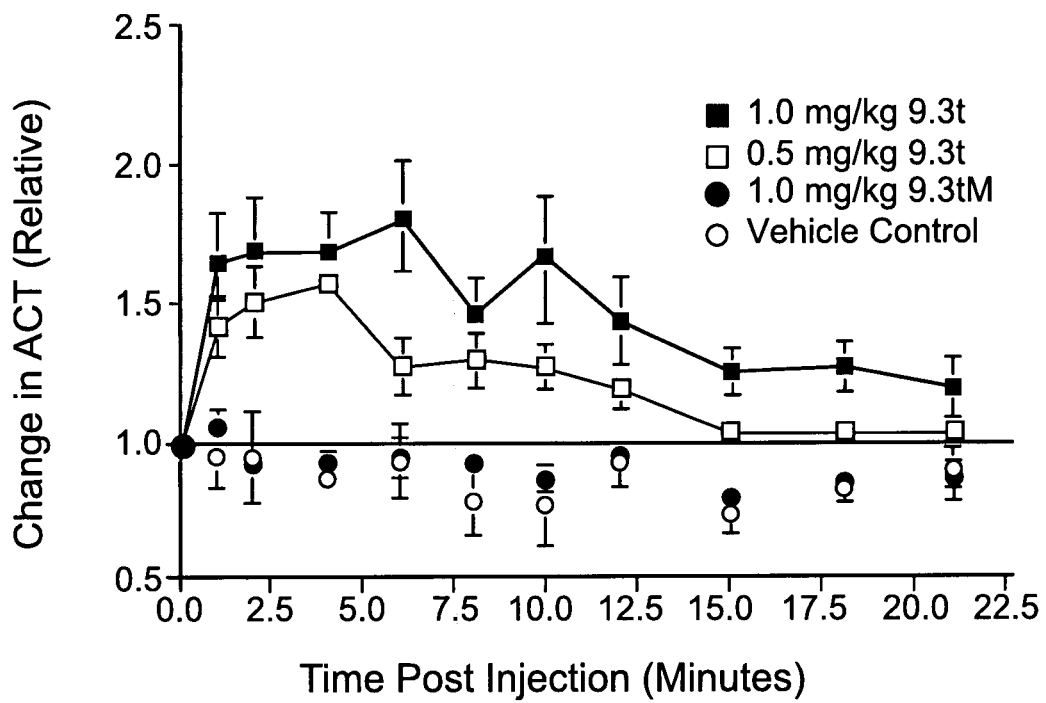
FIG. 3 shows ACT change of pigs following aptamer injection. Data are normalized to pre-injection baseline.
Figure 4:
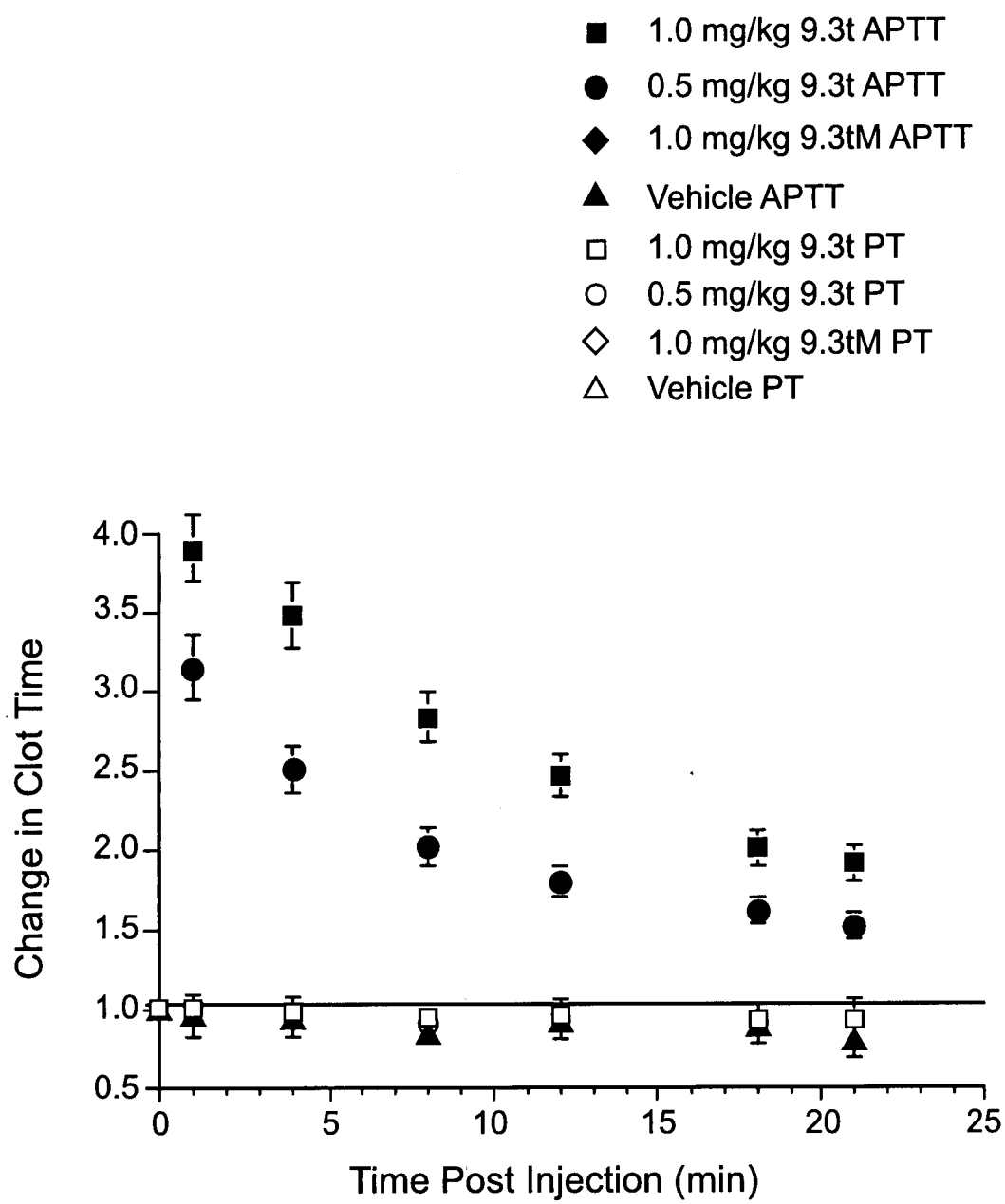
FIG. 4 shows the clot time change of pigs following aptamer injection.

To determine if this molecule is capable of inhibiting FIX/FIXa activity in vivo, the ability of this aptamer to systemically anticoagulate small (1.5-4 kg) pigs following bolus intravenous injection was tested. For these experiments, an intravenous catheter was placed in the femoral vein for sample injection and an arterial catheter was placed in a femoral artery of the animal for serial withdrawal of blood samples. A pre-injection blood sample was taken, and the ACT time measured on site to establish a baseline whole blood clot time for the animal. Aptamer 9.3t at doses of 0.5 mg/kg (n=4) and 1.0 mg/kg (n=4), aptamer 9.3tM at 1.0 mg/kg (n=3) or vehicle (n=3) was then delivered by intravenous bolus injection. Blood samples were taken at various times post injection, and the ACT immediately determined. Additional blood was drawn for determination of APTT's at different times post-injection. As shown in FIG. 3, aptamer 9.3t, but not the control aptamer 9.3tM or vehicle, was able to inhibit FIXa activity in vivo as evidenced by a significant dose-dependent increase in the animal's ACT post injection. As shown in FIG. 4, aptamer 9.3 specifically prolonged the APTT, but not PT of the animals in a dose dependent manner. Using the in vitro dose response curves from the APTT experiments, the change in 9.3t plasma concentration over time following injection can be estimated.

Figure 5A:
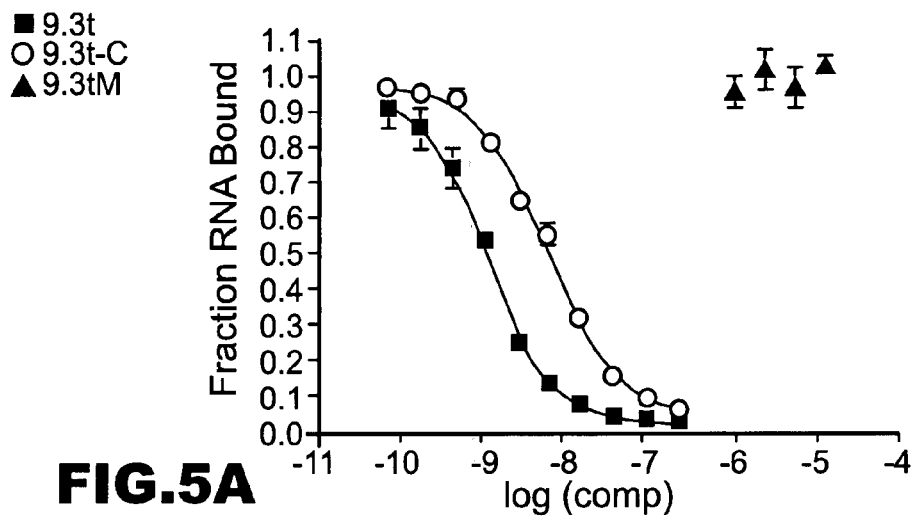
FIGS. 5A-5C show the in vitro inhibitory activity of cholesterol-modified aptamer, 9.3t-C.
Figure 5B:
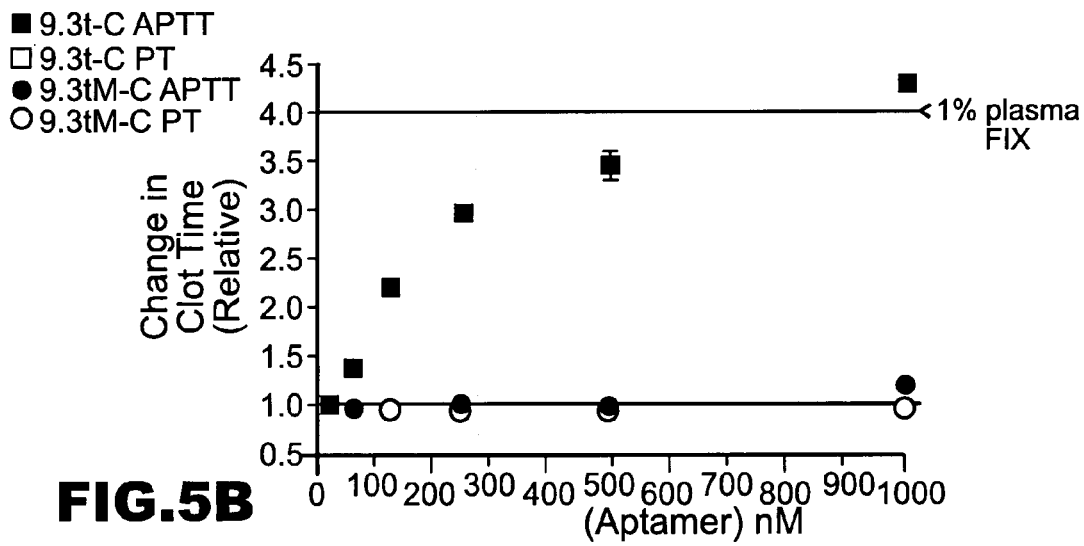
Figure 5C:
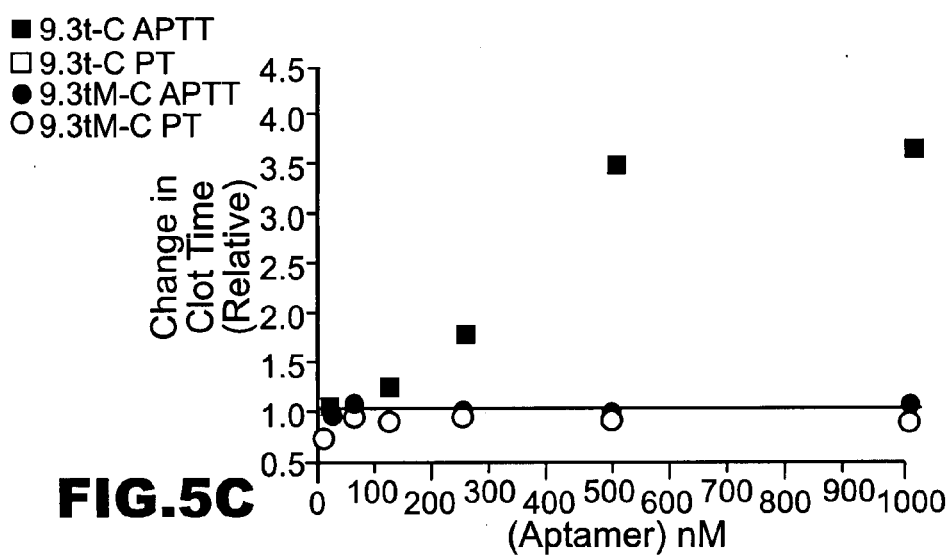
Figure 6A:
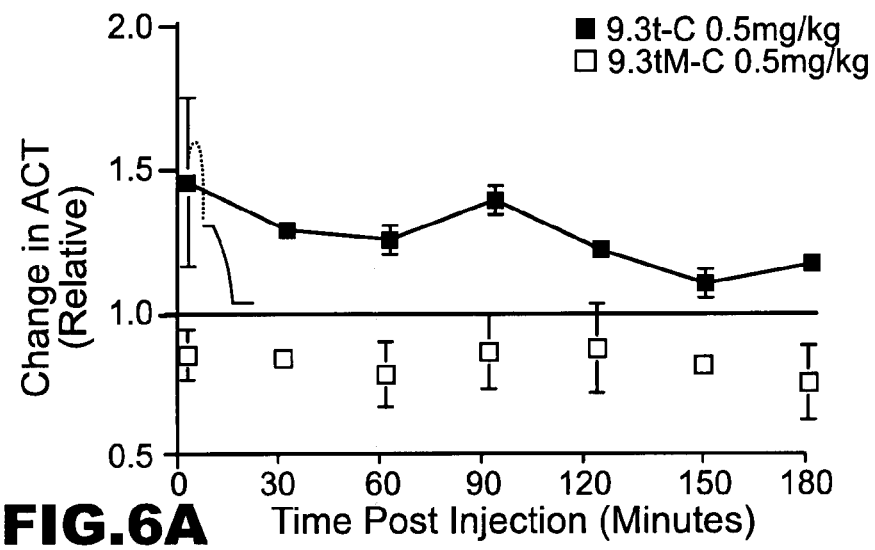
FIGS. 6A-6C show the in vivo anticoagulant activity of aptamer 9.3t-C.
Figure 6B:
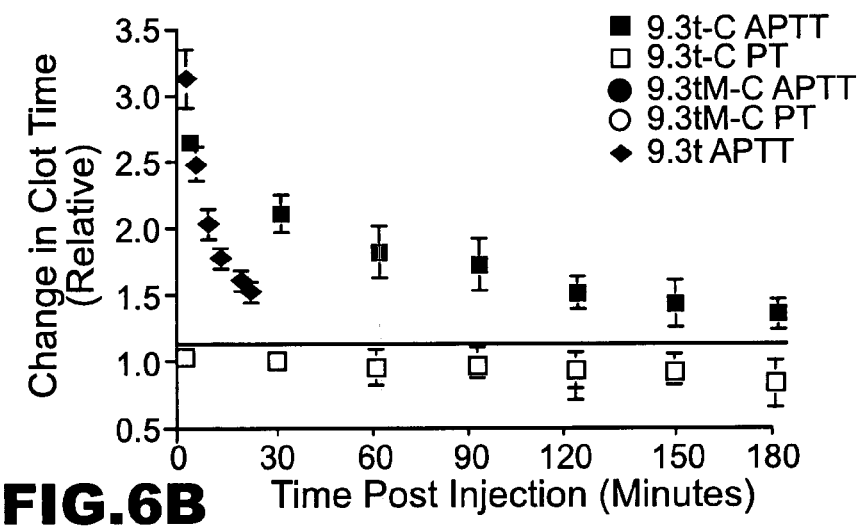
Figure 6C:
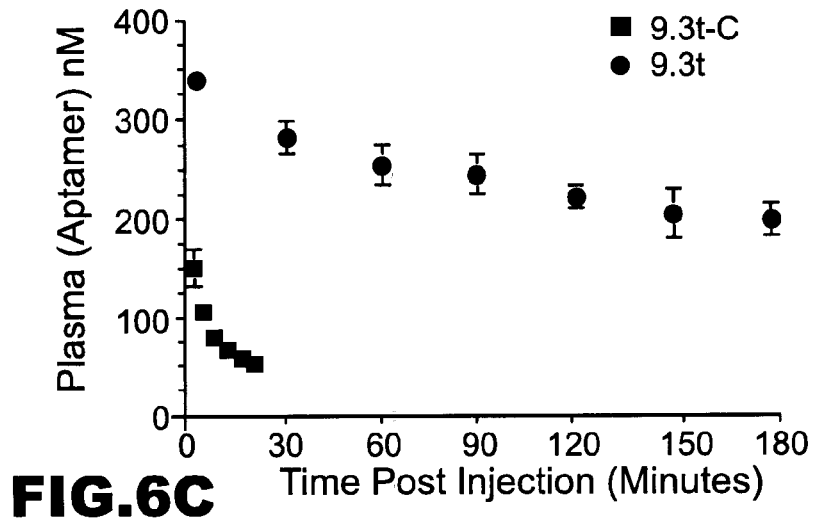

As an attempt to increase the bioavailability of 9.3t, a version of this aptamer with a 5'cholesterol moiety was synthesized, termed 9.3t-C. The cholesterol modified aptamer retained high affinity binding to FIXa (FIG. 5A) and potent anticoagulant activity (FIGS. 5B and 5C). The in vivo effects of this modification on the circulating half-life of 9.3t-C versus 9.3t (n=2 animal for each aptamer) have been tested using the pig systemic anticoagulation model. Following injection of 0.5 mg/kg 9.3t-C, the ACT of the animal increased ~1.4 fold and was sustained at this level for 1 hour post injection (FIG. 6A). FIG. 6B shows analysis of the APTT and PT of the animals from this experiment. While the anticoagulant potency of the two aptamers is similar, the duration of the anticoagulant effect of 9.3t-C is significantly longer (FIG. 6C).

EXAMPLE 2

Oligonucleotide that Reverses Interaction of the FIXa Aptamer with Coagulation FIXa The secondary structure model of 9.3t is shown in FIG. 1 and was developed from comparative sequence analysis of the related FIXa aptamer sequences shown in FIG. 7. These data strongly support formation of the stem-looped structure depicted in FIG. 1. In addition, mutational analysis of aptamer 9.3t demonstrated that disruption of either stem 1 or stem 2 resulted in a greater than 1000 fold loss of affinity for FIXa. Therefore, a 17 residue all 2'Omethyl oligonucleotide was designed (sequence 5'auggggaggcagcauua3') (SEQ ID NO: 25) (Anti-D1) complementary to the 3'half of aptamer 9.3t beginning at the 5' end of loop 2 (L2 in FIG. 7) and extending to the 3' end of the aptamer. This design allows for nucleation of an intermolecular duplex between the oligonucleotide and loop 2 of the aptamer. Also, formation of the intermolecular duplex is thermodynamically favored due to both the length and base composition of the complimentary oligonucleotide. A ribonucleotide duplex of this sequence has calculated free energy of −26.03 kcal/mol and a predicted $T_m$ of 75.4° C. The half-life of such a duplex at 37° C. would greatly exceed 24 hours.

To determine if this oligonucleotide could denature aptamer 9.3t, radiolabeled aptamer 9.3t (125 nM) was incubated with increasing concentrations of the "antidote" oligonucleotide (from equimolar to an 8 fold molar excess) at 37° C. for 15 minutes (-heat FIG. 8), and the amount of intermolecular duplex formed was visualized by native gel electrophoresis (12% acrylamide, 150 mM NaCl, 2 mM $CaCl_2$, run in 1Xtris-borate buffer +2 mM $CaCl_2$) followed by phosphorimaging (FIG. 8). To generate an oligonucleotide-aptamer complex as a gel-mobility control, the oligonucleotide was annealed to aptamer 9.3t by heating the aptamer and an 8 fold molar excess of the oligonucleotide at 95° C. for 5 minutes prior to the 37° C. incubation (+heat FIG. 8). The same set of experiments was performed with a nonsense oligonucleotide of the same base composition as the antidote oligonucleotide (N.S. in FIG. 8). As can be seen in FIG. 8, the antidote oligonucleotide readily denatures aptamer 9.3t as evidenced by near complete formation of the oligonucleotide-aptamer complex when the oligonucleotide was present at an 8 fold molar excess to the aptamer. In addition, this interaction is very specific, as no complex is observed, with or without heating, between the aptamer and the nonsense control oligonucleotide.

Figure 9A:
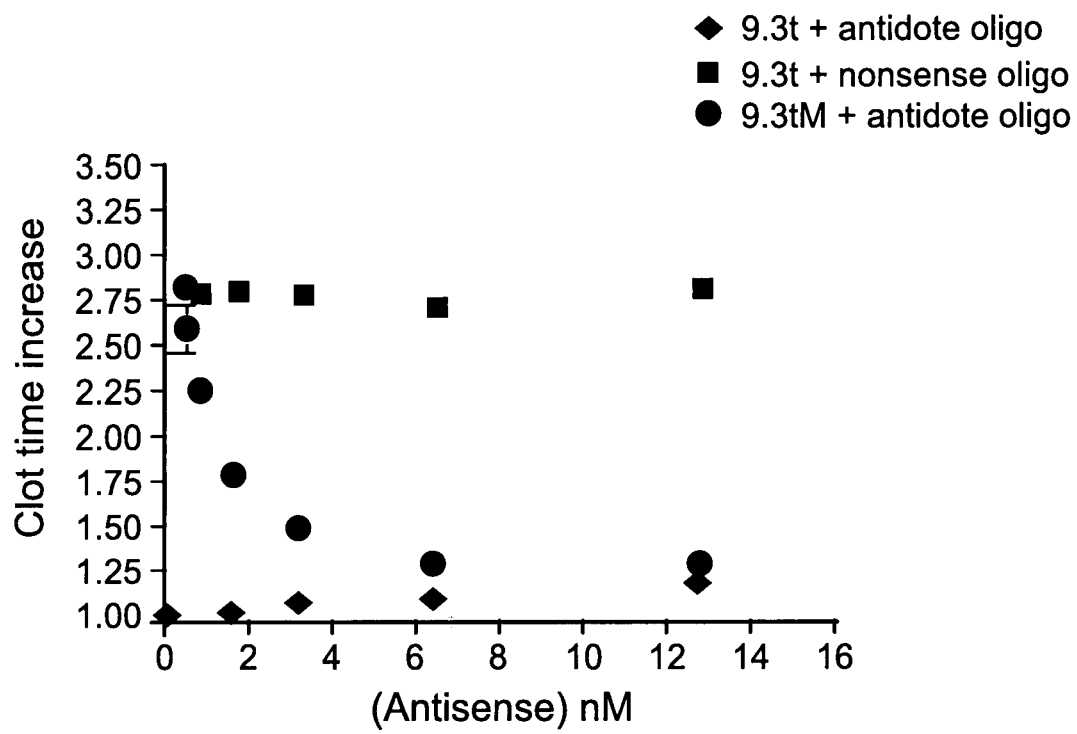
FIGS. 9A and 9B show antidote oligonucleotide reversal of anticoagulant activity of aptamer 9.3t in human plasma.
Figure 9B:
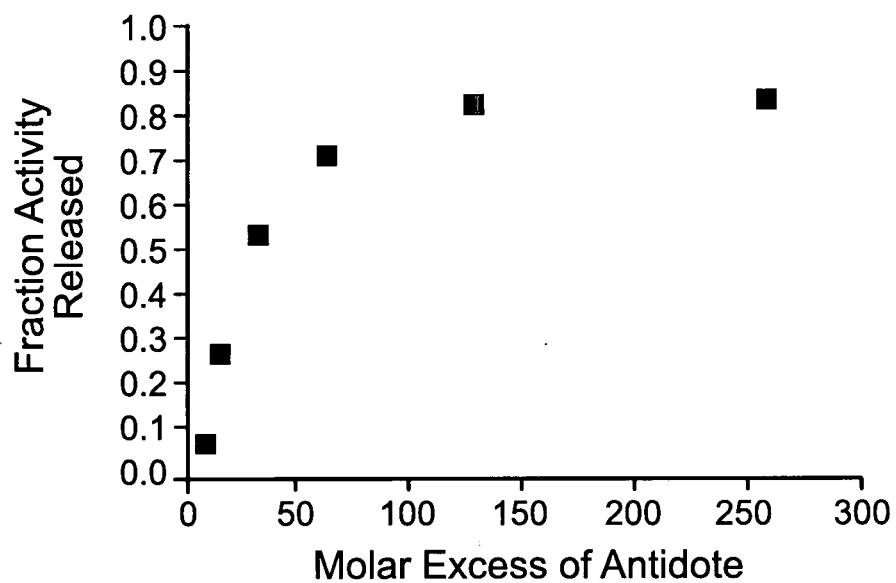

To determine if this antidote oligonucleotide could reverse the anticoagulant activity of aptamer 9.3t, the APTT of pooled human plasma was measured in the presence of 50 nM 9.3t and increasing concentrations of the antidote oligonucleotide (FIGS. 9A and 9B). In this experiment, aptamer 9.3t was pre-incubated 5 minutes in plasma prior to addition of the antidote oligonucleotide to generate aptamer-FIX complexes, the antidote or nonsense oligonucleotide were then added, and the incubation continued for an additional 10 minutes prior to adding $CaCl_2$ to initiate clot formation. As shown in FIGS. 9A and 9B, the antidote oligonucleotide is able to effectively reverse about 80% of the anticoagulant activity of aptamer 9.3t. However, the molar excess of antidote oligonucleotide required to achieve this effect is substantially larger than the amount required to effectively denature the aptamer in the absence of protein.

EXAMPLE 3

Specificity of Oligonucleotide Antidotes

In order to assess the specificity of an oligonucleotide antidote, aptamer 9.20t was prepared (see FIG. 10A). Stem 1 of 9.20t is identical to stem 1 of aptamer 9.3t, as is the 3' half of stem 2. The main differences between 9.20t and 9.3t are found in loop 2 and loop 3 (compare FIG. 1 with FIG. 10A).

Aptamer 9.20t binds FIXa with a $K_D$ comparable to that of 9.3t. APTT assays were used to measure the clot time of human plasma as a function of the concentration of aptamer 9.20t. Its in vitro anticoagulant potency in human plasma was comparable to that of 9.3t (FIG. 10B). Aptamer 9.20t was added to human plasma at a concentration of 50 nM and allowed to bind to plasma FIX for 5 minutes. Varying concentrations of antidote oligonucleotide Anti D1 were then added, and the APTT was measured at 10 minutes after antidote addition to plasma. The relative change in clot time caused by 9.20t addition to plasma was unaffected by the addition of this antidote oligonucleotide complimentary to aptamer 9.3t (FIG. 10C).

EXAMPLE 4

Tailed Aptamer 9.3t

Figure 11:
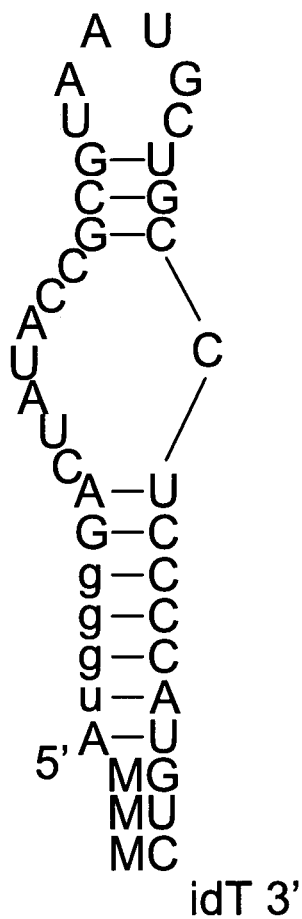
FIG. 11 shows the secondary structure of tailed aptamer 9.3t-3NT (SEQ ID NO: 19). Also shown are antidote oligonucleotides (SEQ ID NO:20-SEQ ID NO:22).

In order to determine if a single-stranded "tail" added to the end of an aptamer promotes association of an "antidote" oligonucleotide with the aptamer, a 3' tail was added to aptamer 9.3t, the tailed aptamer being designated 9.3t-3NT (FIG. 11). The 3' tail of 9.3t-3NT is a 3 nucleotide 2'Omethyl modified RNA tail. This tail sequence was chosen to reduce the likelihood of impacting the activity of the aptamer, and to reduce potential secondary structures within the complimentary antidote oligonucleotide.

Figure 12A:
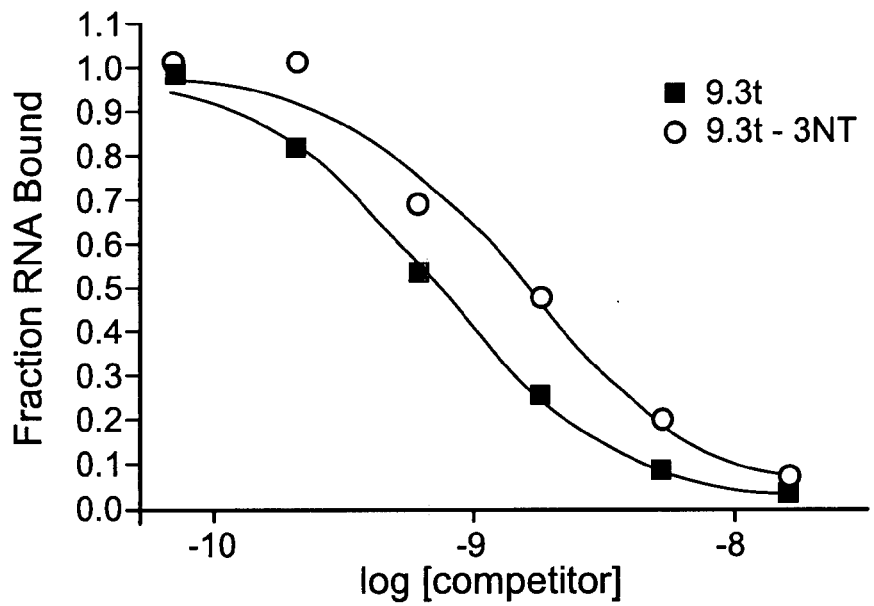
FIGS. 12A and 12B show the activity of aptamer 9.3t-3NT.
Figure 12B:
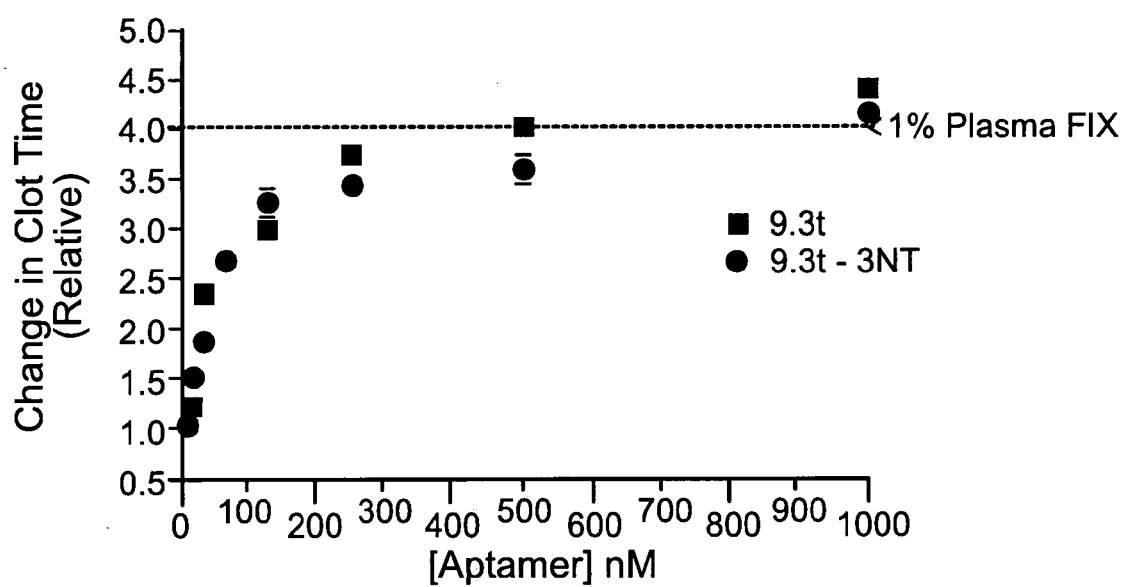

The affinity of aptamer 9.3t-3NT was compared to 9.3t in competition binding assays (FIG. 12A). The affinity of aptamer 9.3t-3NT for FIXa was comparable to that of 9.3t ($K_D$ 1.5 nM or less). APTT assays were used to measure the clot time of human plasma as a function of the concentration of aptamers 9.3t-3NT and 9.3t (FIG. 12B). The anticoagulant activities of the aptamers were similar, and both aptamers were able to completely inhibit FIX activity in human plasma.

Figure 13A:
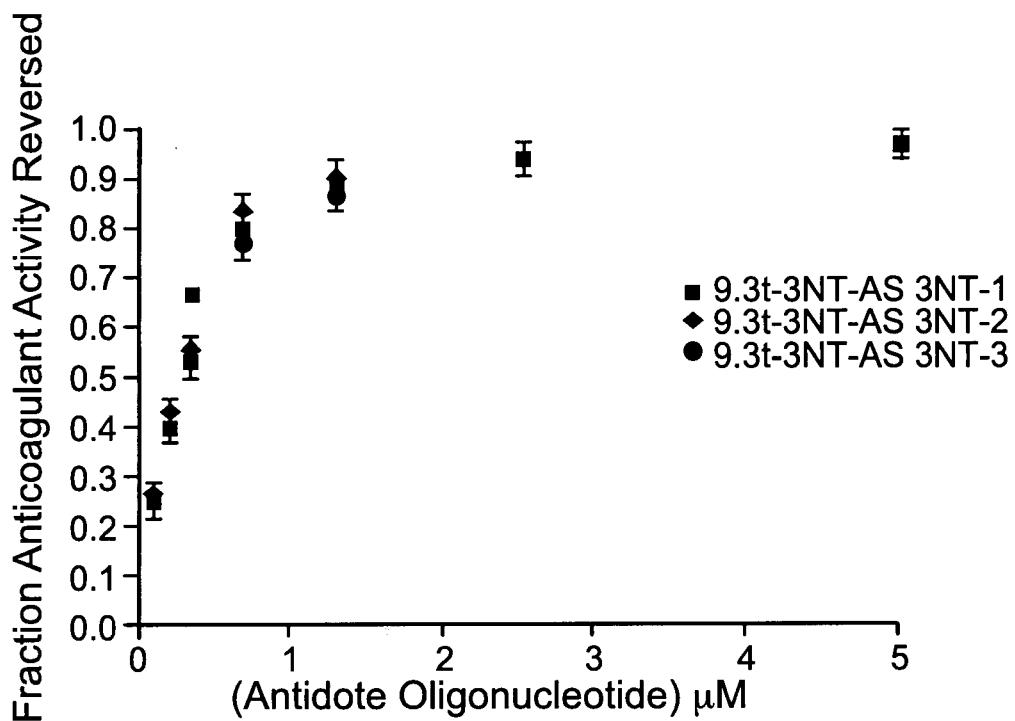
FIGS. 13A and 13B show the in vitro reversal of the anticoagulant activity of aptamer 9.3t-3NT.
Figure 13B:
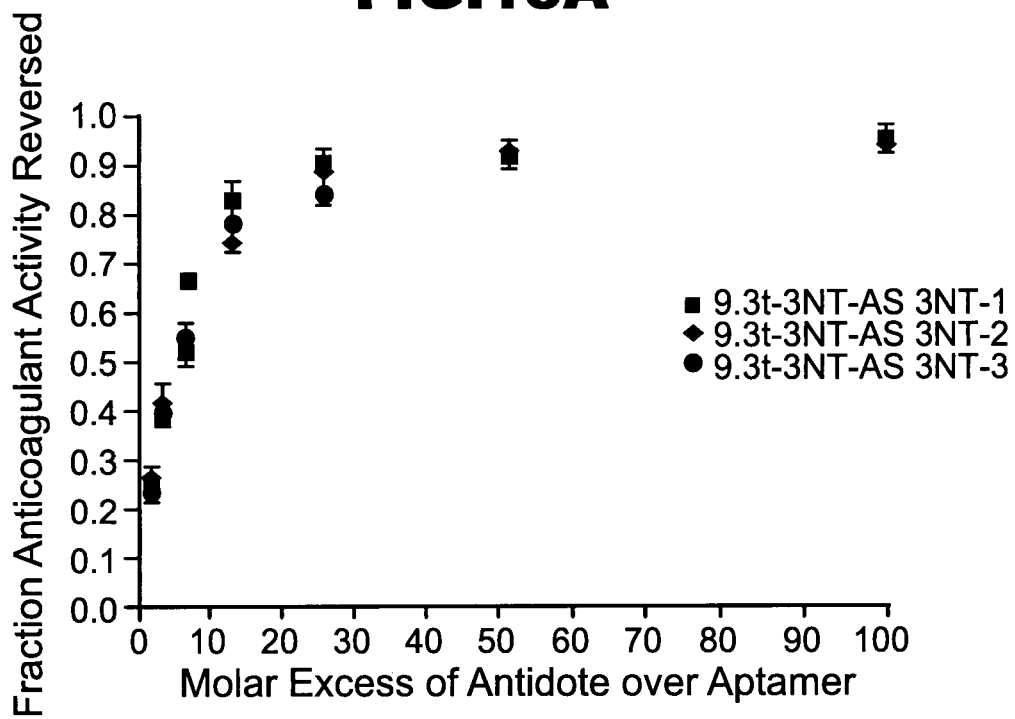

Aptamer 9.3t-3NT was added to human plasma at a concentration of 50 nM (~3 fold increase in APTT) and allowed to bind to plasma FIX for 5 minutes. Varying concentrations of antidote oligonucleotides (see FIG. 11) were then added, and the APTT was measured at 10 minutes after antidote addition to plasma (FIG. 13A). The fraction of the anticoagulant activity reversed by the antidote oligonucleotide is the difference between the APTT in the presence of aptamer alone and the APTT in the presence of aptamer +antidote divided by the change in APTT over baseline in the presence of the aptamer alone (0=no effect, 1=complete reversal). Each of the complimentary antidote oligonucleotides tested was able to reverse>90% of the anticoagulant activity of aptamer 9.3t-3NT within 10 minutes of addition in human plasma, with AS3NT-3 demonstrating the most potent reversal activity (FIG. 13B). This reversal activity is comparable to the ability of protamine to reverse the APTT increase following heparin addition to human plasma.

Figure 14A:
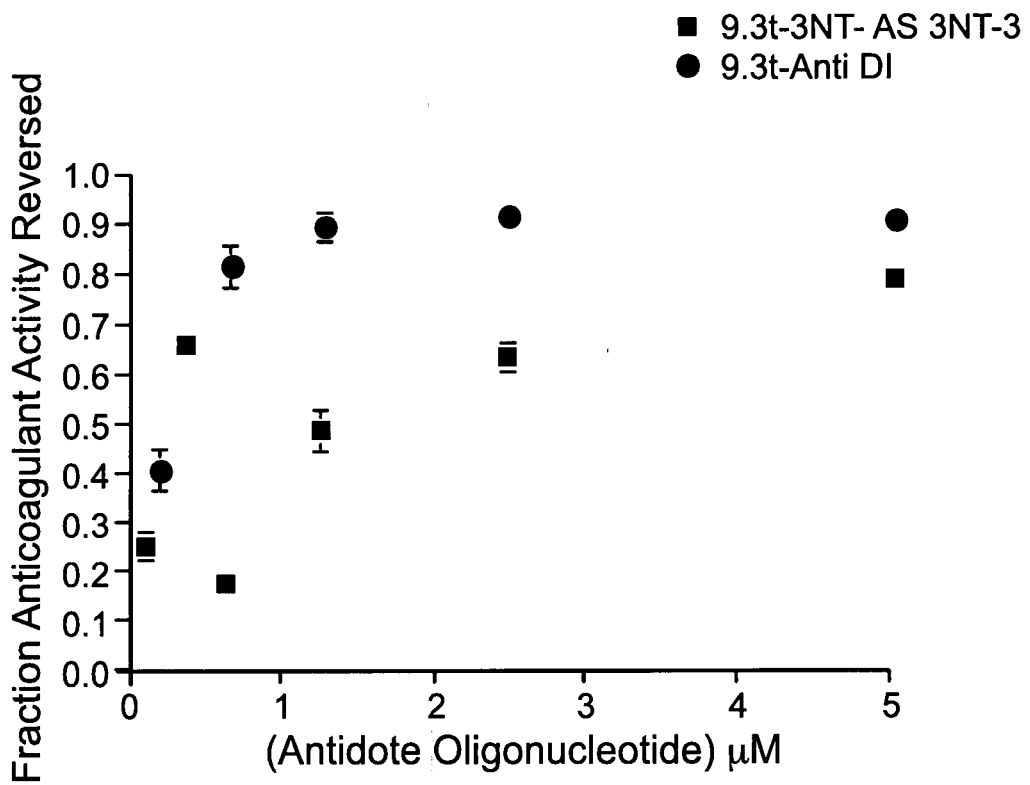
FIGS. 14A and 14B show the impact of tail addition to FIXa aptamer 9.3t on the ability to reverse anticoagulant activity.
Figure 14B:
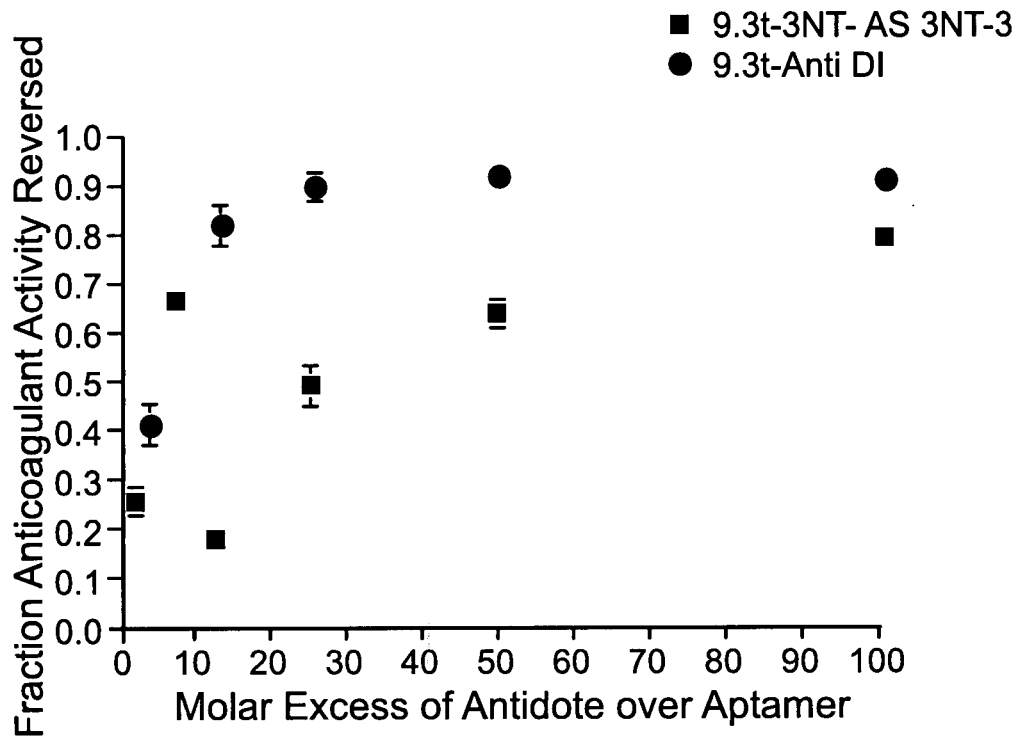

The reversal of the anticoagulant activity of 9.3t-3NT by antidote oligonucleotide AS3NT-3 was compared to the reversal of the anticoagulant activity of 9.3t by antidote oligonucleotide Anti D1. The addition of the tail to the aptamer increases the efficiency of reversal by an antidote oligonucleotide with sequences complimentary to the 3' tail of the aptamer (FIGS. 14A and 14B).

In addition to the foregoing, the following oligonucleotide modulators have been produced that target aptamer 9.3t, and are effective at reversing its anticoagulant activity in human plasma in vitro (all are 2'Omethyl oligonucleotides):
Anti D T1: 5' cau ggg gag gca gca uua 3' (SEQ ID NO: 26)
AS 9.3t-2: 5' cau ggg gag gca gca 3' (SEQ ID NO: 27)
AS 9.3t-3: 5' cau ggg gag gca 3' (SEQ ID NO: 28).

The following oligonucleotide modulators target aptamers 9.3t and 9.3t-3NT, and are effective at reversing its anticoagulant activity in human plasma in vitro (all are 2'Omethyl oligonucleotides):
AS 5-1: 5' gca uua cgc ggu aua guc ccc ua 3' (SEQ ID NO: 29)
AS 5-2: 5' cgc ggu aua guc ccc ua 3' (SEQ ID NO: 30)

The following oligonucleotide modulators target either aptamer 9.3t or aptamer 9.3t-3NT, and are mutant oligonucleotides designed to test specific aspects of the design of modulating oligonucleotides to these aptamers (all are 2'Omethyl oligonucleotides):
AS 9.3t-M: 5' cau ggg gaa gca 3' (SEQ ID NO:37)
AS 9.3t-3NOH: 5' aug ggg agg ca 3' (SEQ ID NO:38).
AS 3NT-3M: 5' gac aug ggg aag ca 3' (SEQ ID NO:39)
AS 3NT-3 MT: 5' aca aug ggg agg ca 3' (SEQ ID NO:40)

EXAMPLE 5

Antidote Oligonucleotide to Aptamer 9.3t

The antidote oligonucleotide 5-2C (5' CGC GGU AUA GUC CCC AU) (SEQ ID NO: 41) but not a scrambled version of this antidote oligonucleotide, 5-2C scr, has been shown to effectively reverse the activity of aptamers 9.3t and Peg-9.3t in vitro in human plasma. Peg-9.3t is 9.3t with a 40 KDa polyethylene glycol appended to its 5' end via a linker.

Figure 15:
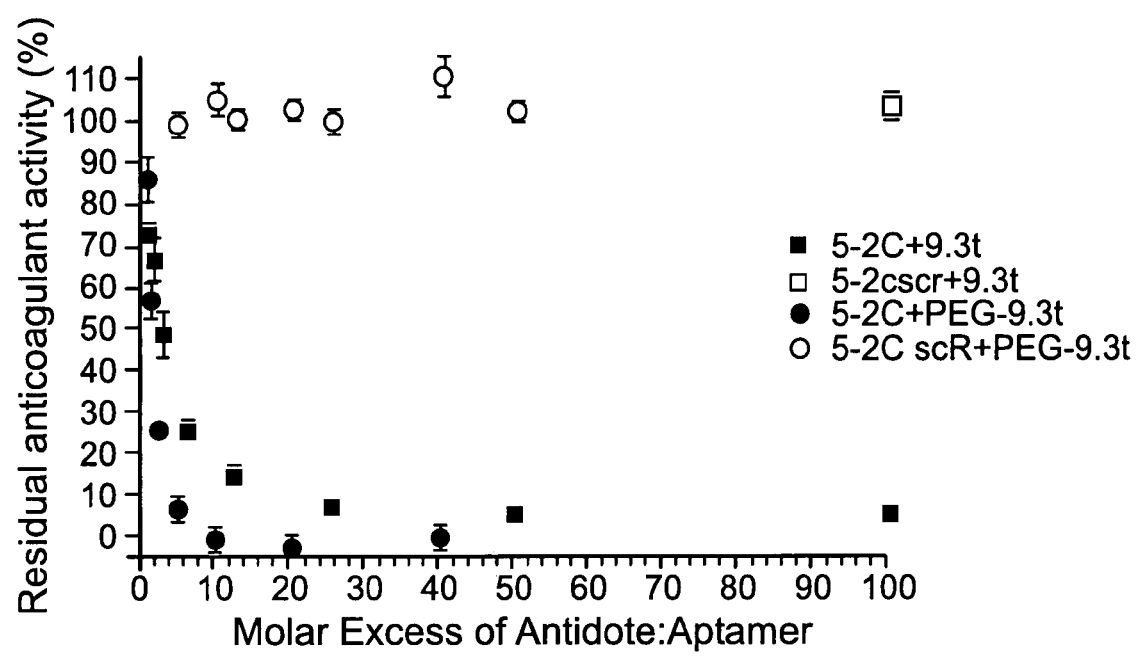
FIG. 15. The antidote oligonucleotide 5-2C but not a scrambled version of this antidote oligonucleotide, 5-2C scr, effectively reverses the activity of aptamers 9.3t and Peg-9.3t in human plasma.

In these experiments, aptamer was added to plasma (50 nM 9.3t, 125 nM Peg-9.3t) and allowed to incubate for 5 minutes. Antidote oligonucleotides were then added, and APTT assays were initiated 10 minutes after antidote addition. The results are shown in FIG. 15.

EXAMPLE 6

Rapidity and Durability of Control of Aptamer 9.3t by Antidote Oligonucleotide

Aptamers 9.3t or Peg-9.3t were added to human plasma in vitro at a final concentration of 50 nM for 9.3t or 125 nM for Peg-9.3t, and allowed to incubate for 5 minutes at 37° C. Antidote oligonucleotide 5-2C at the indicated molar excess to the aptamer was then added, and the residual aptamer activity was determined by measuring the clotting time in APTT assays at the times indicated following antidote addition. The % residual anticoagulant activity equals 1—the ratio of $(T_{Aptamer}alone-T_{Aptamer}+antidote)$ to $(T_{Aptamer}alone-T_{baseline})\times 100$, where T=APTT clot time.

The duration of the inactivation of the anticoagulant activity of Peg-9.3t by antidote oligonucleotide 5-2C was measured in vitro in human plasma. Briefly, Peg-9.3t was added to human plasma to a final concentration of 125 nM and allowed to incubate for 5 minutes. Antidote oligonucleotide 5-2C was then added at a 10 fold molar excess, or in a parallel experiment buffer alone was added in place of the antidote oligonucleotide, and the clotting time was measure in an APTT assays at various time points following antidote addition. The % residual anticoagulant activity was determined as above. The APTT of untreated human plasma was also measured in parallel to establish a baseline clotting time at each time point. It was found that after 5 hours of incubation at 37° C., the APTT of the untreated plasma began to increase, indicating the loss of the clot forming activity of the plasma, and the experiment was thus stopped at 5 hours.

Figure 16:
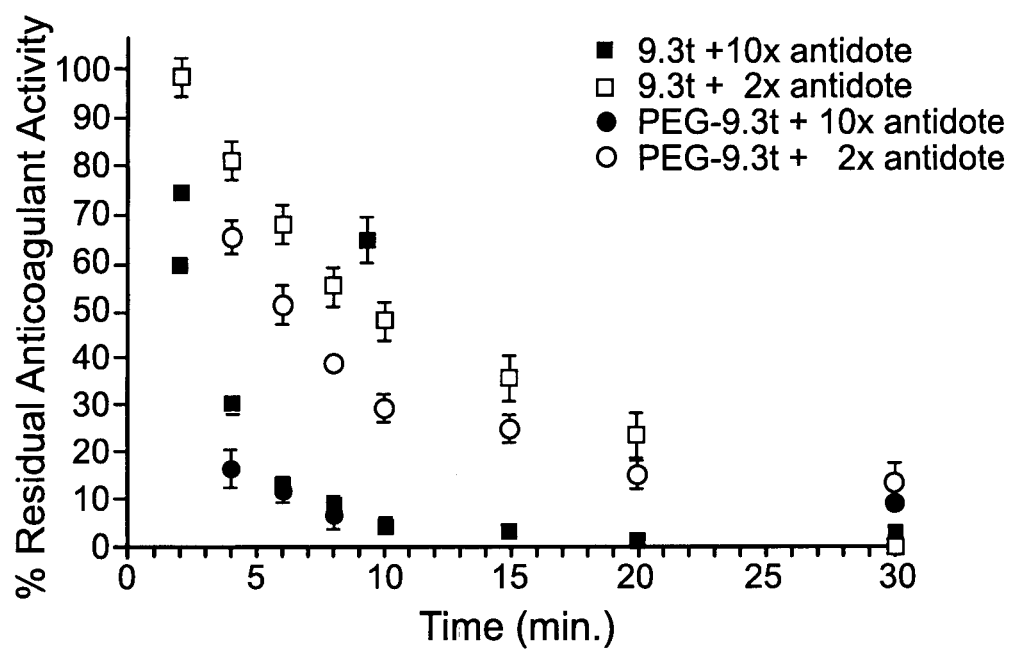
FIG. 16. Kinetics of antidote activity in human plasma, as described in Example 6.
Figure 17:
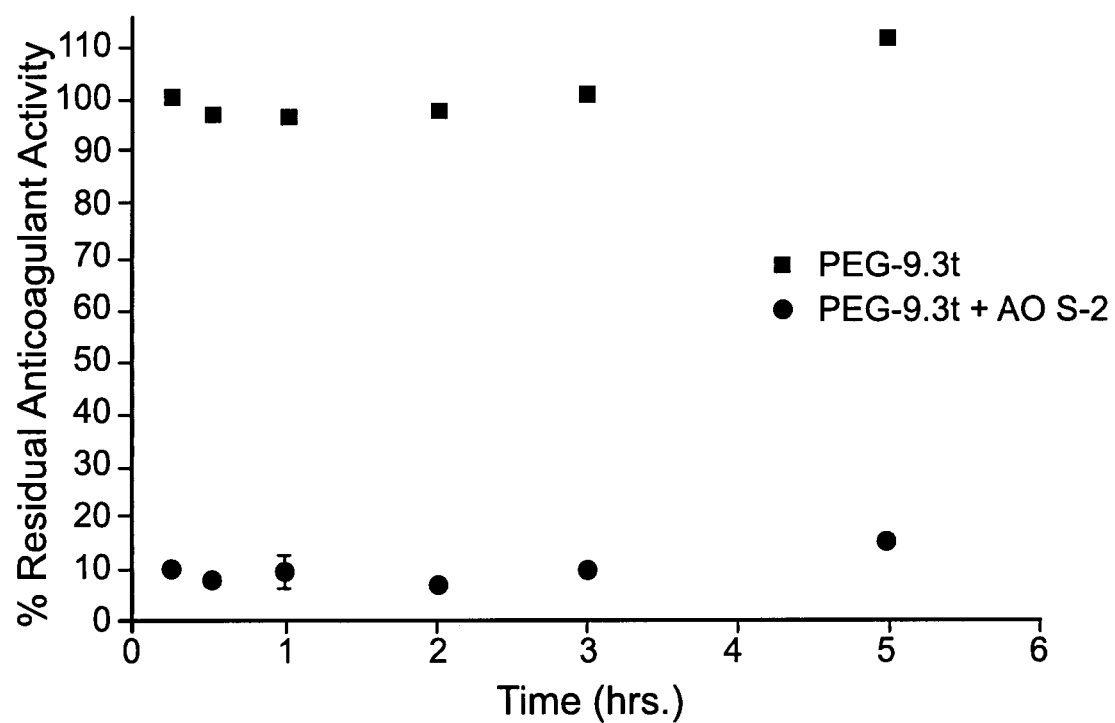
FIG. 17. Duration of antidote activity in vitro, as described in Example 6.

The data presented in FIGS. 16 and 17 demonstrate to the ability to rapidly and durably control the anticoagulant activity of the FIXa antagonist aptamer 9.3t, and its derivatives, using antidote oligonucleotides. Together these data demonstrate that the onset of action of the antidote is rapid, that the time needed for the antidote to act is at least in part dependent on the antidote concentration, and that once the antidote has inactivated the aptamer, this effect is durable.

EXAMPLE 7

Antidote Oligonucleotide to Aptamer Against Coagulation Factor Xa

Figure 18A:
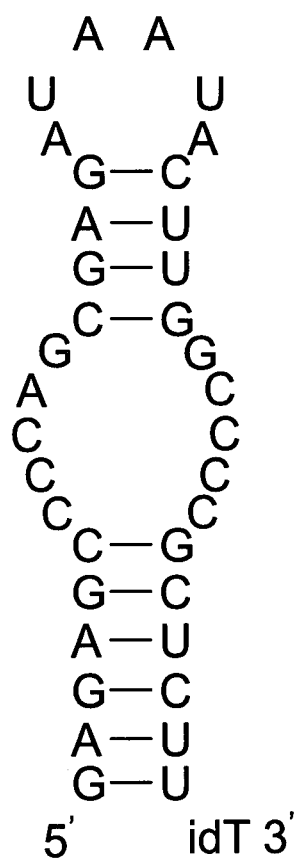
FIGS. 18A and 18B.
Figure 18B:
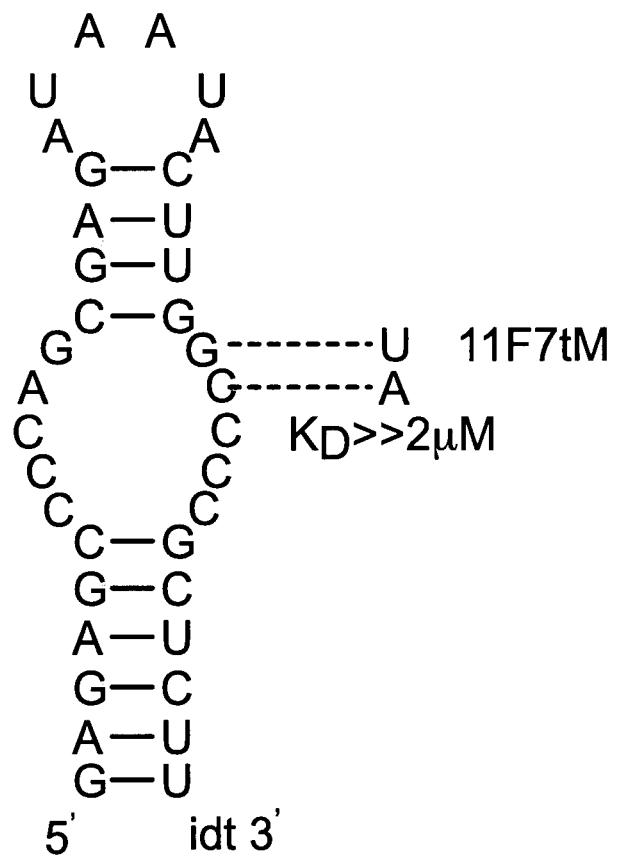
Figure 19A:
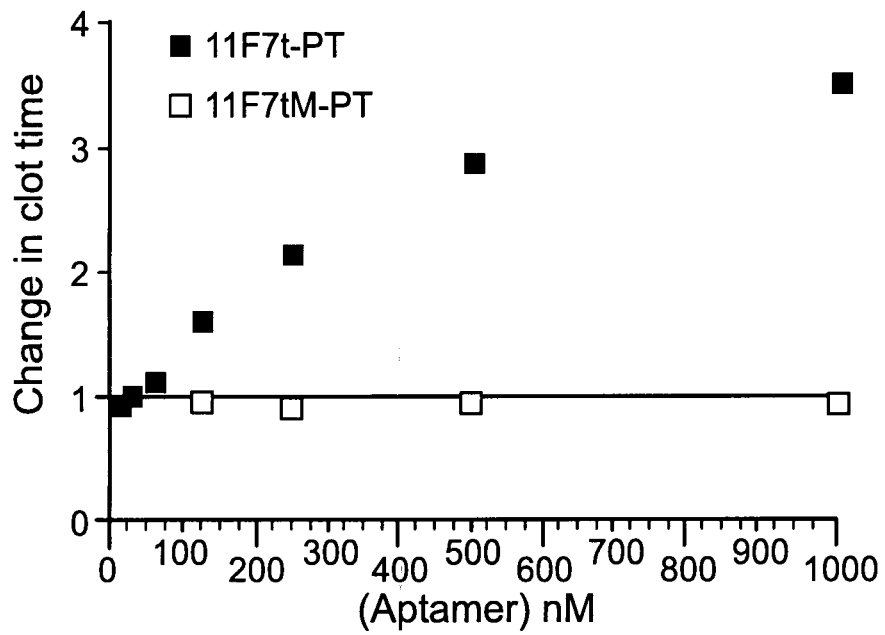
FIGS. 19A and 19B. Aptamer 11F7t is a potent anticoagulant of human plasma. Varying concentrations of aptamer 11F7t were added to human plasma in vitro, and the clot time was then measured in a PT (FIG. 19A) or APTT assay (FIG. 19B). All data are normalized to the baseline for that day, so that a value of 1 equals no change in clot time.
Figure 19B:
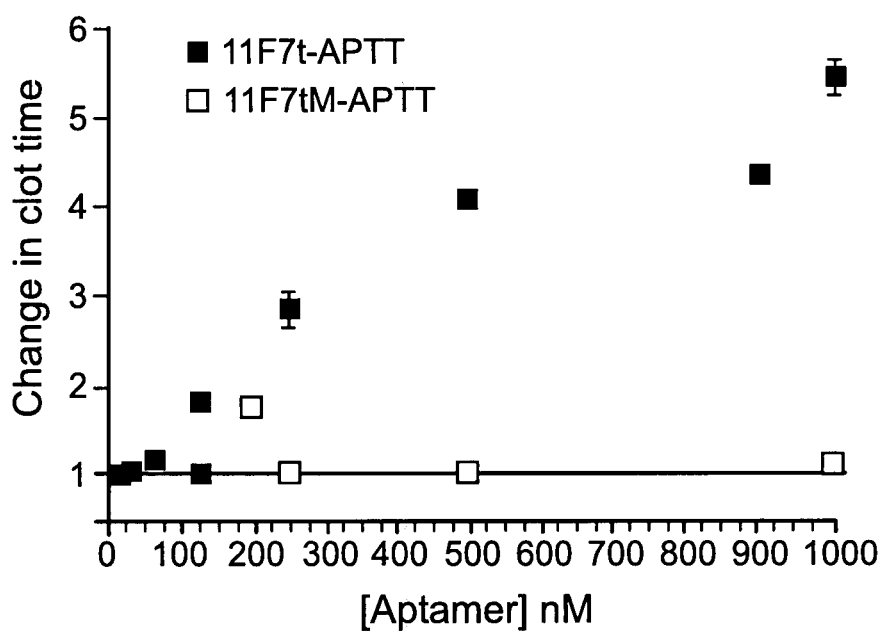

Depicted in FIG. 18A is an aptamer (designated 11F7t) against coagulation factor Xa that is a potent anticoagulant in vitro in human plasma. Depicted in FIG. 18B is a mutant version of aptamer 11F7t, designated 11F7t M. Alterations of the identity of the positions shown in FIG. 18B leads to a >1300 fold loss of affinity of the mutant aptamer for coagulation Fxa. Varying concentrations of aptamers 11F7t and 11F7t M were added to human plasma in vitro, and the clot time was then measured in a PT (FIG. 19A) or APTT assay (FIG. 19B). In FIG. 19, dotted lines indicate relative change in clot time of plasmas containing 10% or less than 1% the normal plasma level of FX, demonstrating the potent anticoagulant effects of aptamer 11F7t. All data are normalized to the baseline for that day, so that a value of 1=no change in clot time. Aptamer 11F7t is also a potent anticoagulant of human plasma when assays in PT clotting assays, as would be expected for a FXa inhibitor. The mutant aptamer, 11F7tM showed no anti coagulation activity in either the PT or APTT assay.

The following antidote oligonucleotides were screened for the ability to reverse the anticoagulant activity of aptamer 11F7t in vitro in human plasma:
AO 5-1: 5'CUC GCU GGG GCU CUC 3' (SEQ ID NO: 31)
AO 5-2: 5'UAU UAU CUC GCU GGG 3' (SEQ ID NO: 32)
AO 3-1: 5'AAG AGC GGG GCC AAG 3' (SEQ ID NO: 33)
AO 3-3: 5'GGG CCA AGU AUU AU 3' (SEQ ID NO: 34)

Figure 20:
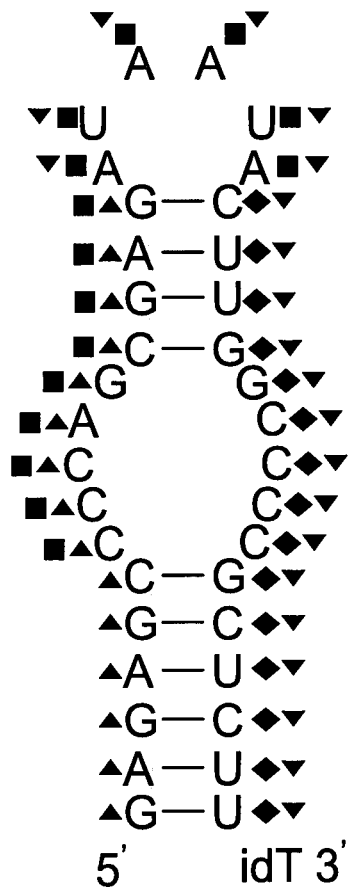
FIG. 20. Sequences of 11F7t to which the antidote oligos are complimentary.
Figure 21A:
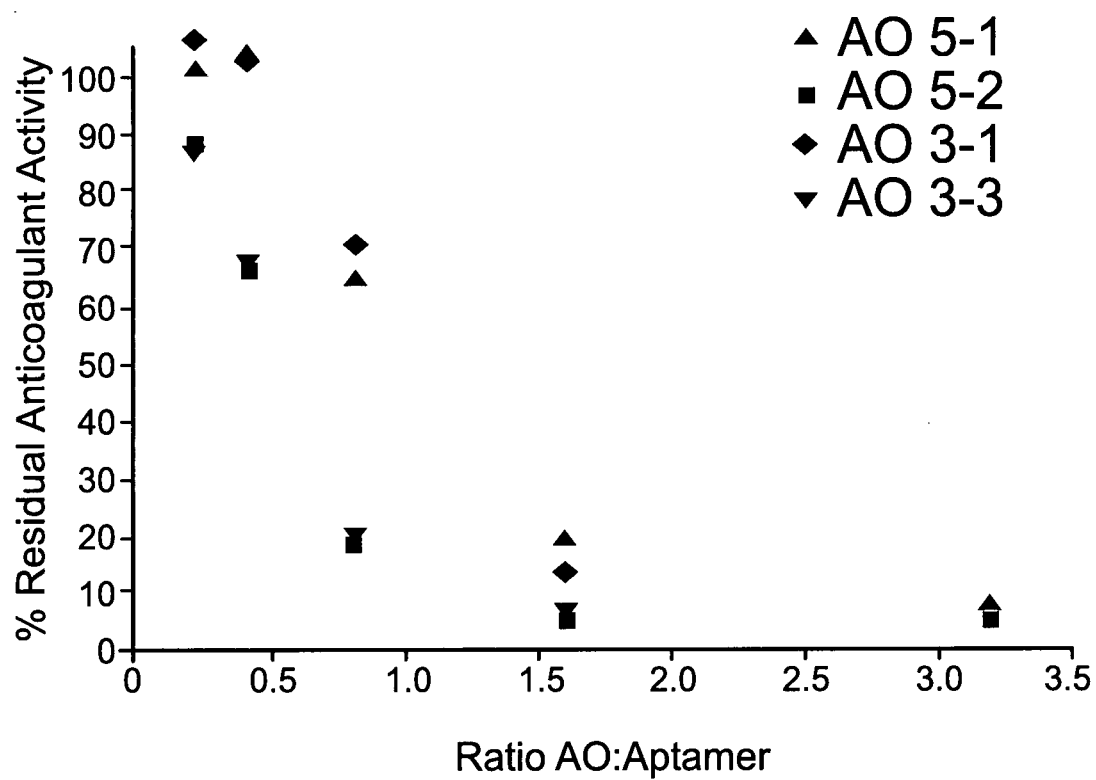
FIGS. 21A and 21B.

FIG. 20 shows the sequences of 11F7t to which these antidote oligonucleotides are complimentary. As shown in FIG. 21A, the antidote oligonucleotides effectively reverse the activity of aptamer 11F7t in human plasma. In these experiments, aptamer was added to plasma (final concentration 125 nM) and allowed to incubate for 5 minutes. Antidote oligonucleotides were then added, and APTT assays were initiated 10 minutes after antidote addition. In addition to the antidote oligonucleotides described above, the following sequences were also found to have antidote activity against aptamer 11F7t:
AO 3-2: 5'CAA GAG CGG GGC CAA G 3' (SEQ ID NO: 35)
AO 5-3: 5' CGA GUA WUA UCU UG 3' (SEQ ID NO: 36)

Figure 21B:
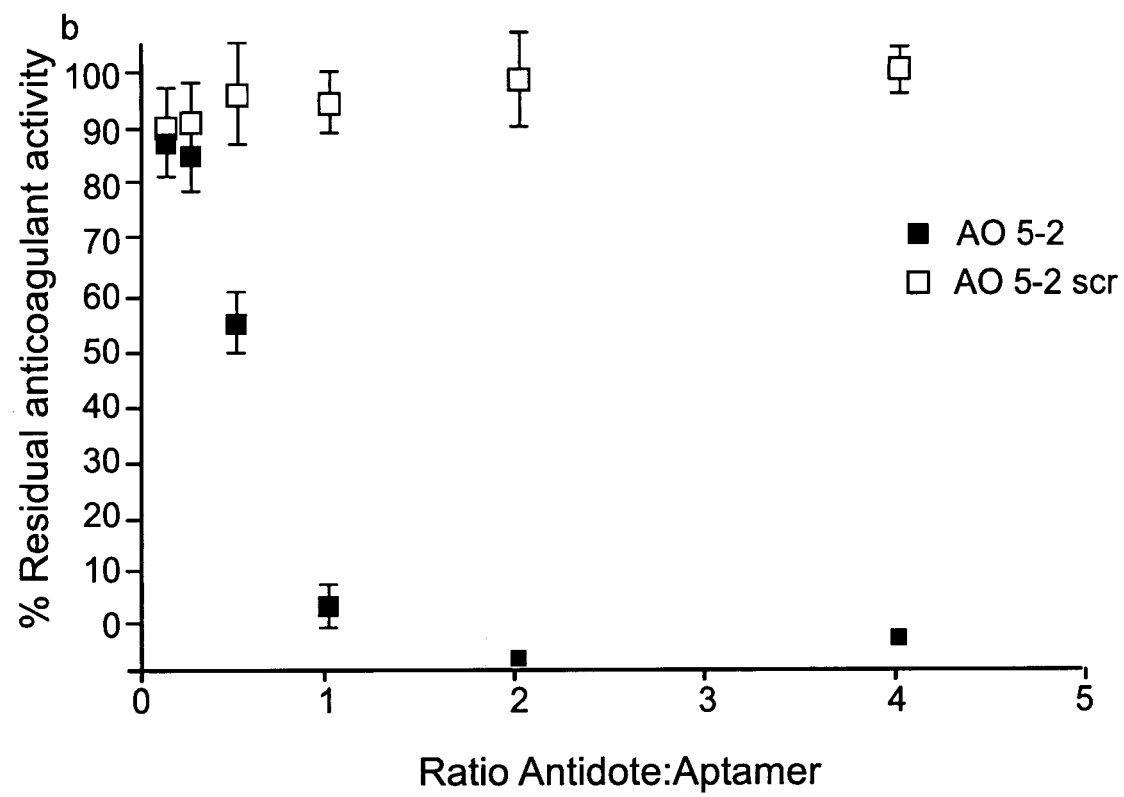

FIG. 21B shows the characterization of antidote 5-2 activity over a larger concentration range of antidote 5-2, and comparison to the antidote activity of a scrambled sequence version of antidote 5-2, 5-2scr. The data demonstrate potent reversal activity of antidote 5-2, and specificity of antidote oligonucleotide activity as demonstrated by lack of reversal activity of AO 5-2scr.

Figure 22:
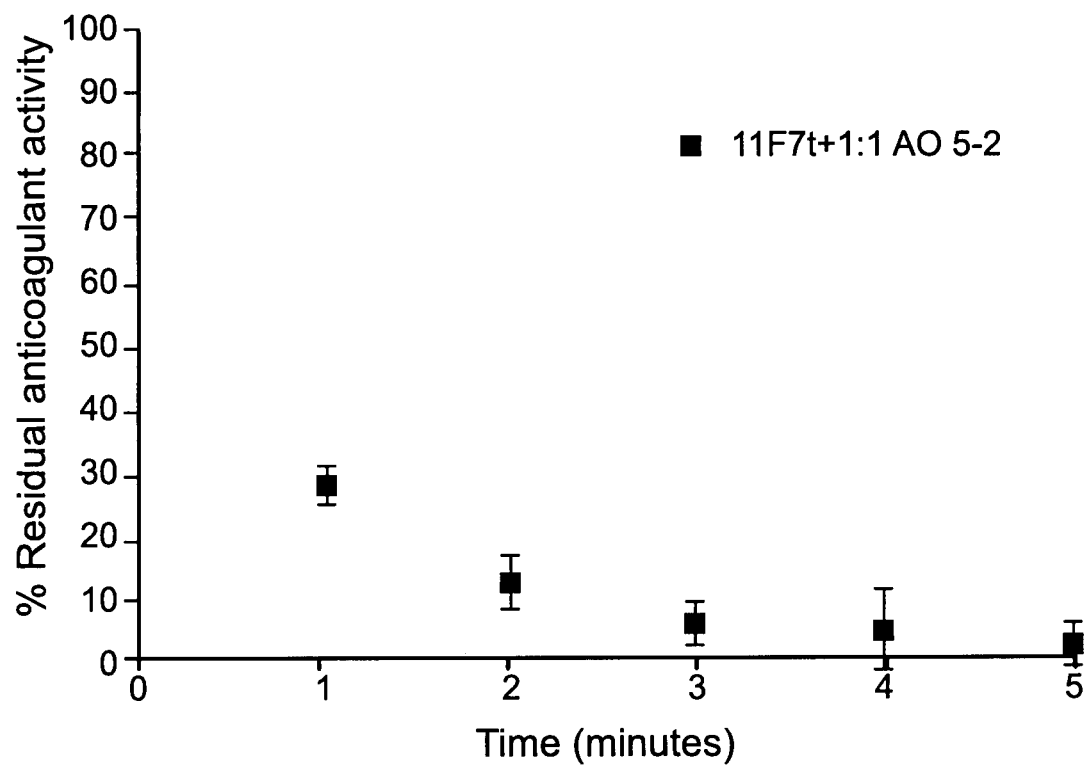
FIG. 22. Kinetics of antidote activity in human plasma. Aptamer 11F7t was added to human plasma in vitro at a final concentration of 125 nM, and allowed to incubate for 5 minutes at 37° C. Antidote oligonucleotide 5-2 at a 1:1 or 5:1 molar excess or no antidote were then added, and the clotting activity of the plasma determined by measuring the clotting time in a PT assay at the times indicated following antidote addition. The % residual anticoagulant activity remaining was calculated by comparing the difference over baseline between the clotting time in the presence of antidote to the difference over baseline in the absence of antidote at each time point. The data collected at a 5:1 molar excess of antidote 5-2 to aptamer 11F7t is not shown, as reversal of the anticoagulant activity was complete at the first time point (1 minute).
Figure 23:
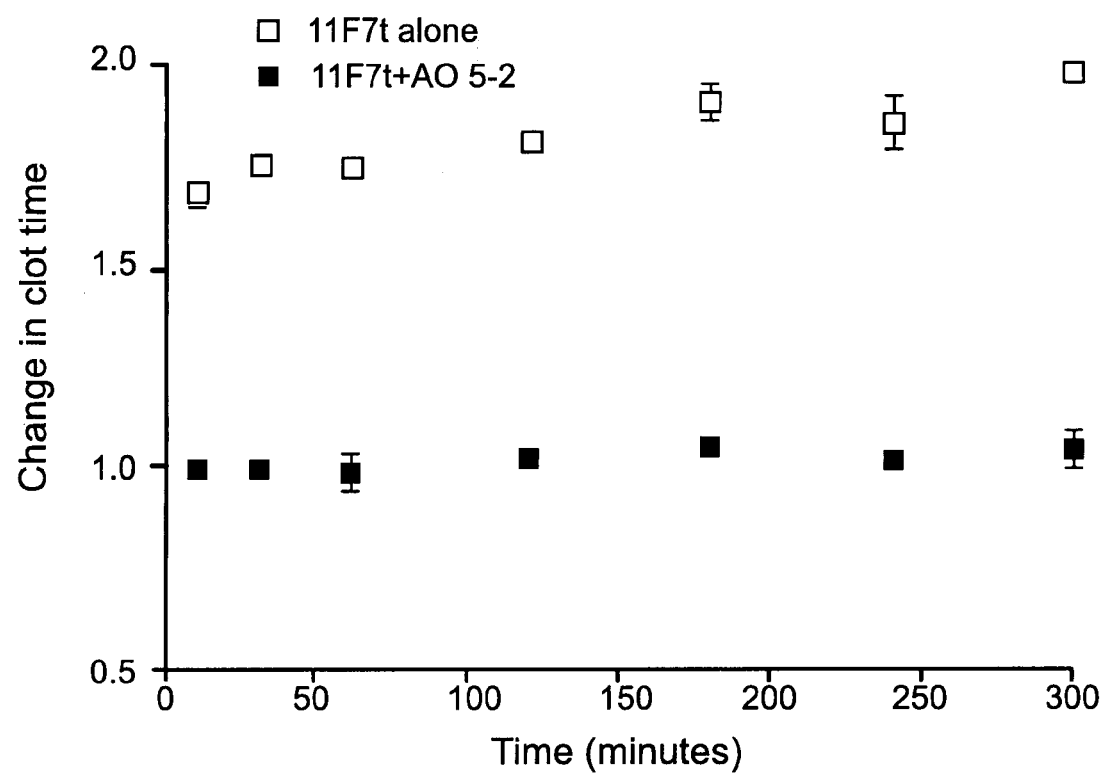
FIG. 23. Duration of antidote activity in vitro. The duration of the inactivation of the anticoagulant activity of aptamer 11F7t by antidote oligonucleotide 5-2 was measured in vitro in human plasma. Briefly, 11F7t was added to human plasma to a final concentration of 125 mM and allowed to incubate for 5 minutes. Antidote oligonucleotide 5-2 was then added at a 4 fold molar excess, or in a parallel experiment buffer alone was added in place of the antidote oligo, and the clotting time was measured in an a PT assay at various time points following antidote addition. All data is normalized to the baseline for that day, so that a value of 1=no change in clot time. It was found that after 5 hours of incubation at 37° C., the PT of the untreated plasma began to increase, indicating the loss of the clot forming activity of the plasma, and the experiment was thus stopped at 5 hours.

FIGS. 22 and 23 relate to the ability to rapidly and durably control the anticoagulant activity of the FXa antagonist aptamer 11F7t, and its derivatives, using antidote oligonucleotides. Together these data demonstrate that the onset of action of the antidote is rapid (FIG. 22), that the time needed for the antidote to act is at least in part dependent on the antidote concentration (FIG. 22), and that once the antidote has inactivated the aptamer, this effect is durable (FIG. 23). Together these data indicate that antidote oligonucleotides can be intravenously infused into a human or other animal would be a potential method to use antidote oligonucleotides to modulate the activity of a therapeutic aptamer. Furthermore, because the antidote activity is durable, once the desired level of modulation of the aptamer by the antidote is achieved, infusion of the antidote can be terminated, allowing residual antidote to clear the human or animal. This allows for subsequent re-treatment of the human or animal with the aptamer as needed.

EXAMPLE 8

Independent Functioning of Aptamer Antidote Pairs

Figure 24:
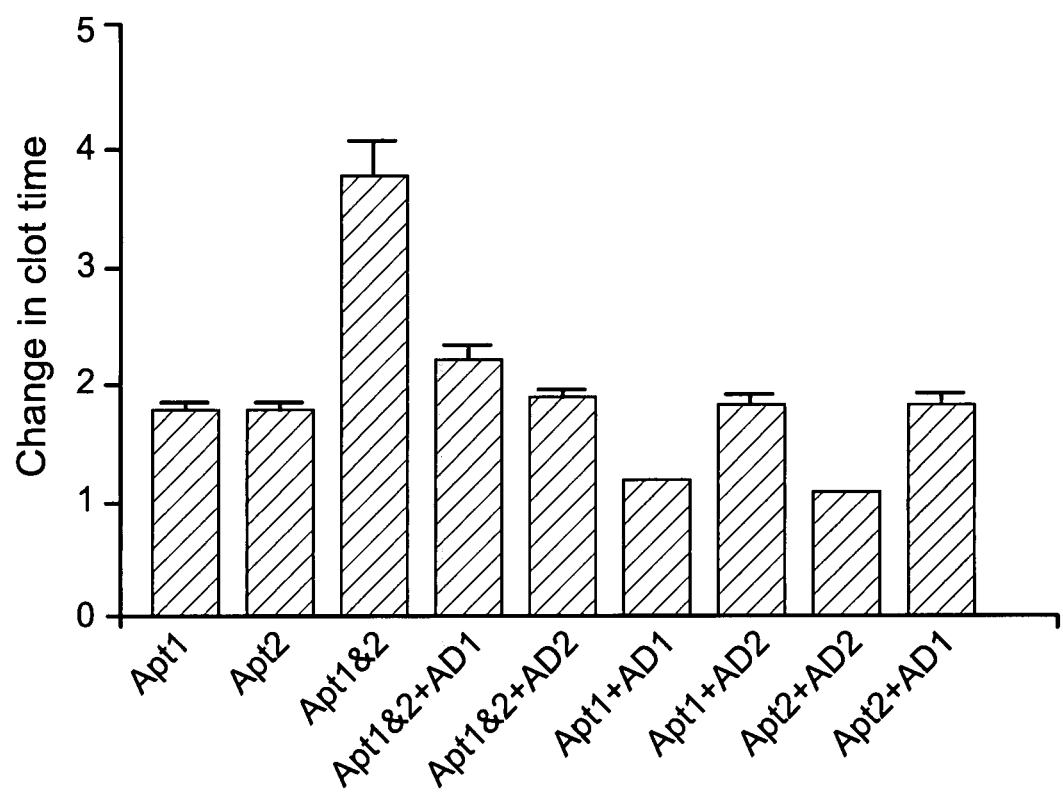
FIG. 24. Aptamers 9.3t and 11F7t and their respective antidotes function independent of each other in human plasma. Apt1=9.3t (30 nM), Apt2=11F7t (100 nM), AD1=AO 5−2c (300 nM), AD2=AO5=2 (500 nM)-final concentrations in plasma in ( ). Aptamers were added to human plasma at 37° C. as indicated, and allowed to incubate for 5 minutes. Antidotes were then added as indicated, and the clotting activity was measured 10 minutes after antidote addition in APTT assays. In all assays, buffer alone was substituted for aptamer or antidote in cases in which only one aptamer or antidote was added to the plasma. All data is normalized to the baseline for that day, so that a value of 1=no change in clot time.
Figure 25A:
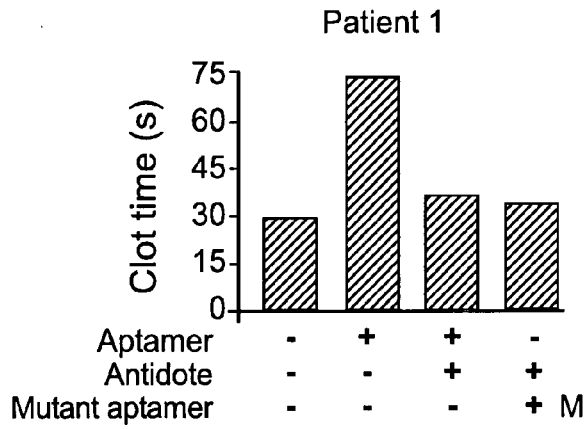
FIGS. 25A-25F. Antidote-controlled anticoagulation of plasma from patients with heparin-induced thrombocytopenia.
Figure 25D:
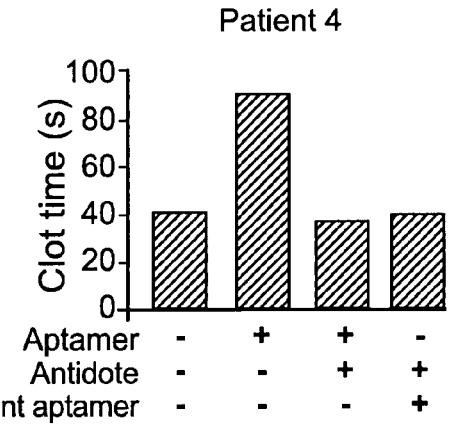
Figure 25B:
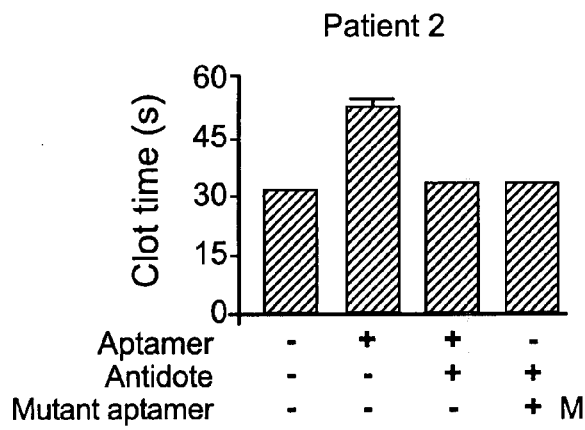
Figure 25E:
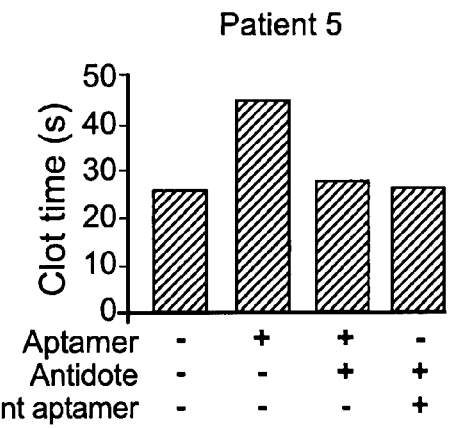
Figure 25C:
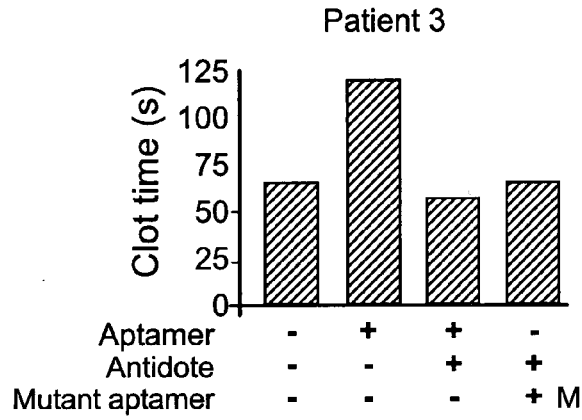
Figure 25F:
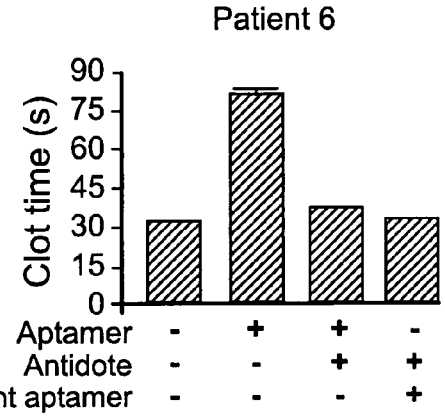

To demonstrate that aptamer-antidote pairs (aptamer 9.3t and its antidote A05-2c and aptamer 11F7t and its antidote A05-2) function independently of each other, aptamers were added to human plasma at 37° C., as indicated in FIG. 24, and allowed to incubate for 5 minutes. Antidotes were then added and the clotting activity was measured 10 minutes after antidote addition in APTT assays. In all assays, buffer alone was substituted for aptamer or antidote in cases in which only one aptamer or antidote was added to the plasma. All data was normalized to the baseline for that day, so that a value of 1=no change in clot time.

Comparing sample Apt 1&2+AD1 to Apt 1 alone and sample Apt 1&2+AD2 to Apt 2 alone (see FIG. 24), it is clear that antidote reversal activity is specific for the targeted aptamer (e.g., there was no loss of Apt 2 activity in the presence of AD 1 and vice versa), and the activity of the antidote was effectively unchanged by the presence of the second aptamer.

These results have two important implications. First, they demonstrate the ability to dose a patient with nucleic acid ligand 1 (e.g., 9.3t), reverse that nucleic acid ligand with its matched antidote, and then re-treat the patient with a second nucleic acid ligand. Second, the results demonstrate the utility of nucleic acid ligand-antidote pairs for target validation, and the study of biochemical pathways. The antidote enables one to determine that the response observed after inhibiting a target protein with an nucleic acid ligand is due to specifically inhibiting that protein. In addition, the antidote makes it possible to determine if binding of the nucleic acid ligand to the target protein leads to protein turnover. For example, if upon antidote addition complete protein activity is restored, it argues that there was no net change in protein concentration as a result of nucleic acid ligand binding.

EXAMPLE 9

Aptamer PEG-9.3t and Antidote 5-2C Function in Plasma from Patients with Heparin-Induced Thrombocytopenia (HIT)

The ability to control the anticoagulant activity of heparin with protamine enables safer treatment of patients undergoing procedures requiring a high level of anticoagulation, in whom the post-procedural risk of hemorrhage is high. However, ~3-5% of patients receiving heparin develop a drug-induced immunologic response termed heparin-induced thrombocytopenia (HIT), which contraindicates further treatment of these patients with heparin (Warkentin et al., *Thromb Haemost* 79:1-7. (1998)). This disorder is characterized by a decrease in the platelet count and an increased risk for new or recurrent life and limb-threatening thromboembolism (Warkentin et al., *Thromb Haemost* 79:1-7. (1998)) Several alternative anticoagulants are available, but none of these anticoagulants can be controlled by a reversing agent. This significantly limits the treatment options for patients with HIT, and hemorrhagic complications and recurrent thromboembolism while undergoing treatment are common Greinacher et al., *Circulation* 99:73-80. (1999), Lewis et al, *Circulation* 103:1838-1843. (2001)). Therefore, the ability of aptamer Peg-9.3t and antidote 5-2C to serve as an anticoagulant-antidote pair in plasma samples from six patients with HIT was investigated, three with end-stage renal disease requiring hemodialysis and thus repeated anticoagulation, and three with thromboembolic complications requiring anticoagulant therapy. (Serologic criteria included a positive heparin-induced platelet aggregation assay (Ortel et al, *Thromb Haemost* 67:292-296. (1992)) and/or elevated heparin/platelet factor 4 antibody levels detected by ELISA (GTI, Inc., Brookfield, Wis.). Five patients met both clinical and serologic criteria; one patient fulfilled clinical criteria but had negative serologic studies.) Aptamer PEG-9.3t prolonged the APTT clotting times of plasma from all six patients, and antidote 5-2 was able to effectively reverse this anticoagulant activity to the pre-treatment baseline of each patient (FIG. 25). Importantly, two patients were receiving anticoagulant therapy at the time samples were taken (patient 3 on danaproid sodium and patient 6 on warfarin), and PEG-9.3t addition to plasma from these patients increased the clot time over the treatment baseline and antidote 5-2C reversed this response back to the treatment baseline, demonstrating that in patient plasma this drug-antidote pair can function independently of an "on board" anticoagulant. In addition, treatment of these patient plasma samples with the control aptamer 9.3tM and antidote 5-2C yielded no increase in the clot time, further indicating that oligonucleotides of the composition of the aptamer or antidote do not inherently possess significant anticoagulant activity.

Figure 26A:
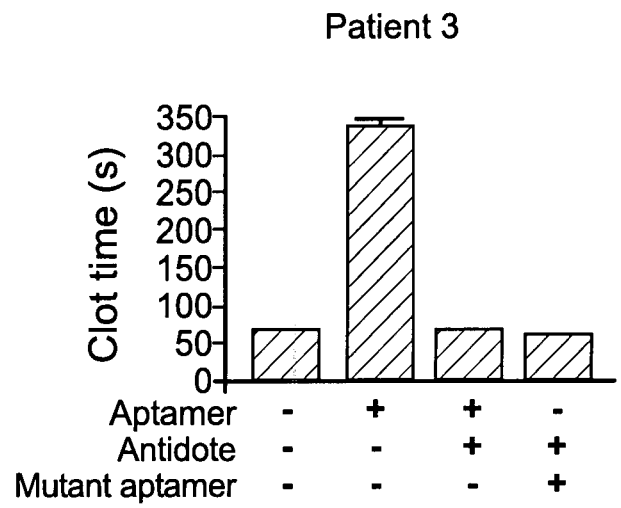
FIGS. 26A and B. Antidote-controlled anticoagulation of plasma from patients with heparin-induced thrombocytopenia. The activity of aptamer 11F7t and antidote 5-2 were tested in plasma from a hemodialysis-dependent patient diagnosed with HIT and from a patient suffering from thromboembolic complications of HIT. For patient 3, plasma samples were treated as indicated: aptamer, 250 nM 11F7t; antidote, 1.0 µM AO 5-2; mutant aptamer, 250 nM 9.3tM. Experiments were performed as described in Example 2, FIG. 9. For Patient 6, plasma samples were treated as indicated: aptamer, 125 nM 11F7t; antidote, 250 nM AO 5-2; mutant aptamer, 125 nM 9.3tM. Data is reported in seconds (s) and is the average ± range of duplicate measurements.
Figure 26B:
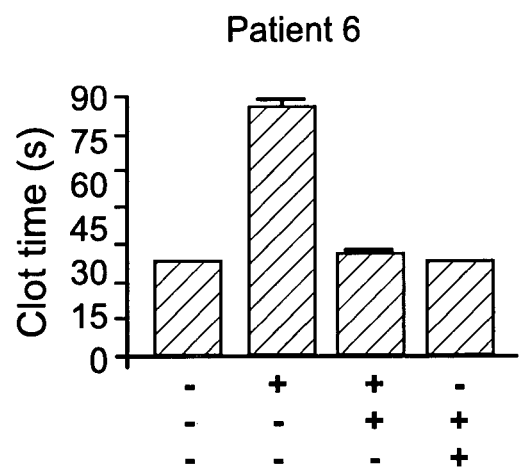

The ability of aptamer 11F7t and it's corresponding antidote 5-2 to serve as an anticoagulant-antidote pair in plasma samples from 2 patients with HIT, one with end-stage renal disease requiring hemodialysis and thus repeated anticoagulation, and one with thromboembolic complications requiring anticoagulant therapy. Aptamer 11F7t prolonged the APTT clotting times of plasma from both patients, and antidote 5-2 was able to effectively reverse this anticoagulant activity to the pre-treatment baseline of each patient (FIG. 26). Importantly, these two patients were receiving anticoagulant therapy at the time samples were taken (patient 3 on danaproid sodium and patient 6 on warfarin), and 11F7t addition to plasma from these patients increased the clot time over the treatment baseline and antidote 5-2 reversed this response back to the treatment baseline, demonstrating that in patient plasma this drug-antidote pair can function independently of an "on board" anticoagulant. In addition, treatment of these patient plasma samples with the control aptamer 9.3tM and antidote 5-2 yielded no increase in the clot time, further indicating that oligonucleotides of the composition of the aptamer or antidote do not inherently possess significant anticoagulant activity.

All documents cited above are hereby incorporated in their entirety by reference.

What is claimed is:

1. A method of altering the affinity of an aptamer for a coagulation factor in a host comprising administering to the host a modulator that binds to the aptamer, wherein the modulator is a nucleic acid binding peptide, polypeptide or protein which,
   (a) comprises a helix-loop-helix domain, a zinc finger domain, or a tripeptide which is selected from a combinatorial library to bind the aptamer, or
   (b) comprises an arginine rich motif, and
   wherein conditions are such that the modulator binds to the aptamer and alters the affinity of the aptamer for the coagulation factor.

2. The method according to claim 1 wherein upon binding of the modulator to the aptamer, the affinity of the aptamer for the target molecule is reduced.

3. The method according to claim 1 wherein upon binding of the modulator to the aptamer, the affinity of the aptamer for the coagulation factor is enhanced.

4. The method according to claim 1 wherein the modulator binds to free aptamer present in the host.

5. The method according to claim 1 wherein the modulator binds to aptamer ligand present in the host in association with the coagulation factor.

6. The method according to claim 1 wherein the coagulation factor is selected from the group consisting of a platelet receptor gpIIbIIIa; a platelet receptor gpIbIX; platelet receptor gpVI; a Gas6 receptor; angiogenesis factor 1 (Ang 1); angiogenesis factor 2 (Ang2); thrombin; a tissue factor/coagulation factor VIIa enzyme complex (TF/FVIIa); a coagulation factor VIIIa/coagulation factor IXa enzyme complex (FVIIIa/FIXa); a coagulation factor Va/coagulation factor Xa enzyme complex (FVa/FXa); plasminogen activator inhibitor 1 (PAI-1); coagulation factor XIIIa (FXIIIa); anti-thrombin III (ATIII); coagulation factor FIXa (FIXa); and coagulation factor XIa (FXIa).

7. The method according to claim 1 wherein the coagulation factor is Factor IXa.

8. The method of claim 1 wherein the nucleic acid binding peptide, polypeptide or protein comprises an arginine-rich motif.

9. The method of claim 8, wherein the nucleic acid binding peptide, polypeptide or protein comprises an arginine-rich motif about 10-20 amino acids in length.

* * * * *

```
SEQUENCE LISTING

<160> NUMBER OF SEQ ID NOS: 41

<210> SEQ ID NO 1
<211> LENGTH: 35
<212> TYPE: RNA
<213> ORGANISM: Artificial Sequence
<220> FEATURE:
<223> OTHER INFORMATION: Aptamer
<220> FEATURE:
<221> NAME/KEY: misc_feature
<222> LOCATION: (1)..(34)
<223> OTHER INFORMATION: All Pyrimidines (Cytosine and Uracil) are 2'-
      fluoro nucleotides; All Purines (Alanine and Guanine) are 2'-
      hydroxyl nucleotides
<220> FEATURE:
<221> NAME/KEY: misc_feature
<222> LOCATION: (35)..(35)
<223> OTHER INFORMATION: n = idT

<400> SEQUENCE: 1
auggggacua uaccgcguaa ugcugccucc ccaun                               35

<210> SEQ ID NO 2
<211> LENGTH: 40
<212> TYPE: RNA
<213> ORGANISM: Artificial Sequence
<220> FEATURE:
<223> OTHER INFORMATION: Aptamer

<400> SEQUENCE: 2 gggauggga cuauaccgcg uaaugcugcc uccccauucc                           40

<210> SEQ ID NO 3
<211> LENGTH: 29
<212> TYPE: RNA
<213> ORGANISM: Artificial Sequence
<220> FEATURE:
<223> OTHER INFORMATION: Aptamer

<400> SEQUENCE: 3
ggggacuaua ccggcaaucg ugcaucccc                                      29

<210> SEQ ID NO 4
<211> LENGTH: 30
<212> TYPE: RNA
<213> ORGANISM: Artificial Sequence
<220> FEATURE:
<223> OTHER INFORMATION: Aptamer

<400> SEQUENCE: 4
ugggaccaua acgacuacuc gugaauccca                                     30

<210> SEQ ID NO 5
<211> LENGTH: 27
<212> TYPE: RNA
<213> ORGANISM: Artificial Sequence
<220> FEATURE:
<223> OTHER INFORMATION: Aptamer

<400> SEQUENCE: 5
```
ugggcacuau acgcaucuug cugccug                                              27

<210> SEQ ID NO 6
<211> LENGTH: 27
<212> TYPE: RNA
<213> ORGANISM: Artificial Sequence
<220> FEATURE:
<223> OTHER INFORMATION: Aptamer

<400> SEQUENCE: 6
ugggcgauau acacauuggu gauccca                                              27

<210> SEQ ID NO 7
<211> LENGTH: 27
<212> TYPE: RNA
<213> ORGANISM: Artificial Sequence
<220> FEATURE:
<223> OTHER INFORMATION: Aptamer

<400> SEQUENCE: 7
gggaccauac gcacauugcu gaauccc                                              27

<210> SEQ ID NO 8
<211> LENGTH: 29
<212> TYPE: RNA
<213> ORGANISM: Artificial Sequence
<220> FEATURE:
<223> OTHER INFORMATION: Aptamer

<400> SEQUENCE: 8
ugggacuaua uucggaaucu ggacuccca                                            29

<210> SEQ ID NO 9
<211> LENGTH: 35
<212> TYPE: RNA
<213> ORGANISM: Artificial Sequence
<220> FEATURE:
<223> OTHER INFORMATION: Aptamer

<400> SEQUENCE: 9
gggaugggcu auauacacgc uggugauccc aucuc                                     35

<210> SEQ ID NO 10
<211> LENGTH: 33
<212> TYPE: RNA
<213> ORGANISM: Artificial Sequence
<220> FEATURE:
<223> OTHER INFORMATION: Aptamer

<400> SEQUENCE: 10
ggaugggcga uaaccaacau ggugauccca uuc                                       33

<210> SEQ ID NO 11
<211> LENGTH: 27
<212> TYPE: RNA
<213> ORGANISM: Artificial Sequence
<220> FEATURE:
<223> OTHER INFORMATION: Aptamer

<400> SEQUENCE: 11
ugggccauac guggacgacu gcacccg                                              27

<210> SEQ ID NO 12
<211> LENGTH: 27
<212> TYPE: RNA
<213> ORGANISM: Artificial Sequence

```
<220> FEATURE:
<223> OTHER INFORMATION: Aptamer

<400> SEQUENCE: 12
ugggccauaa ccacuuuggu gaaccca                                              27

<210> SEQ ID NO 13
<211> LENGTH: 30
<212> TYPE: RNA
<213> ORGANISM: Artificial Sequence
<220> FEATURE:
<223> OTHER INFORMATION: Aptamer

<400> SEQUENCE: 13
gggcgccaua cgcacauugc ugcaucgccu                                           30

<210> SEQ ID NO 14
<211> LENGTH: 28
<212> TYPE: RNA
<213> ORGANISM: Artificial Sequence
<220> FEATURE:
<223> OTHER INFORMATION: Aptamer

<400> SEQUENCE: 14
gggaccauaa cucuaacggg ugaauccc                                             28

<210> SEQ ID NO 15
<211> LENGTH: 29
<212> TYPE: RNA
<213> ORGANISM: Artificial Sequence
<220> FEATURE:
<223> OTHER INFORMATION: Aptamer

<400> SEQUENCE: 15
ggggacuaua cgugaacgac ugcauccac                                            29

<210> SEQ ID NO 16
<211> LENGTH: 26
<212> TYPE: RNA
<213> ORGANISM: Artificial Sequence
<220> FEATURE:
<223> OTHER INFORMATION: Aptamer

<400> SEQUENCE: 16
uggguaauaa cuguauggug aaccca                                               26

<210> SEQ ID NO 17
<211> LENGTH: 25
<212> TYPE: RNA
<213> ORGANISM: Artificial Sequence
<220> FEATURE:
<223> OTHER INFORMATION: Aptamer

<400> SEQUENCE: 17
gggugauaac cacucggug aaccc                                                 25

<210> SEQ ID NO 18
<211> LENGTH: 33
<212> TYPE: RNA
<213> ORGANISM: Artificial Sequence
<220> FEATURE:
<223> OTHER INFORMATION: Aptamer

<400> SEQUENCE: 18
auggggacua uaccggcaau cgugcauccc cau                                       33
```

```
<210> SEQ ID NO 19
<211> LENGTH: 38
<212> TYPE: RNA
<213> ORGANISM: Artificial Sequence
<220> FEATURE:
<223> OTHER INFORMATION: Aptamer
<220> FEATURE:
<221> NAME/KEY: misc_feature
<222> LOCATION: (35)..(35)
<223> OTHER INFORMATION: n = mG
<220> FEATURE:
<221> NAME/KEY: misc_feature
<222> LOCATION: (36)..(36)
<223> OTHER INFORMATION: n = mU
<220> FEATURE:
<221> NAME/KEY: misc_feature
<222> LOCATION: (37)..(37)
<223> OTHER INFORMATION: n = mC
<220> FEATURE:
<221> NAME/KEY: misc_feature
<222> LOCATION: (38)..(38)
<223> OTHER INFORMATION: n = idT

<400> SEQUENCE: 19
auggggacua uaccgcguaa ugcugccucc ccaunnnn                              38

<210> SEQ ID NO 20
<211> LENGTH: 20
<212> TYPE: RNA
<213> ORGANISM: Artificial Sequence
<220> FEATURE:
<223> OTHER INFORMATION: Aptamer

<400> SEQUENCE: 20
gacauggggs ggcagcauua                                                  20

<210> SEQ ID NO 21
<211> LENGTH: 17
<212> TYPE: RNA
<213> ORGANISM: Artificial Sequence
<220> FEATURE:
<223> OTHER INFORMATION: Aptamer

<400> SEQUENCE: 21
gacauggggs ggcagca                                                     17

<210> SEQ ID NO 22
<211> LENGTH: 14
<212> TYPE: RNA
<213> ORGANISM: Artificial Sequence
<220> FEATURE:
<223> OTHER INFORMATION: Aptamer

<400> SEQUENCE: 22
gacauggggs ggca                                                        14

<210> SEQ ID NO 23
<211> LENGTH: 37
<212> TYPE: RNA
<213> ORGANISM: Artificial Sequence
<220> FEATURE:
<223> OTHER INFORMATION: Aptamer
<220> FEATURE:
<221> NAME/KEY: misc_feature
<222> LOCATION: (37)..(37)
<223> OTHER INFORMATION: n = idT

<400> SEQUENCE: 23
gagagcccca gcgagauaau acuuggcccc gcucuun                               37
```

```
<210> SEQ ID NO 24
<211> LENGTH: 37
<212> TYPE: RNA
<213> ORGANISM: Artificial Sequence
<220> FEATURE:
<223> OTHER INFORMATION: Aptamer
<220> FEATURE:
<221> NAME/KEY: misc_feature
<222> LOCATION: (37)..(37)
<223> OTHER INFORMATION: n = idT

<400> SEQUENCE: 24
gagagcccca gcgagauaau acuuguaccc gcucuun                             37

<210> SEQ ID NO 25
<211> LENGTH: 17
<212> TYPE: RNA
<213> ORGANISM: Artificial Sequence
<220> FEATURE:
<223> OTHER INFORMATION: Aptamer

<400> SEQUENCE: 25
auggggaggc agcauua                                                    17

<210> SEQ ID NO 26
<211> LENGTH: 18
<212> TYPE: RNA
<213> ORGANISM: Artificial Sequence
<220> FEATURE:
<223> OTHER INFORMATION: Aptamer

<400> SEQUENCE: 26
cauggggagg cagcauua                                                   18

<210> SEQ ID NO 27
<211> LENGTH: 15
<212> TYPE: RNA
<213> ORGANISM: Artificial Sequence
<220> FEATURE:
<223> OTHER INFORMATION: Aptamer

<400> SEQUENCE: 27
cauggggagg cagca                                                      15

<210> SEQ ID NO 28
<211> LENGTH: 12
<212> TYPE: RNA
<213> ORGANISM: Artificial Sequence
<220> FEATURE:
<223> OTHER INFORMATION: Aptamer

<400> SEQUENCE: 28
cauggggagg ca                                                         12

<210> SEQ ID NO 29
<211> LENGTH: 23
<212> TYPE: RNA
<213> ORGANISM: Artificial Sequence
<220> FEATURE:
<223> OTHER INFORMATION: Aptamer

<400> SEQUENCE: 29
gcauuacgcg guauaguccc cua                                             23

<210> SEQ ID NO 30
<211> LENGTH: 17
<212> TYPE: RNA
<213> ORGANISM: Artificial Sequence
```

```
<220> FEATURE:
<223> OTHER INFORMATION: Aptamer

<400> SEQUENCE: 30
cgcgguauag uccccua                                                  17

<210> SEQ ID NO 31
<211> LENGTH: 15
<212> TYPE: RNA
<213> ORGANISM: Artificial Sequence
<220> FEATURE:
<223> OTHER INFORMATION: Aptamer

<400> SEQUENCE: 31
cucgcugggg cucuc                                                    15

<210> SEQ ID NO 32
<211> LENGTH: 15
<212> TYPE: RNA
<213> ORGANISM: Artificial Sequence
<220> FEATURE:
<223> OTHER INFORMATION: Aptamer

<400> SEQUENCE: 32
uauuaucucg cuggg                                                    15

<210> SEQ ID NO 33
<211> LENGTH: 15
<212> TYPE: RNA
<213> ORGANISM: Artificial Sequence
<220> FEATURE:
<223> OTHER INFORMATION: Aptamer

<400> SEQUENCE: 33
aagagcgggg ccaag                                                    15

<210> SEQ ID NO 34
<211> LENGTH: 14
<212> TYPE: RNA
<213> ORGANISM: Artificial Sequence
<220> FEATURE:
<223> OTHER INFORMATION: Aptamer

<400> SEQUENCE: 34
gggccaagua uuau                                                     14

<210> SEQ ID NO 35
<211> LENGTH: 16
<212> TYPE: RNA
<213> ORGANISM: Artificial Sequence
<220> FEATURE:
<223> OTHER INFORMATION: Aptamer

<400> SEQUENCE: 35
caagagcggg gccaag                                                   16

<210> SEQ ID NO 36
<211> LENGTH: 14
<212> TYPE: RNA
<213> ORGANISM: Artificial Sequence
<220> FEATURE:
<223> OTHER INFORMATION: Aptamer

<400> SEQUENCE: 36
cgaguauuau cuug                                                     14
```

```
-continued

<210> SEQ ID NO 37
<211> LENGTH: 12
<212> TYPE: RNA
<213> ORGANISM: Artificial Sequence
<220> FEATURE:
<223> OTHER INFORMATION: Aptamer

<400> SEQUENCE: 37 caugggaag ca                                                     12

<210> SEQ ID NO 38
<211> LENGTH: 11
<212> TYPE: RNA
<213> ORGANISM: Artificial Sequence
<220> FEATURE:
<223> OTHER INFORMATION: Aptamer

<400> SEQUENCE: 38
auggggaggc a                                                     11

<210> SEQ ID NO 39
<211> LENGTH: 14
<212> TYPE: RNA
<213> ORGANISM: Artificial Sequence
<220> FEATURE:
<223> OTHER INFORMATION: Aptamer

<400> SEQUENCE: 39 gacauggga agca                                                   14

<210> SEQ ID NO 40
<211> LENGTH: 14
<212> TYPE: RNA
<213> ORGANISM: Artificial Sequence
<220> FEATURE:
<223> OTHER INFORMATION: Aptamer

<400> SEQUENCE: 40
acaaugggga ggca                                                  14

<210> SEQ ID NO 41
<211> LENGTH: 17
<212> TYPE: RNA
<213> ORGANISM: Artificial Sequence
<220> FEATURE:
<223> OTHER INFORMATION: Aptamer

<400> SEQUENCE: 41
cgcgguauag uccccau                                               17
```